(12) United States Patent
Orsak et al.

(10) Patent No.: US 9,084,632 B2
(45) Date of Patent: *Jul. 21, 2015

(54) ORTHOPEDIC DEVICE

(71) Applicant: Wright Medical Technology, Inc., Memphis, TN (US)

(72) Inventors: James Edward Orsak, Eads, TN (US); Kian-Ming Wong, Cordova, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/080,851

(22) Filed: Nov. 15, 2013

(65) Prior Publication Data

US 2014/0081267 A1 Mar. 20, 2014

Related U.S. Application Data

(60) Continuation of application No. 13/271,288, filed on Oct. 12, 2011, now Pat. No. 8,585,702, which is a division of application No. 12/262,628, filed on Oct. 31, 2008, now Pat. No. 8,057,473.

(60) Provisional application No. 61/096,358, filed on Sep. 12, 2008, provisional application No. 60/984,012, filed on Oct. 31, 2007.

(51) Int. Cl.
*A61F 5/04* (2006.01)
*A61B 17/64* (2006.01)
*A61B 17/60* (2006.01)
*A61B 17/66* (2006.01)
(Continued)

(52) U.S. Cl.
CPC .............. *A61B 17/6466* (2013.01); *A61B 17/60* (2013.01); *A61B 17/6416* (2013.01); *A61B 17/66* (2013.01); *A61B 17/8605* (2013.01); *A61B 17/8875* (2013.01)

(58) Field of Classification Search
USPC ...................................................... 606/54–59
See application file for complete search history.

(56) References Cited

U.S. PATENT DOCUMENTS

| 4,422,334 A | 12/1983 | Yasuda |
| 4,475,546 A | 10/1984 | Patton |
| 4,628,919 A | 12/1986 | Clyburn |

(Continued)

FOREIGN PATENT DOCUMENTS

EP 0140786 A2 5/1985

OTHER PUBLICATIONS

International Search Report and Written Opinion for PCT/US08/81971, dated Jan. 21, 2009.

*Primary Examiner* — Jan Christopher Merene
(74) *Attorney, Agent, or Firm* — Duane Morris LLP

(57) ABSTRACT

An orthopedic device includes a fixator body having a first part and a second part that are connected by a joint and having an internally threaded bore extending longitudinally therethrough. A first pair of opposed longitudinally extending slots is provided in the first part and a second pair of opposed longitudinally extending slots is provided in the second part. A first and second pin-holders are received within and threadably engage the internally threaded bore of the first part and the second part, respectively, and are configured to removably hold a first and second sets of one or more bone fixation pins extending through the first and second pairs of opposed longitudinally extending slots, respectively.

7 Claims, 45 Drawing Sheets

(51) Int. Cl.
*A61B 17/86* (2006.01)
*A61B 17/88* (2006.01)

(56) References Cited

U.S. PATENT DOCUMENTS

| | | | |
|---|---|---|---|
| 4,745,913 A | 5/1988 | Castaman et al. |
| 4,922,896 A | 5/1990 | Agee et al. |
| 4,969,886 A | 11/1990 | Cziffer et al. |
| 4,988,349 A | 1/1991 | Pennig |
| 5,320,622 A | 6/1994 | Faccioli et al. |
| 5,454,810 A | 10/1995 | Pohl et al. |
| 5,540,687 A | 7/1996 | Fairley et al. |
| 5,556,398 A | 9/1996 | Bagits et al. |
| 5,562,666 A | 10/1996 | Brumfield |
| 5,643,258 A | 7/1997 | Robioneck et al. |
| 5,653,707 A | 8/1997 | Taylor et al. |
| 5,662,650 A | 9/1997 | Bailey et al. |
| 5,674,221 A | 10/1997 | Hein et al. |
| 5,738,684 A | 4/1998 | Thomas et al. |
| 5,855,580 A | 1/1999 | Kreidler et al. |
| 5,951,556 A | 9/1999 | Faccioli et al. |
| 6,024,745 A | 2/2000 | Faccioli et al. |
| 6,171,309 B1 | 1/2001 | Huebner |
| 6,228,086 B1 | 5/2001 | Wahl et al. |
| 6,423,069 B1 | 7/2002 | Sellers |
| 6,500,177 B1 | 12/2002 | Martinelli et al. |
| 6,562,042 B2 | 5/2003 | Nelson |
| 6,569,165 B2 | 5/2003 | Wahl et al. |
| 2002/0077629 A1 | 6/2002 | Hoffman et al. |
| 2004/0097944 A1 | 5/2004 | Koman et al. |
| 2004/0260284 A1 | 12/2004 | Parker |
| 2005/0240180 A1 | 10/2005 | Vienney et al. |
| 2005/0261687 A1 | 11/2005 | Garamszegi et al. |
| 2006/0095035 A1 | 5/2006 | Jones et al. |
| 2006/0229605 A1 | 10/2006 | Olsen |
| 2007/0055244 A1 | 3/2007 | Jackson |
| 2007/0123857 A1 | 5/2007 | Deffenbaugh et al. |

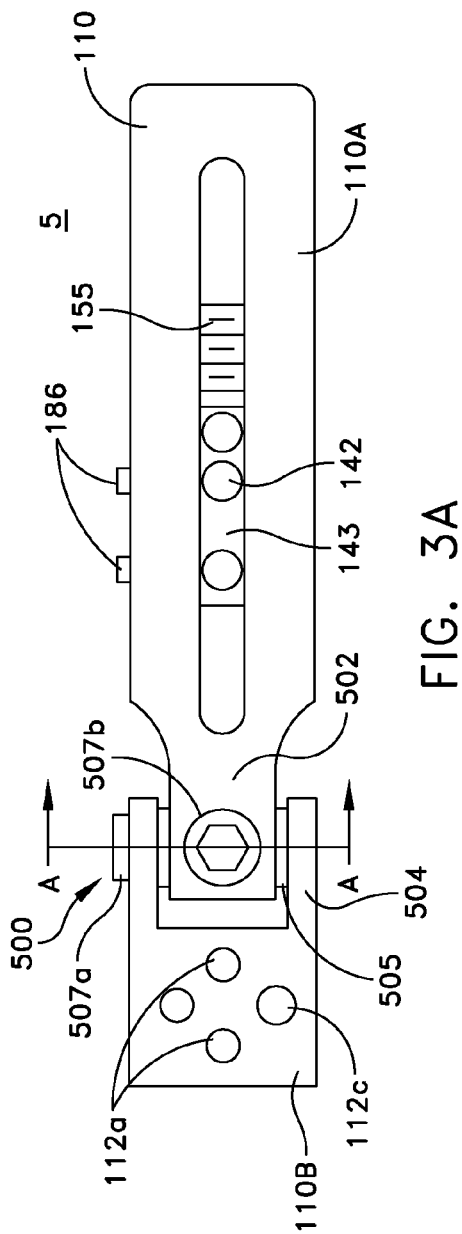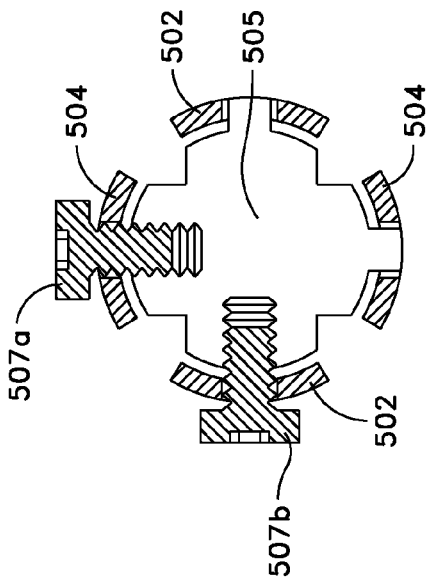
FIG. 3A
FIG. 3B

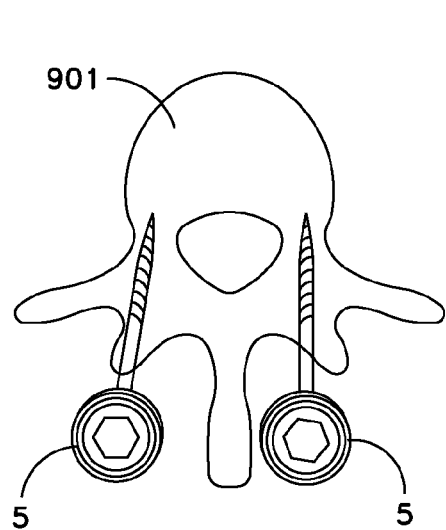
FIG. 6A
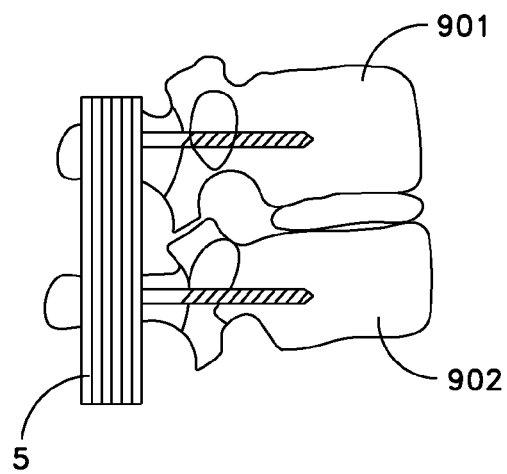
FIG. 6B
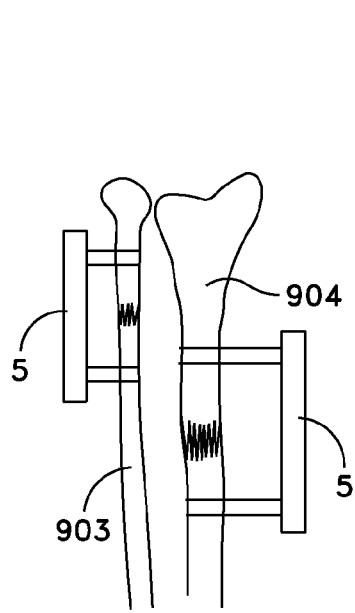
FIG. 7A
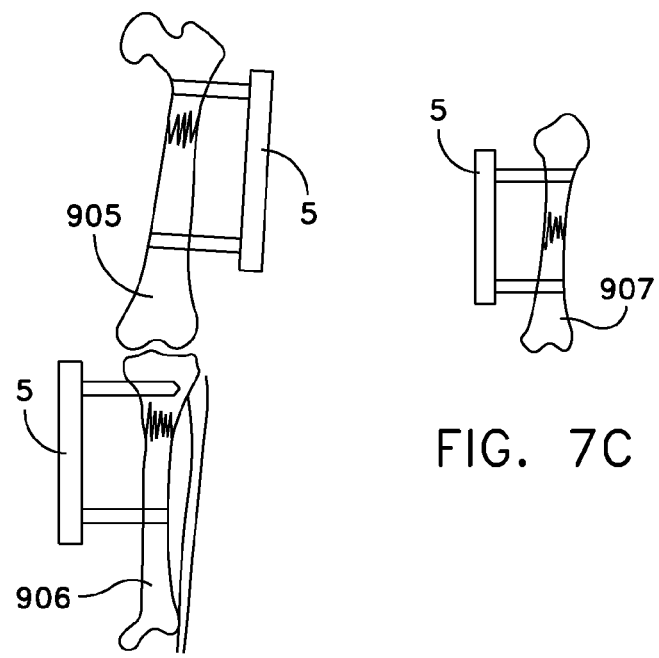
FIG. 7B
FIG. 7C

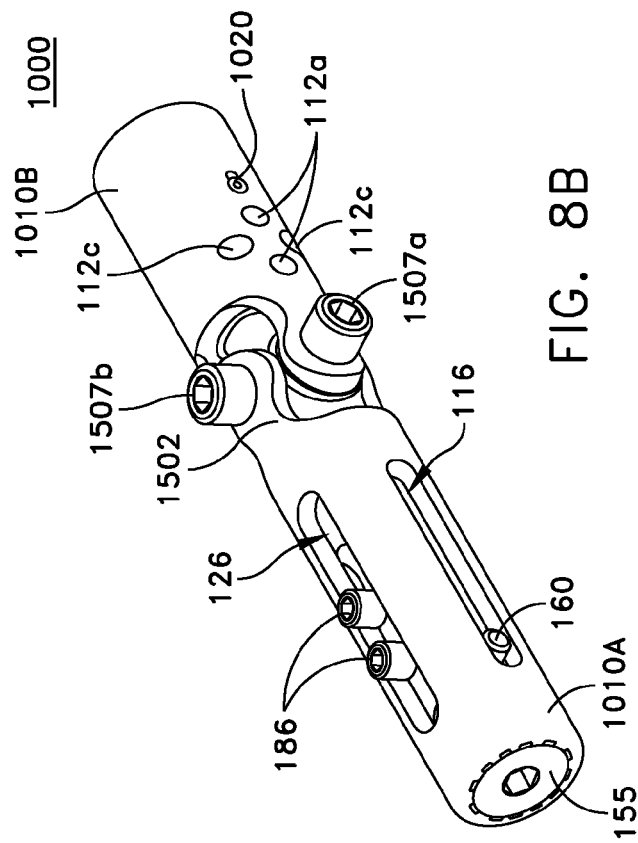
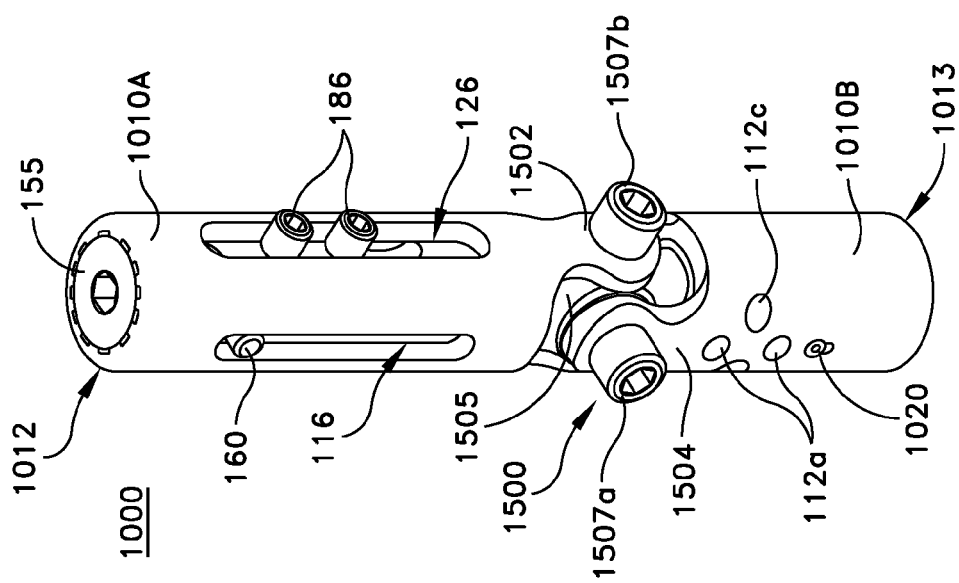
FIG. 8B
FIG. 8A

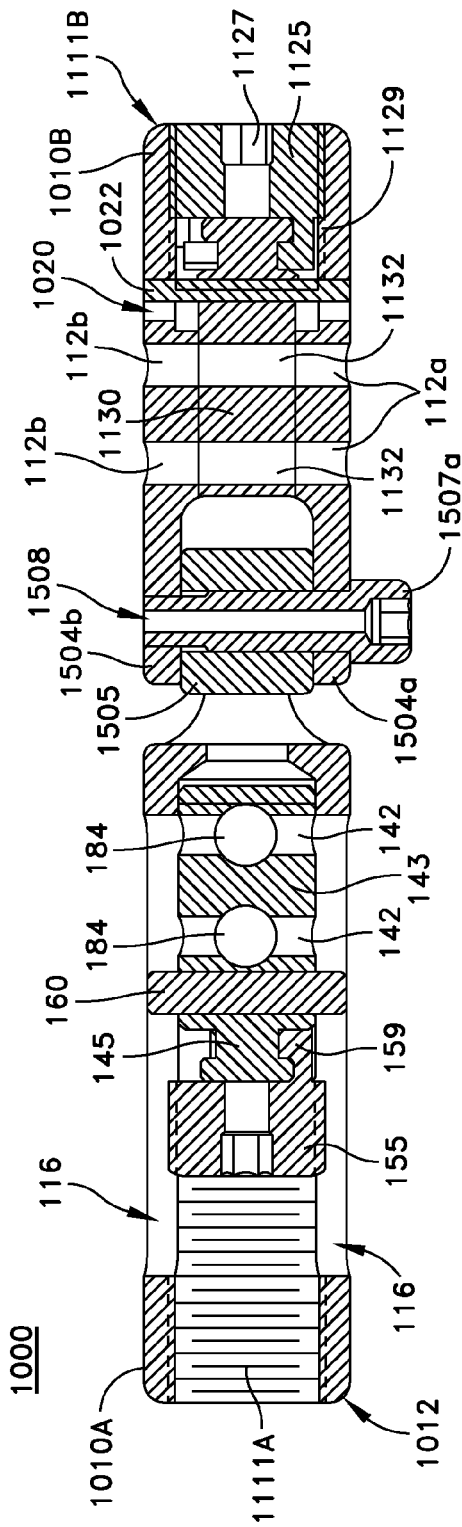
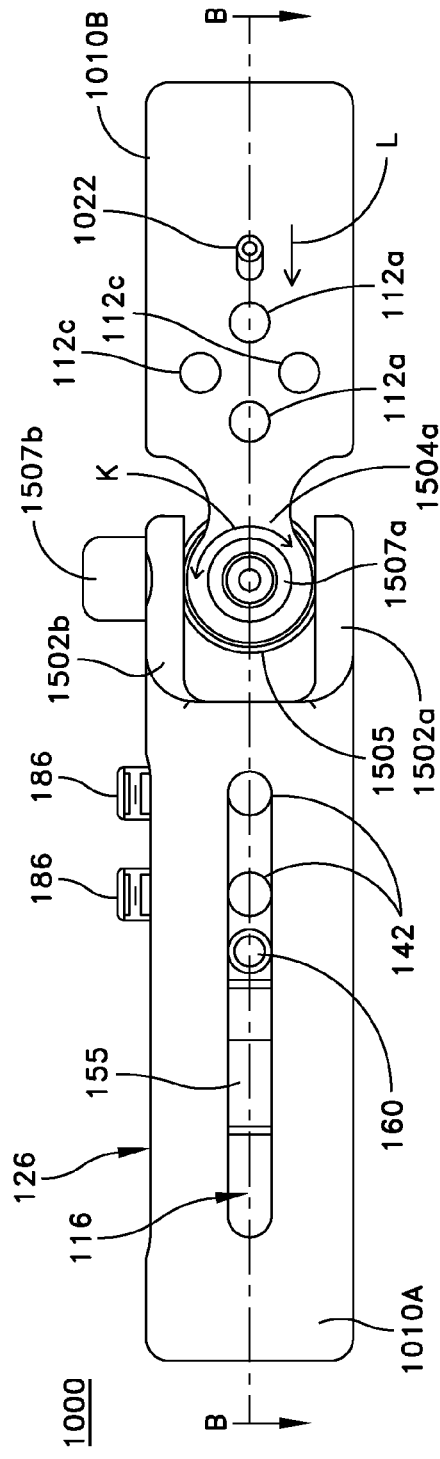
FIG. 9A
FIG. 9B

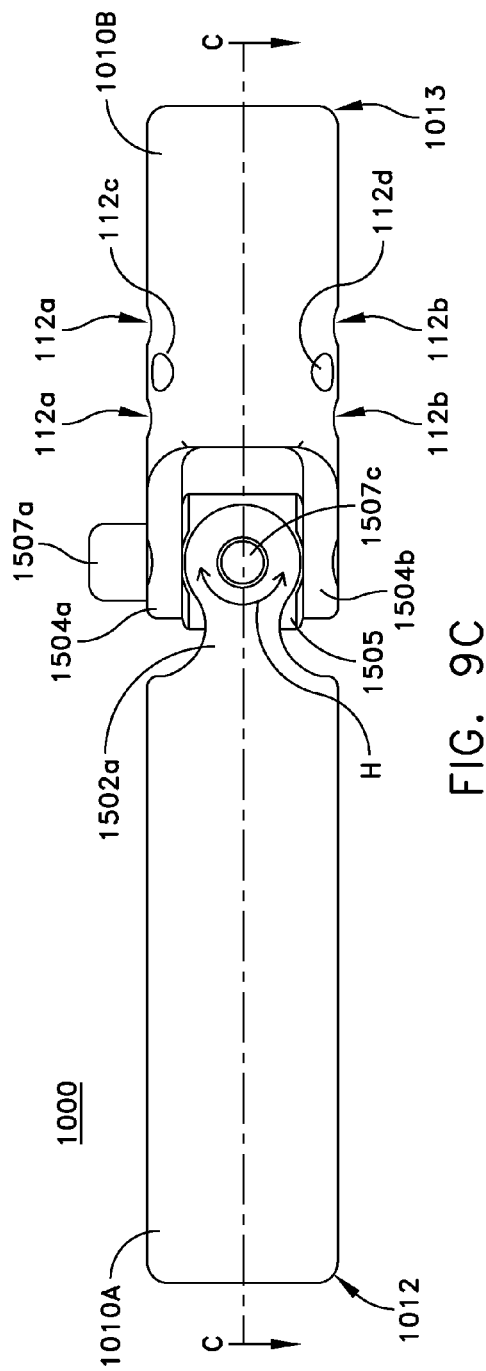
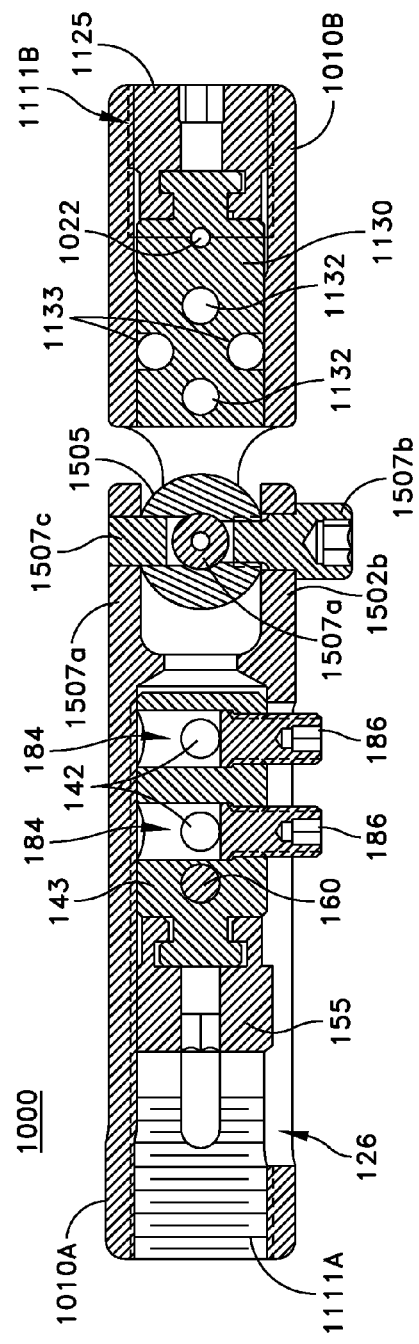
FIG. 9C
FIG. 9D

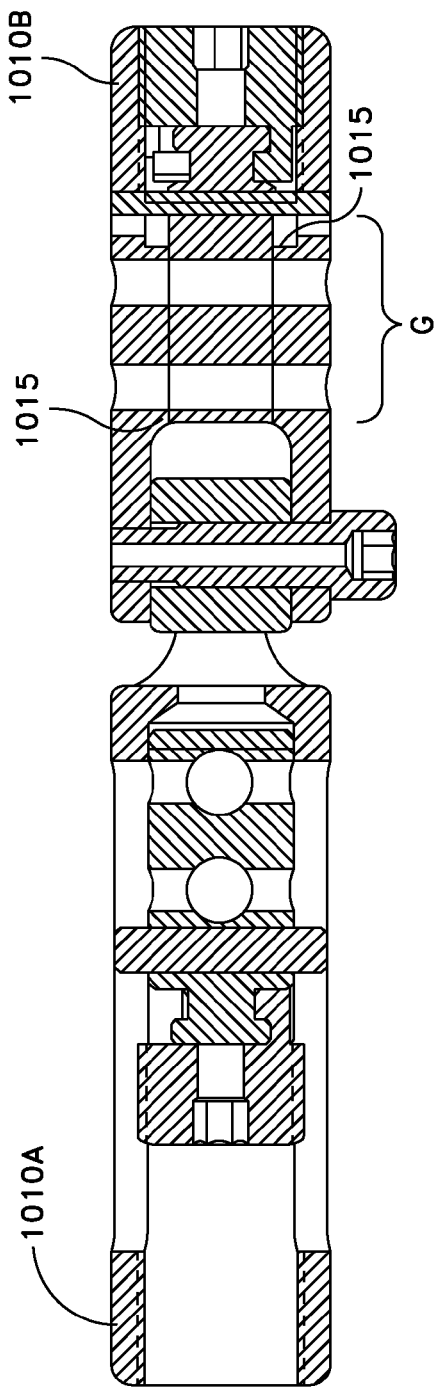
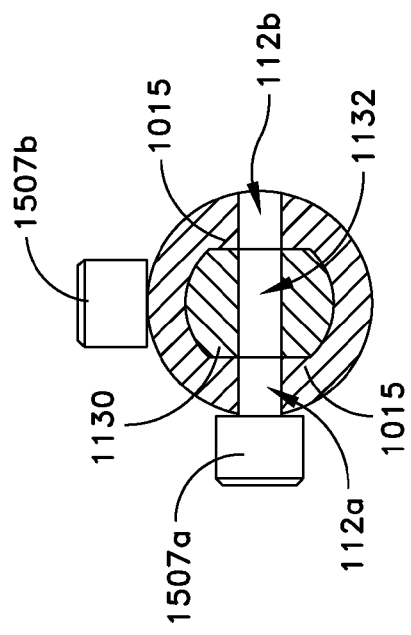

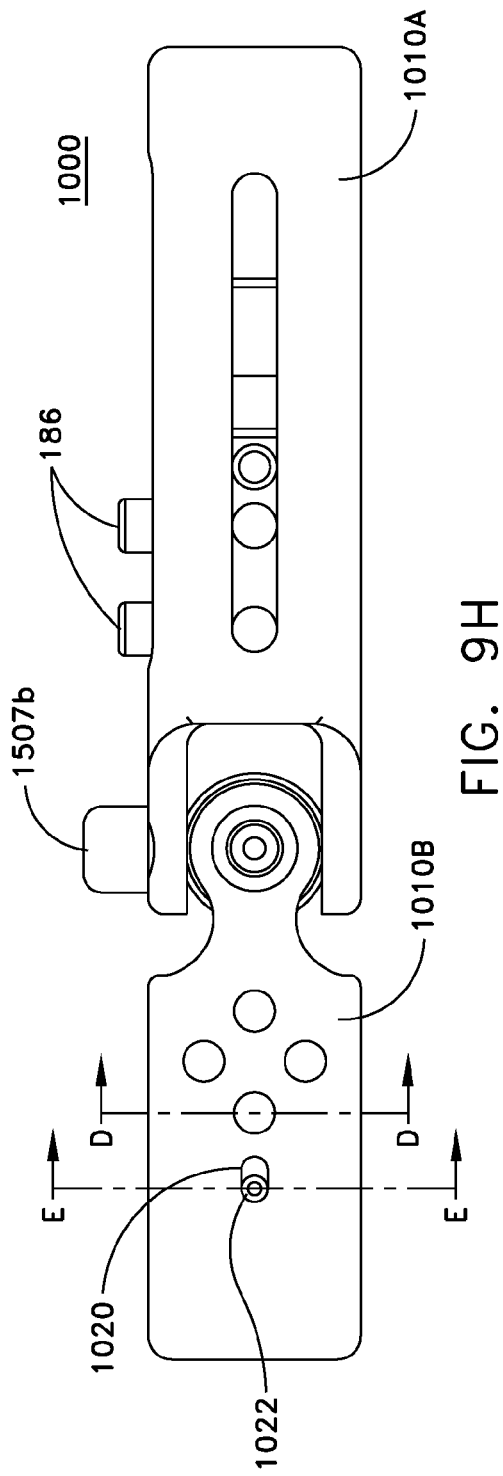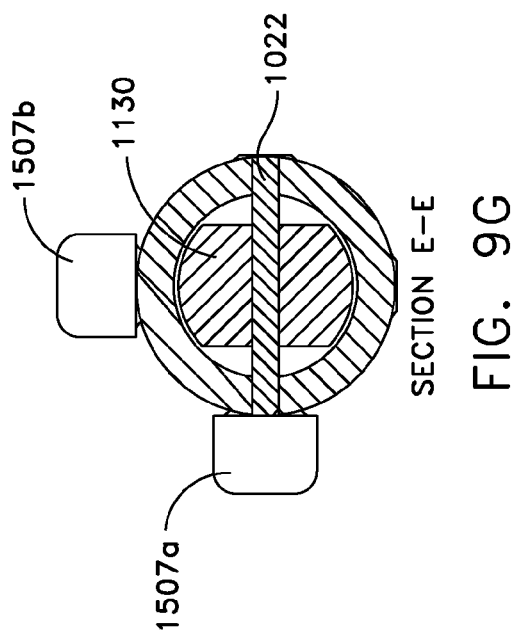

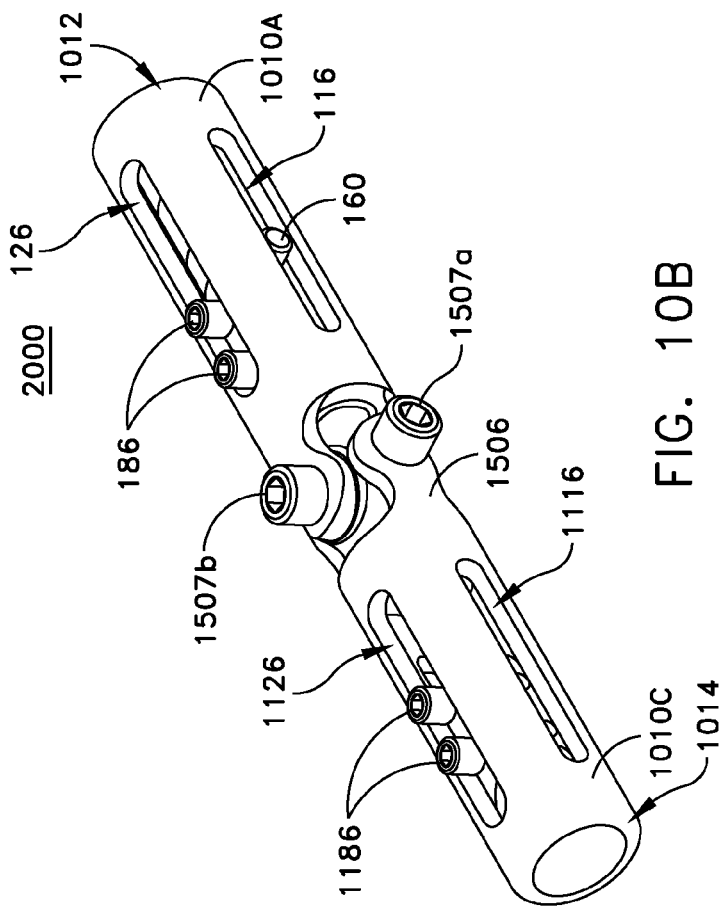
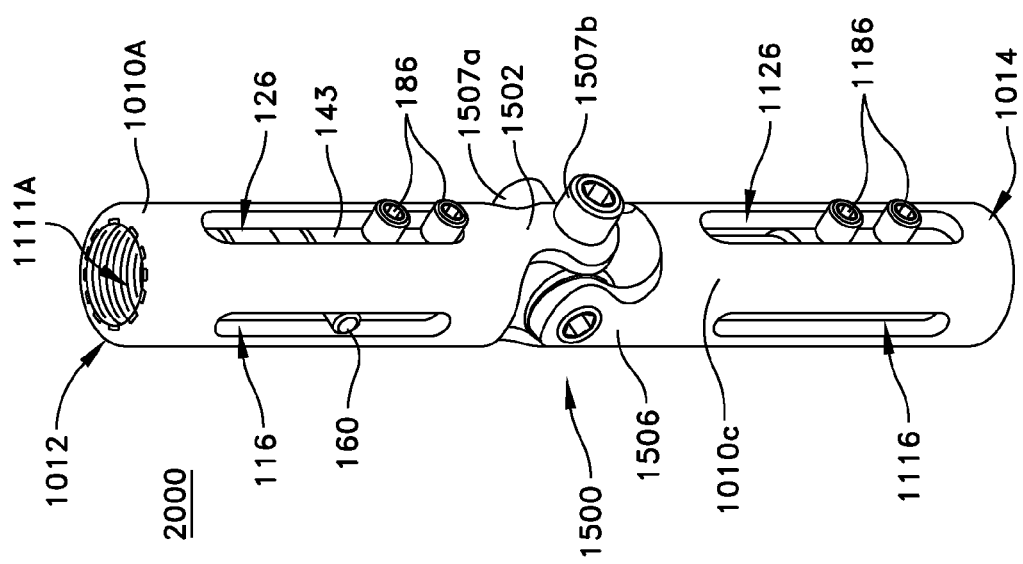
FIG. 10B
FIG. 10A

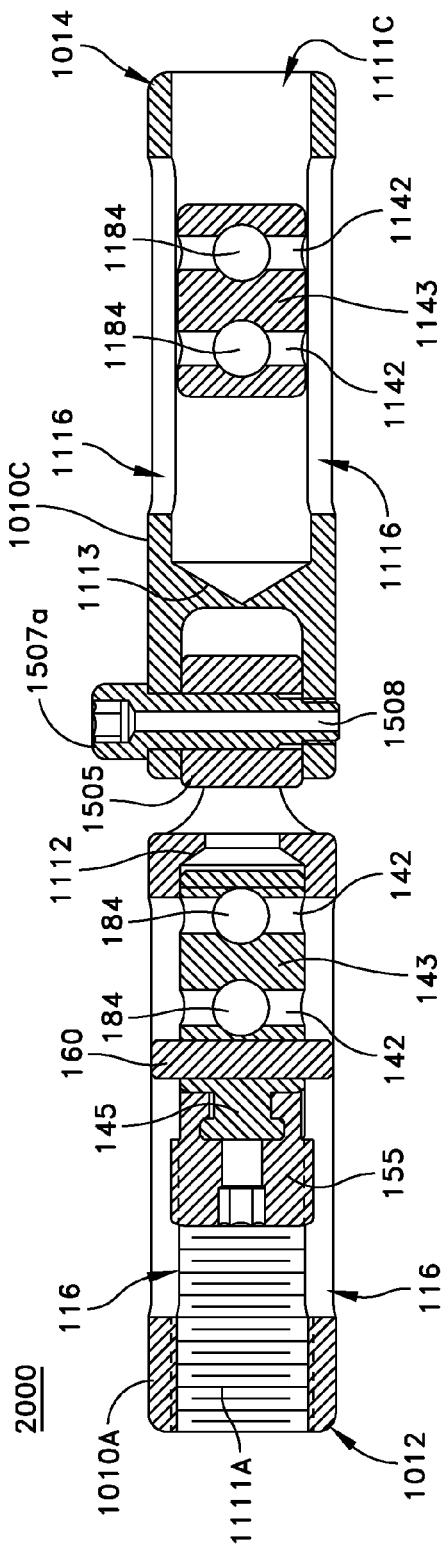
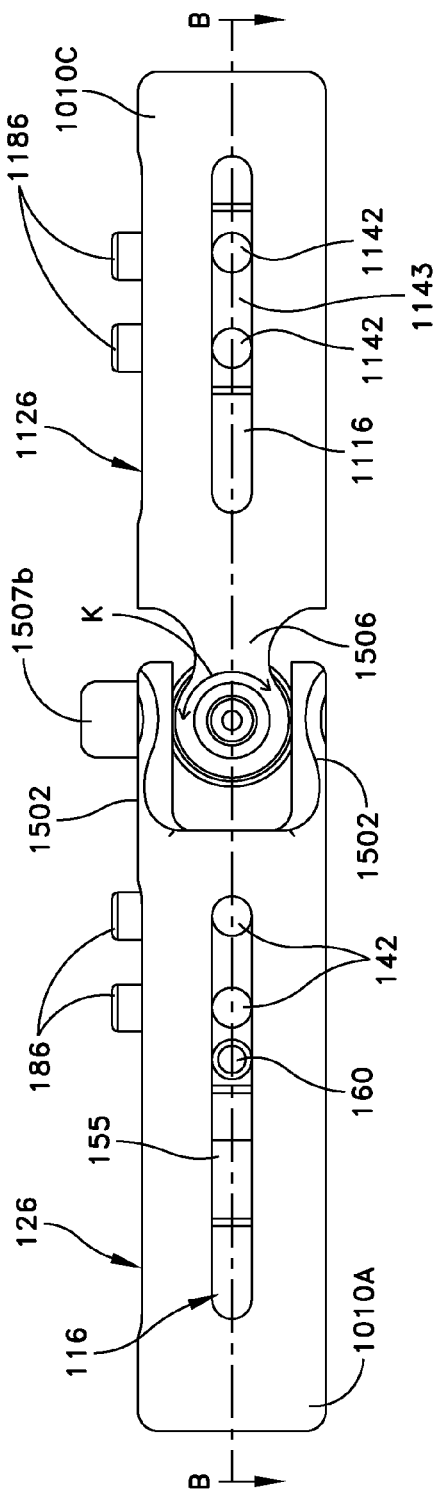
FIG. 10C
FIG. 10D

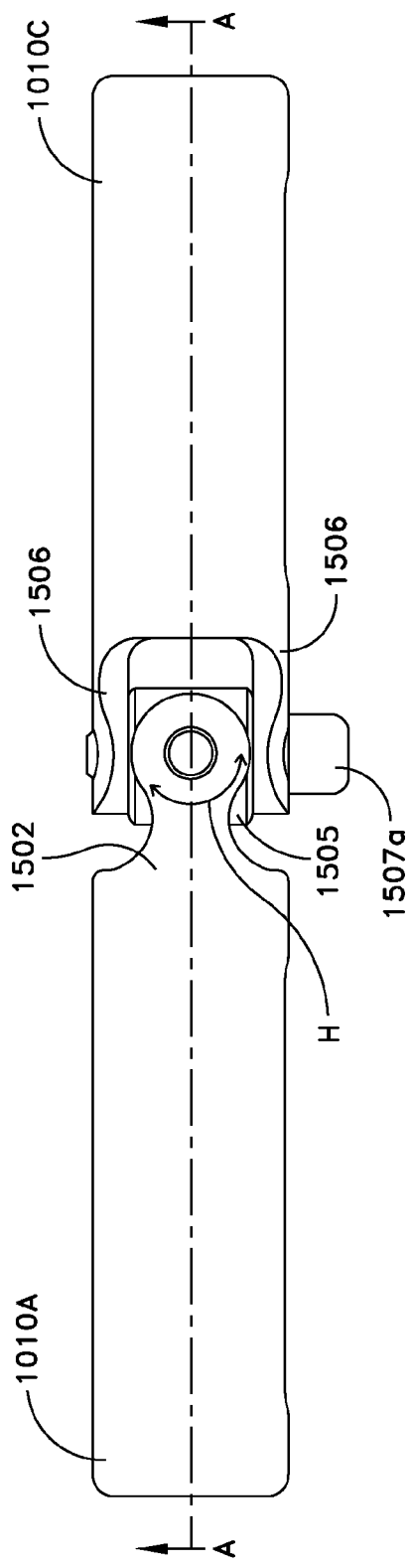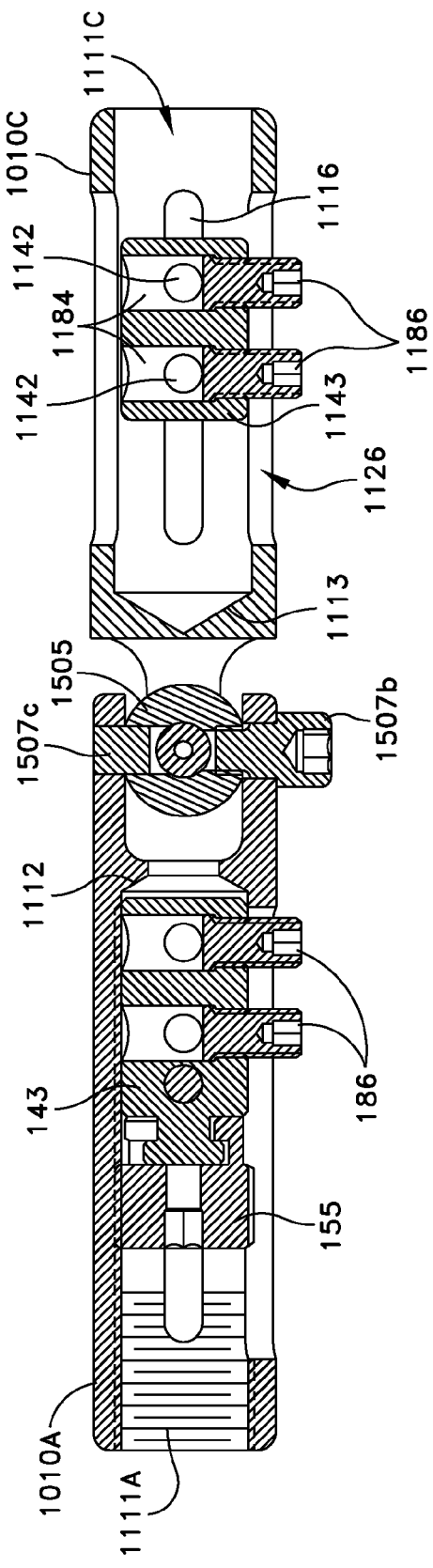
FIG. 10E
FIG. 10F

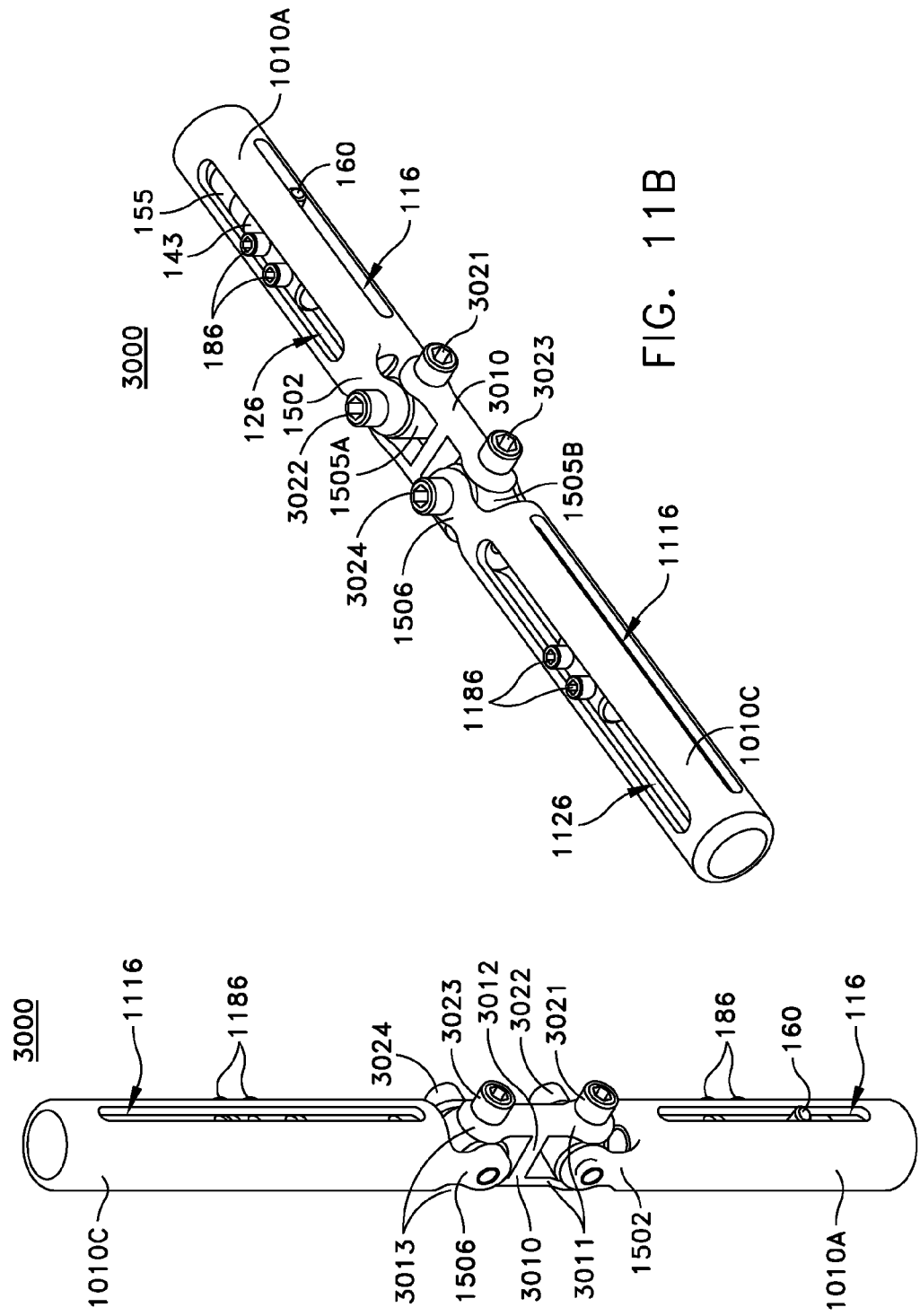

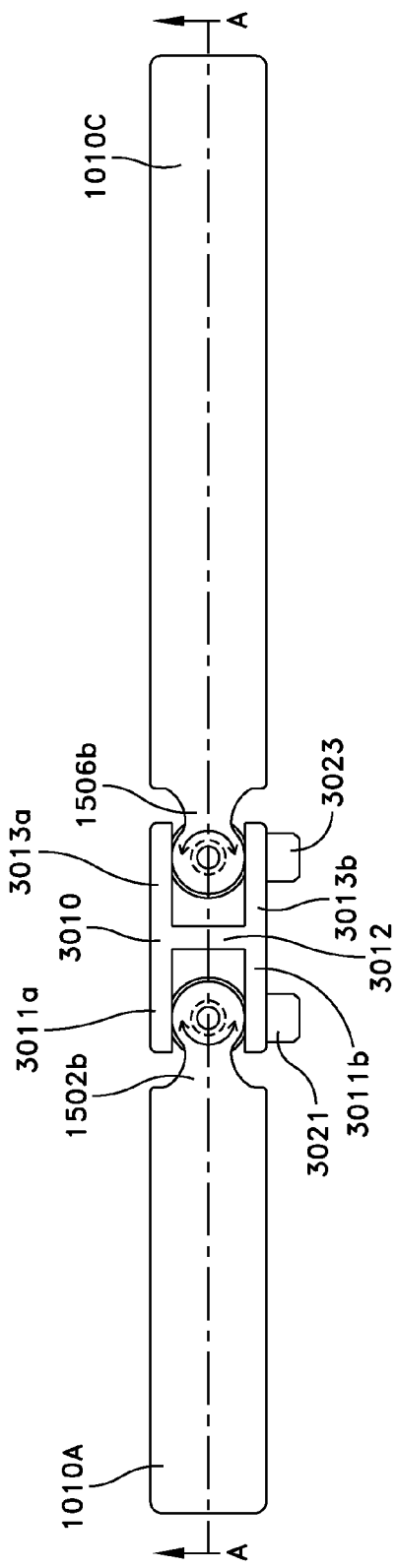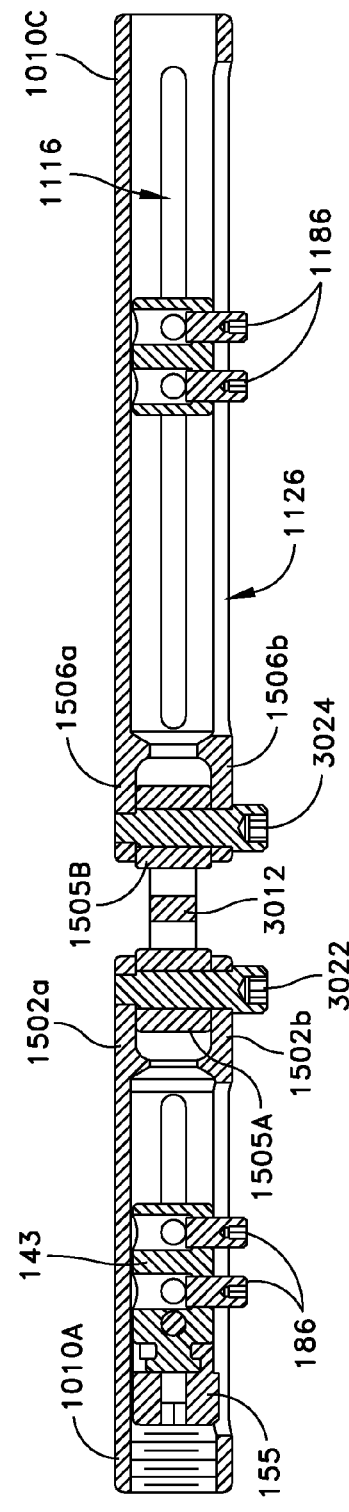
FIG. 11E
FIG. 11F

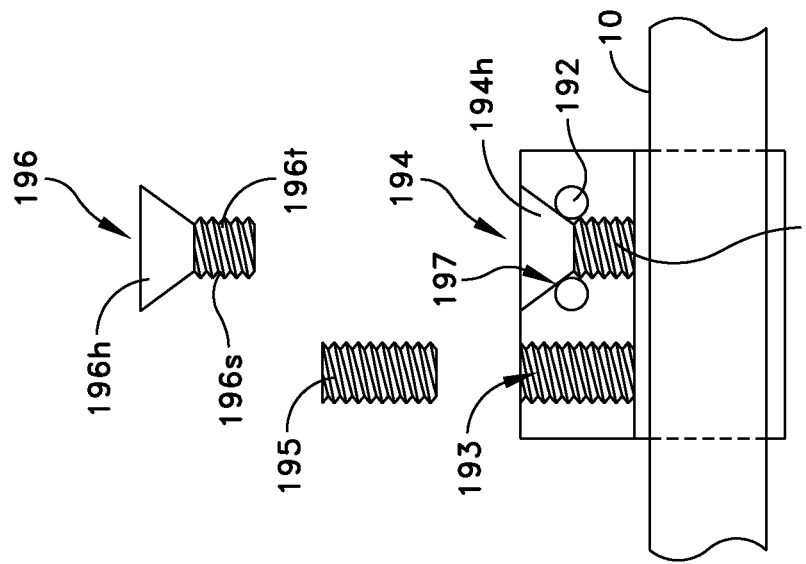
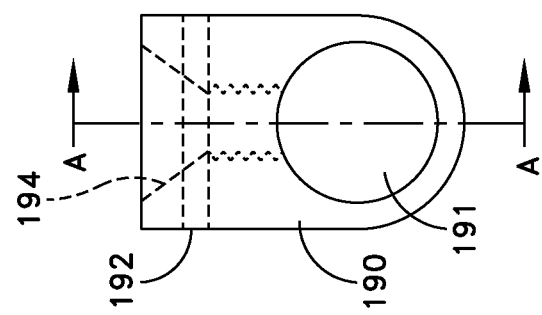
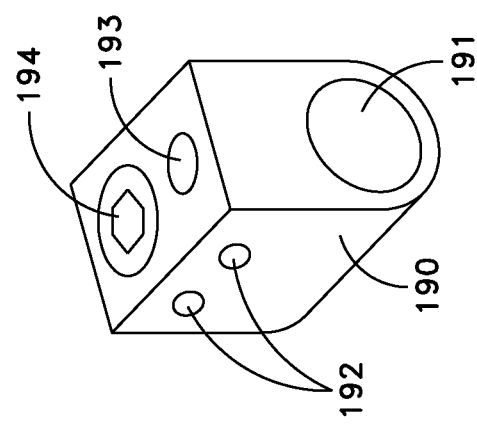
FIG. 20C
FIG. 20B
FIG. 20A

ORTHOPEDIC DEVICE

CROSS-REFERENCE TO RELATED APPLICATION

This application is a continuation application of a application U.S. Ser. No. 13/271,288, filed Oct. 12, 2011, now U.S. Pat. No. 8,585,702, which is a divisional application of U.S. Ser. No. 12/262,628, filed Oct. 31, 2008, now U.S. Pat. No. 8,057,473, which claims the benefit under 35 U.S.C. §119(e) of U.S. Provisional Application Ser. No. 60/984,012, filed Oct. 31, 2007, and U.S. Provisional Application Ser. No. 61/096,358, filed Sep. 12, 2008. The disclosures of the foregoing applications are incorporated herein by reference in their entirety.

FIELD OF THE INVENTION

The present disclosure relates to the field of orthopedics and more particularly to an external orthopedic device for providing fixation, reduction, or distraction of bone segments.

BACKGROUND

External orthopedic devices are used in many orthopedic treatments to fixate, distract, or reduce bone segments. Generally, fixation devices or fixators are used to stabilize bone pieces and to facilitate the healing of bones at a bone repair site. Such fixators can be used by orthopedic surgeons to restore the patient's anatomy at a fracture following an injury or distract an osteotomy site in bone lengthening procedures. Reduction and distraction devices are used to gradually adjust the relative orientation and spacing of the bone parts on opposing sides of a bone repair site. Because these external devices are attached externally to the patient's body for the duration of the treatment, which can last from several weeks to many months, the bulkiness of the external fixator devices are important features in the market acceptance of any particular design.

Thus, there is a continuing need for an improved external fixator that is adaptable to a variety of configurations while maintaining a low profile for physical compactness.

SUMMARY

According to an embodiment, an external fixator device for fixating bone parts is disclosed. Such device can be used in treating bone fractures or osteotomies. In treating bone fractures, the device can be used to hold the bone pieces in place. The device can be used for compression or distraction of the bone parts.

According to one embodiment, the orthopedic device comprises two sets of one or more bone fixation pins suitable for engaging a bone piece; a fixator body having a first part and a second part, the first and second parts being connected by a joint, the first part having an internally threaded bore extending longitudinally therethrough, the second part having a bore extending longitudinally therethrough; a first pair of opposed longitudinally extending slots in the first part of the fixator body; a first pin-holder received within and threadably engaging the internally threaded bore of the first part and configured to removably hold the first set of one or more bone fixation pins extending through the first pair of opposed longitudinally extending slots, the pin-holder longitudinally movable within the first part for controlling the position of the set of bone fixation pins within the first part; a second pair of opposed longitudinally extending slots in the second part of the fixator body; a second pin-holder received within the bore of the second part and configured to removably hold the second set of one or more bone fixation pins extending through the second pair of opposed longitudinally extending slots, the pin-holder longitudinally movable within the second part.

According to an embodiment, an orthopedic device for fixating bone parts includes a set of one or more bone fixation pins suitable for engaging a bone piece, an elongated fixator body having an internally threaded bore extending longitudinally therethrough, a pair of opposed longitudinally extending slots in the fixator body, and a pin-holder received within the fixator body and configured to removably hold the set of one or more bone fixation pins, the pin-holder longitudinally movable within the fixator body for controlling the position of the set of bone fixation pins within the fixator body. The orthopedic device can have the fixator body configured to removably hold a second set of one or more bone fixation pins at a location fixed along the fixator body.

According to another embodiment, an orthopedic device for fixating bone parts comprises a set of one or more bone fixation pins suitable for engaging a bone piece, a fixator body having an internally threaded bore extending longitudinally therethrough, a first pair of opposed longitudinally extending slots in the fixator body, and a pin-holder received within the internally threaded bore of the fixator body and configured to removably hold the set of one or more bone fixation pins extending through the pair of opposed longitudinally extending slots. The pin-holder is longitudinally movable within the fixator body for controlling the position of the set of bone fixation pins within the fixator body.

According to another embodiment, an orthopedic device for fixating bone parts comprises two sets of one or more bone fixation pins suitable for engaging a bone piece, a fixator body having a first part and a second part, and the first and second parts being connected by a joint. The joint can comprise a universal joint or double-jointed with two universal joints. Each of the first and second parts has an internally threaded bore extending longitudinally therethrough and a first pair of opposed longitudinally extending slots in the first part of the fixator body. A first pin-holder is received within the internally threaded bore of the first part and configured to removably hold the first set of one or more bone fixation pins extending through the first pair of opposed longitudinally extending slots. The pin-holder is longitudinally movable within the first part for controlling the position of the set of bone fixation pins within the first part. A second pair of opposed longitudinally extending slots are provided in the second part of the fixator body. A second pin-holder is received within the internally threaded bore of the second part and configured to removably hold the second set of one or more bone fixation pins extending through the second pair of opposed longitudinally extending slots, the pin-holder longitudinally movable within the second part.

According to another embodiment, a method of fixating two bones relative to one another is disclosed. The method comprises percutaneously placing a first fixation pin into a first bone piece, placing an external fixator over the first fixation pin by having the fixation pin go through a pin hole provided at one end of the external fixator's elongated body, wherein the elongated body has two ends and an internally threaded bore extending longitudinally therethrough. The elongated body's second end is then positioned over a second bone piece. A pin-holder configured to move longitudinally within the internally threaded bore and removably hold one or more fixation pins, is positioned along the length of the elongated body at a desired location over the second bone piece. Next, a second fixation pin is inserted through a pin hole provided in the pin-holder and into the second bone piece. Then, the second fixation pin is locked by tightening a set screw provided in the pin-holder are toxic. The first fixation pin is locked by tightening a locking set screw provided within and threadably engaging the internally threaded bore of the elongated body.

BRIEF DESCRIPTION OF THE DRAWINGS

FIG. 3A is a plan view of an external fixator according to another embodiment.

FIG. 3B is a sectional view of the universal joint of the external fixator of FIG. 3A taken through line A-A shown in FIG. 3A.

FIGS. 6A and 6B illustrate an application of the fixator of this disclosure in a spine.

FIGS. 7A-7C illustrate an application of the fixator of this disclosure in various long bone applications.

FIGS. 8A and 8B are perspective views of a fixator according to another embodiment.

FIGS. 9A-9H are various additional views of the fixator of FIGS. 8A and 8B.

FIGS. 10A and 10B are perspective views of a fixator according to another embodiment.

FIGS. 10C-10F are various additional views of the fixator of FIGS. 8A and 8B.

FIGS. 11A and 11B are perspective views of a fixator according to another embodiment.

FIGS. 11C-11F are various additional views of the fixator of FIGS. 8A and 8B.

FIG. 20A is an illustration of an offset pin clamp.

FIG. 20B is an end view of the offset pin clamp of FIG. 20A.

FIG. 20C is a longitudinal cross-section of the offset pin clamp of FIGS. 20A and 20B taken through the line A-A.

The features shown in the above referenced drawings are illustrated schematically and are not intended to be drawn to scale nor are they intended to be shown in precise positional relationship. Like reference numbers indicate like elements.

DETAILED DESCRIPTION

Figure 1A:
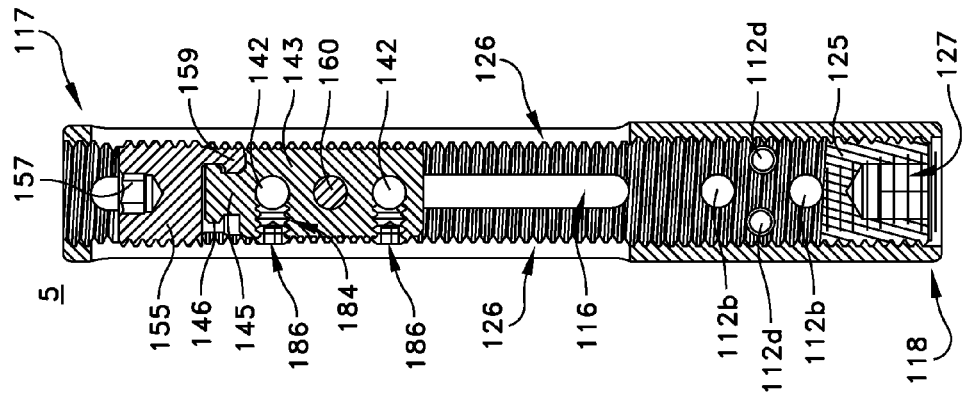
FIG. 1A is an illustration showing a perspective view of an external fixator according to another embodiment.

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Referring to FIGS. 1A-1E, an external fixator device 5 according to a preferred embodiment will be described. The external fixator device 5 includes a fixator body 110 having an internally threaded bore 111 extending longitudinally through the length of the fixator body 110. A pin-holder 143 is received in one end of the fixator body 110 and threadably engages the internally threaded bore 111 enabling the pin-holder 143 to move longitudinally inside the fixator body. The pin-holder 143 is provided with one or more pin holes 142 extending laterally through the pin-holder 143 for receiving a set of one or more bone fixation pins 5a. The lateral orientation of the pin holes 142 refer to the fact that the pin holes 142 extend through the pin-holder 143 generally sideways with respect to the longitudinal axis of the fixator body. The pin holes 142 can be oriented perpendicular to the longitudinal axis of the fixator body or at any desired angle. The fixator body can have cylindrical shape as shown in the illustrated example but the fixator body can have any appropriate shape.

As shown in FIG. 1A, two pairs of diametrically opposed longitudinally extending slots 116 and 126 are provided in the fixator body 110. The first pair of longitudinally extending slots 116 and the pin holes 142 provided in the pin-holder 143 allows one or more first set of fixation pins 5a (shown in phantom lines) to be removably received in the pin holes 142 and pass through the fixator body 110. The illustrated example is shown with two fixation pins 5a but the pin-holder 143 can be configured to accommodate as many fixation pins 5a as appropriate. The slots 116 allow the pin-holder 143 to be moved longitudinally within the fixator body 110 while holding the first set of fixation pins 5a. A guide pin 160 is provided in the pin-holder 143 to keep the pin-holder from rotating and keep the pin holes 142 aligned with the slots 116. The example of a guide pin 160 shown in FIG. 1A is a cylindrical pin but the pin is not limited to that shape and can be provided in any shape as long as it functions substantially the same way. The guide pin 160, for example, can have a square or hexagonal cross-sectional shape.

Figure 1B:
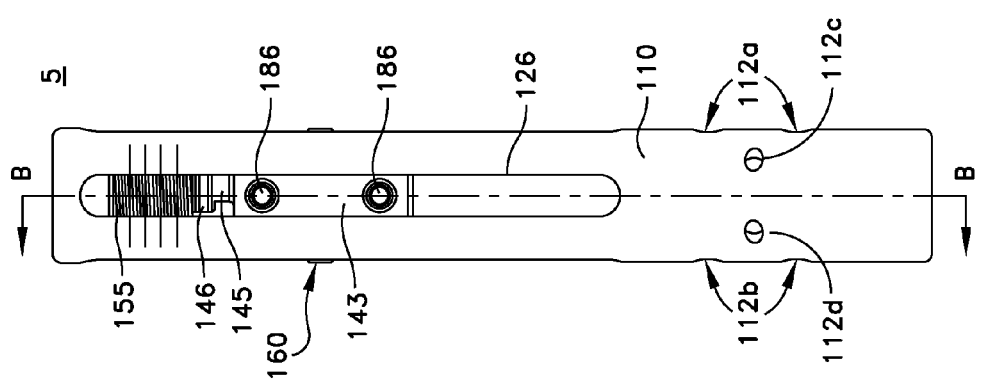
FIG. 1B is a plan view of the external fixator of FIG. 1A.
Figure 1C:
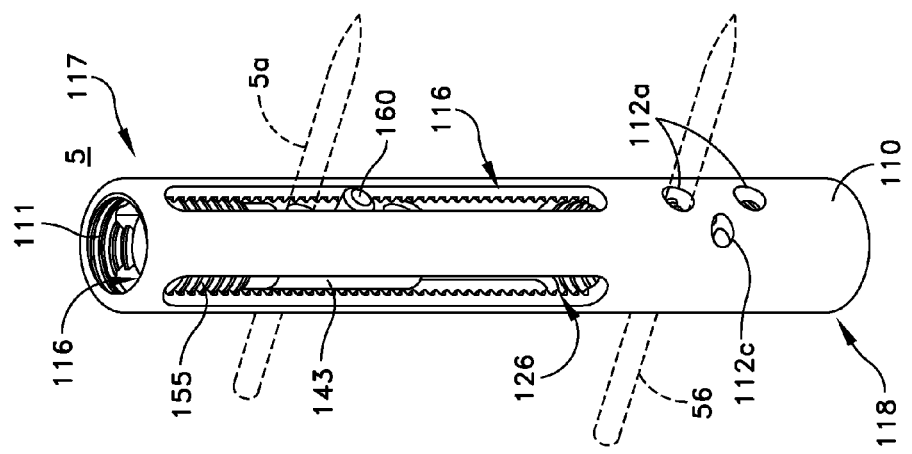
FIG. 1C is a cross-sectional view of the fixator of FIG. 1B taken through line B-B.
Figure 1E:
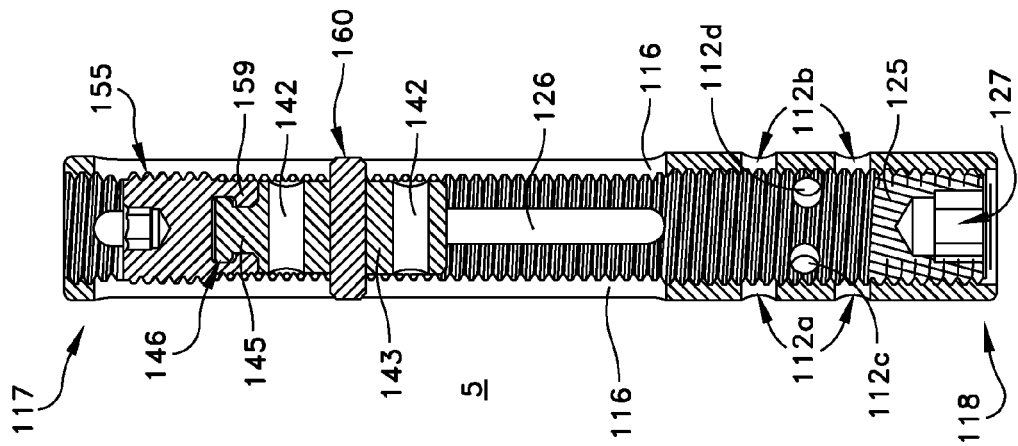
FIG. 1E is a cross-sectional view of the fixator of FIG. 1D taken through line A-A.
Figure 1D:
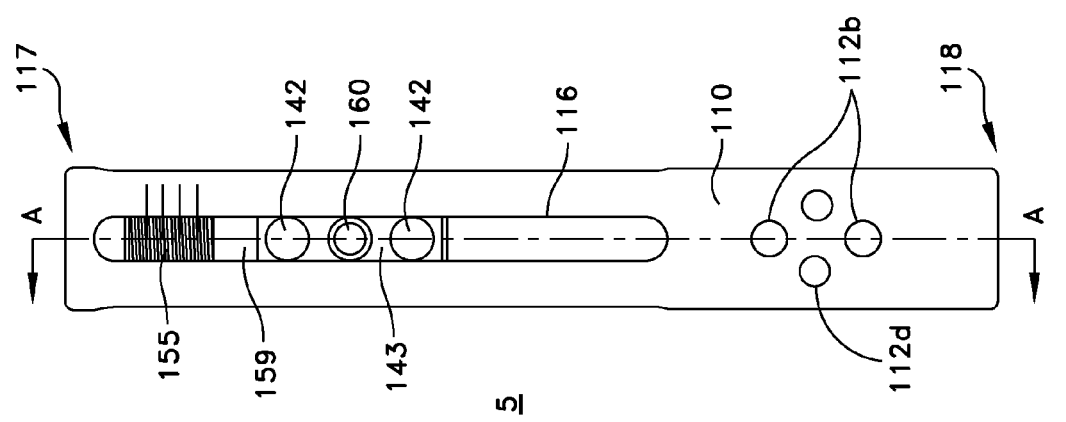
FIG. 1D is an opposite side plan view of the view shown in FIG. 1B.

Referring to the cross-sectional views shown in FIGS. 1C and 1E, the pin-holder 143 threadably engages the internally threaded bore 111 by means of a threaded driving screw 155. The driving screw 155 rotatably engages the pin-holder 143 and as the head portion is threaded in or out of the fixator body 110, it pushes or pulls the pin-holder 143 longitudinally within the bore 111.

The pin-holder assembly is inserted into the internally threaded bore 111 with the pin-holder 143 end first so that the threaded driving screw 155 is near the first end 117 of the fixator body 110 as shown in FIG. 1C. The driving screw 155 threadably engages the internally threaded bore 111 and operates on the pin-holder 143 to move the pin-holder 143 back and forth within the bore 111 in longitudinal direction. To enable this, the driving screw 155 and the pin-holder 143 are rotatably and axially coupled so that the threaded driving screw 155 can be rotated axially with respect to the pin-holder 143 while the pin-holder 143 is holding the fixation pins 5a. The driving screw 155 is provided with a socket 157 at the end opposite from the end rotatably coupled to the pin holder 143. The socket 157 is appropriately shaped to receive a tool for turning the driving screw 155.

The rotatable axial coupling between the driving screw 155 and the pin-holder 143 can be achieved in a variety of ways. In one embodiment, this rotatable axial coupling is achieved by the exemplary structures shown in FIG. 1C. In this example, the pin-holder 143 has a center stem 145 that extends into the threaded driving screw 155. The center stem 145 has a flared head portion 146 having a larger diameter than the center stem 145. The center stem 145 including the head portion 146 is received in a recess of the driving screw 155 defined by a longitudinally extending flange 159. The flared head portion 146 interferes with a portion of the flange 159 so that the pin-holder 143 and the driving screw 155 are secured together in longitudinal direction while allowing the pieces to rotate with respect to each other.

The flange 159 extends partially along the periphery of the driving screw 155 leaving an opening so that the driving screw 155 and the pin-holder 143 can be assembled by sliding the center stem 145 through the opening into the recess. As mentioned earlier, however, the rotatable coupling structure between the pin-holder 143 and the driving screw 155 is not limited to the configuration discussed. For example, the coupling structure shown in FIG. 1C can be reversed so that the center stem 145 is provided on the driving screw 155 and the longitudinally extending flange 159 is provided on the pin-holder 143. Furthermore, the head portion 146 of the center stem 145 can have a spherical shape rather than the flat shape illustrated in FIGS. 1C and 1E.

As shown in FIG. 1C, set screws 186 are provided in the pin-holder 143 for locking the first set of fixation pins 5a in their corresponding pin holes 142. The pin-holder 143 is provided with at least one threaded bore 184 for each pin hole 142 for receiving a set screw 186. Each of the set screws 186 threads into the threaded bore 184 corresponding to a pin hole 142 and secures a bone fixation pin that is received in the pin hole 142 by impinging against the bone fixation pin.

In the illustrated example, the threaded bores 184 are aligned with the second set of slots 126 so that the set screws 186 are accessible through the slots 126 for tightening or loosening. According to an aspect of the invention, the threaded bores 184 can extend completely through the opposite side of the pin-holder 143 so that set screws 186 can be threaded in to the pin-holder 143 from either side through either one of the second set of slots 126. According to another aspect of the invention, some of the pin holes 142 in the pin-holder 143 can be oriented to align with the first set of slots 116 and other pin holes 142 can be oriented to align with the second set of slots 126. The pin-holder 143 can be provided with one or more pin holes 142, the specific number depending on the maximum number of fixation pins 5a the particular fixator device requires.

Figure 2A:
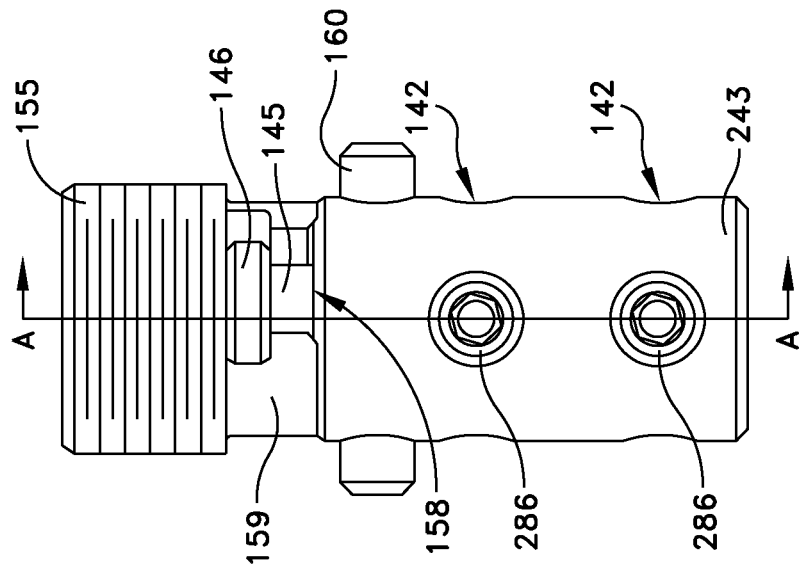
FIG. 2A is a plan view of an embodiment of a pin holder assembly.
Figure 2B:
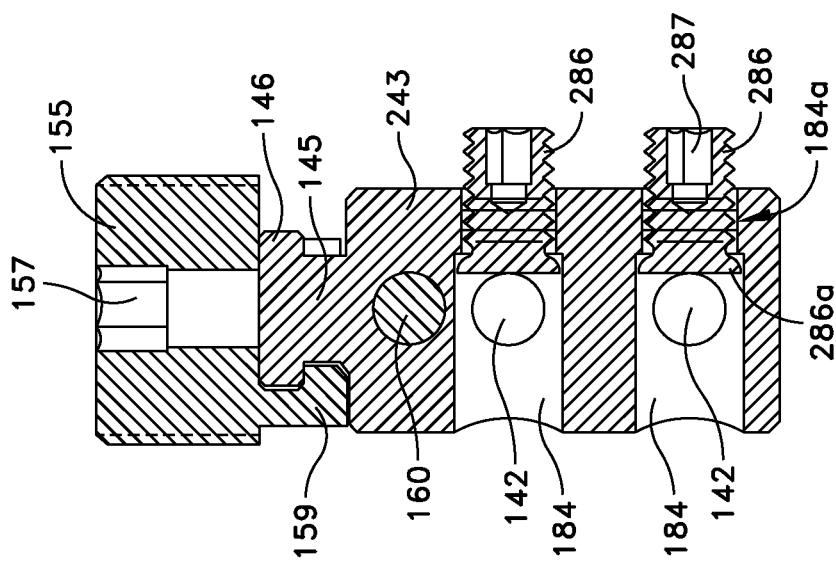
FIG. 2B is a cross-sectional view of the pin holder assembly of FIG. 2A taken through line A-A shown in FIG. 2A.

FIGS. 2A and 2B shows a pin-holder 243 according to another embodiment. The pin-holder 243 is also configured to rotatably couple to a driving screw 155. Similar to the pin-holder 143, the pin-holder 243 is also configured with a center stem 145 that is received into the recess in the driving screw 155 formed by the longitudinally extending flange 159. The center stem 145 of the pin-holder 243 has a flared head portion 146 that interferes with a portion of the flange 159 when they are coupled so that the pin-holder 243 and the driving screw 155 are secured together in longitudinal direction while they can rotate with respect to each other. As discussed above, this coupling structure is only one example and other suitable coupling structure can be used.

As shown in FIGS. 2A and 2B, the flange 159 extends partially along the periphery of the driving screw 155 leaving an opening 158 so that the driving screw 155 and the pin-holder 243 can be assembled by sliding the center stem 145 through the opening 158 into the recess.

The pin-holder 243 illustrates an embodiment wherein the relative positions of the pin holes 142 and the guide pin 160 are different from those of the pin-holder 143. In the pin-holder 243, one or more pin holes 142 are positioned on one side of the guide pin 160 so that the pin holes 142 can be positioned closer together. The positions of the threaded bores 184 for the set screws 286 are aligned with the pin holes so that the set screws 286 can lock the first set of fixation pins 5a received in the pin holes 142. In this embodiment, the threaded bores 184 extend completely through the pin-holder 243 and actually only one end 184a of a bore 184 is threaded to threadably engage the set screws 286. The set screws 286 are inserted into their respective bore 184 from the non-threaded end. The set screws 286 are provided with a socket 287 at one end appropriately shaped for receiving a tool for turning the set screws. Thus, the socket end 287 extends out as shown in FIG. 2B. The opposite end, the end that will be urged against a fixation pin received in the pin hole 142, of the set screws 286 have a flared portion 286a whose diameter is larger than the diameter of the threaded portion 184a of the bore 184 functioning as a stop and prevents the set screws 286 from being completely removed through the threaded end 184a. This feature allows the end user to loosen or unscrewing the set screws 286 without worrying about the set screws 286 falling out of the pin-holder 243 while unscrewing.

The fixator body 110 may be provided with at least one pair of opposed pin holes 112a and 12b near the fixator body's second end 118 for receiving one or more second set of fixation pins 5b (shown in phantom lines in FIG. 1A) through the fixator body. Similar to the pin holes 12 provided in the embodiment of FIG. 13A, for example, a pair of opposed pin holes 112 are provided for each of the fixation pins 5b. The pin holes for receiving the second set of fixation pins 5b can be diametrically (with respect to the diameter of the fixator body 110) opposed like the pin holes 112a and 112b or they can be off-set from the diameter of the fixator body 110 like the pair of pin holes 112c and 112d shown in FIGS. 1A and 1B. Regardless, the fixator body 110 can be provided with as many sets of such pin holes as many second set of fixation pins 5b are necessary. Furthermore, the pin holes 112a, 112b, 112c and 112d can be positioned so that the second set of fixation pins 5b can be at any desired angle with respect to the longitudinal axis of the fixator body 110.

At the second end 118 of the fixator body 110, a locking set screw 125 is received in and threadably engages the internally threaded bore 111 of the fixator body for locking the second fixation pins 5b. The manner in which the second fixation pins 5b cooperates with the rest of the external fixator device 5 is similar to that described in connection with the embodiment of the external fixator device 1 described above. The locking set screw 125 is provided with a socket 127 appropriately shaped to receive a tool for turning the set screw 125.

FIG. 3A shows another embodiment of the external fixator 5 of FIGS. 1A-1E. In this embodiment, the fixator body 110 is configured with a universal joint 500 between two portions 110A and 110B of the fixator body 110. The universal joint allows the two portions 110A and 110B of the fixator body to be set at any desired angle, which in turn allows the fixation pins held in each of the two portions 110A and 110B of the external fixator. The universal joint is formed by hinge legs 502 and 504 of the two portions 110A and 110B, respectively, joined by a double-axle 505, which is a typical universal joint construction. The double-axle 505 can be configured to allow locking of the universal joint at a desired angle. FIG. 3B, a cross-section of the universal joint taken through the line A-A shown in FIG. 3A, shows that the double-axle 505 can include a locking screw 507a and 507b for each of the two axes of the universal joint. The locking screws 507a and 507b threads into the main body of the double-axle 505 and locks the universal joint 505 in each of the two axes by compressing the respective hinge legs 504 and 502.

Figure 3C:
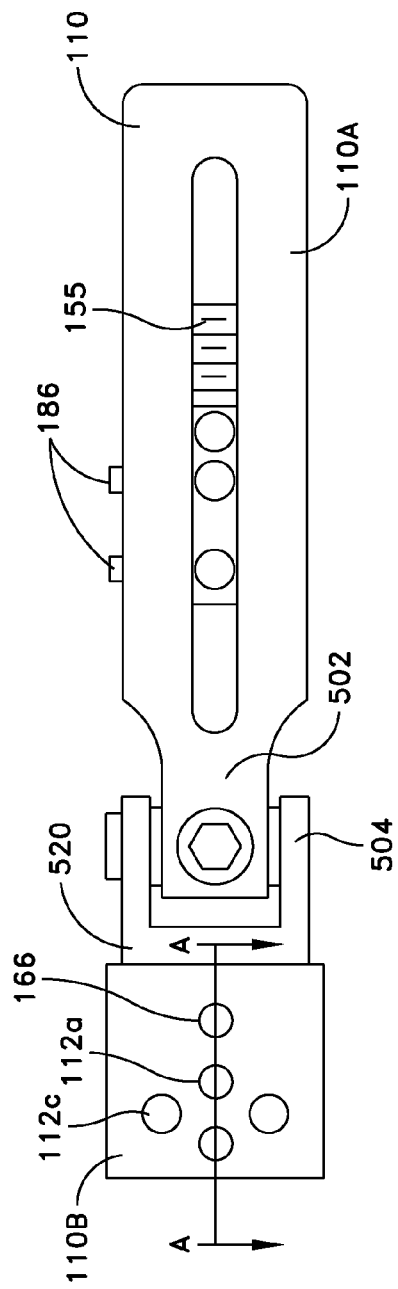
FIG. 3C is a plan view of an external fixator according to another embodiment.
Figure 3D:
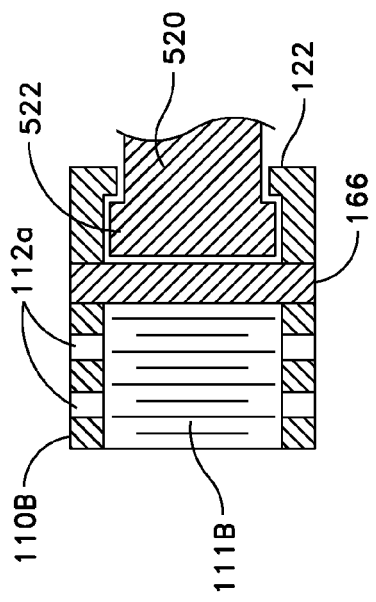
FIGS. 3D and 3E are longitudinal sectional views taken through line B-B shown in FIG. 3D illustration two embodiments of a portion of the external fixator of FIG. 3C.
Figure 3E:
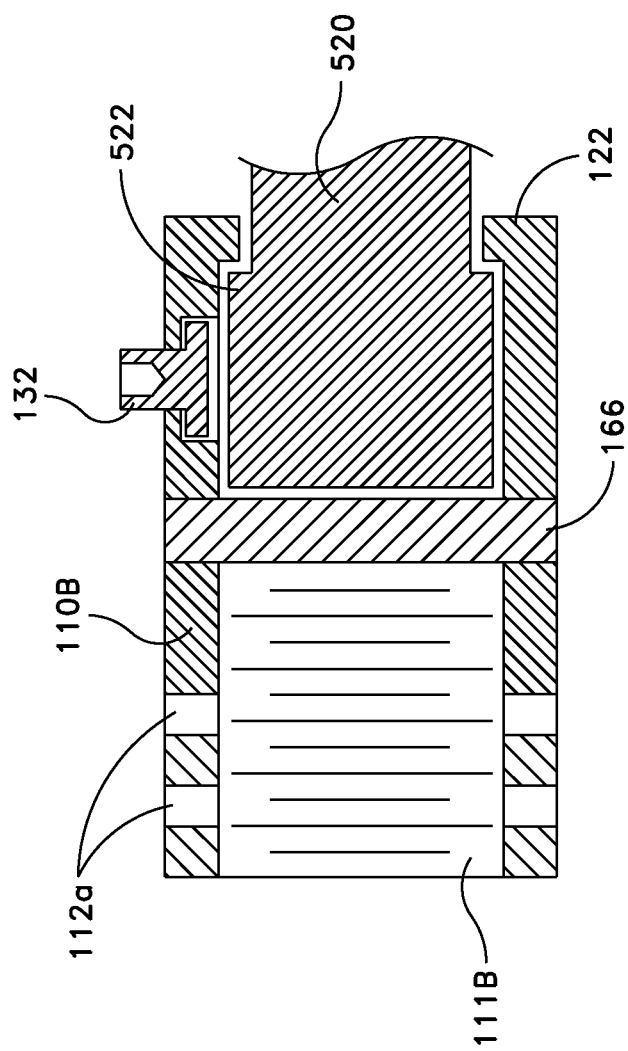

FIG. 3C shows another embodiment wherein the second portion 110B of the fixator body is configured to freely rotate axially with respect to the universal joint body 520. FIG. 3D, which is a longitudinal sectional view of the second portion 110B of the fixator body taken through the line B-B of FIG. 3C, shows an example of that structure that allows the free axial rotation of the second portion 110B. One end of the universal joint body 520 is received within the threaded bore 111B of the second portion 110B. The universal joint body 520 and the second portion 110B have flanges 522 and 122, respectively, which interfere with one another to keep the universal joint body 520 from being pulled out of the second portion 110B when the fixator 5 is used in distraction mode. On the other hand, a retaining pin 166 inserted across the second portion 110B prevents the universal joint body 520 from being pushed into the second portion 110B when the fixator 5 is used in compression mode. FIG. 3E shows an embodiment where a set screw 132 for locking the free-spinning universal joint body 520 is provided in the second portion 110B of the fixator body. The set screw 132 threadably engages the second portion 110B and advances inward urging against the flange portion 522 of the universal joint body 520 to lock the universal joint body 520.

Figure 4A:
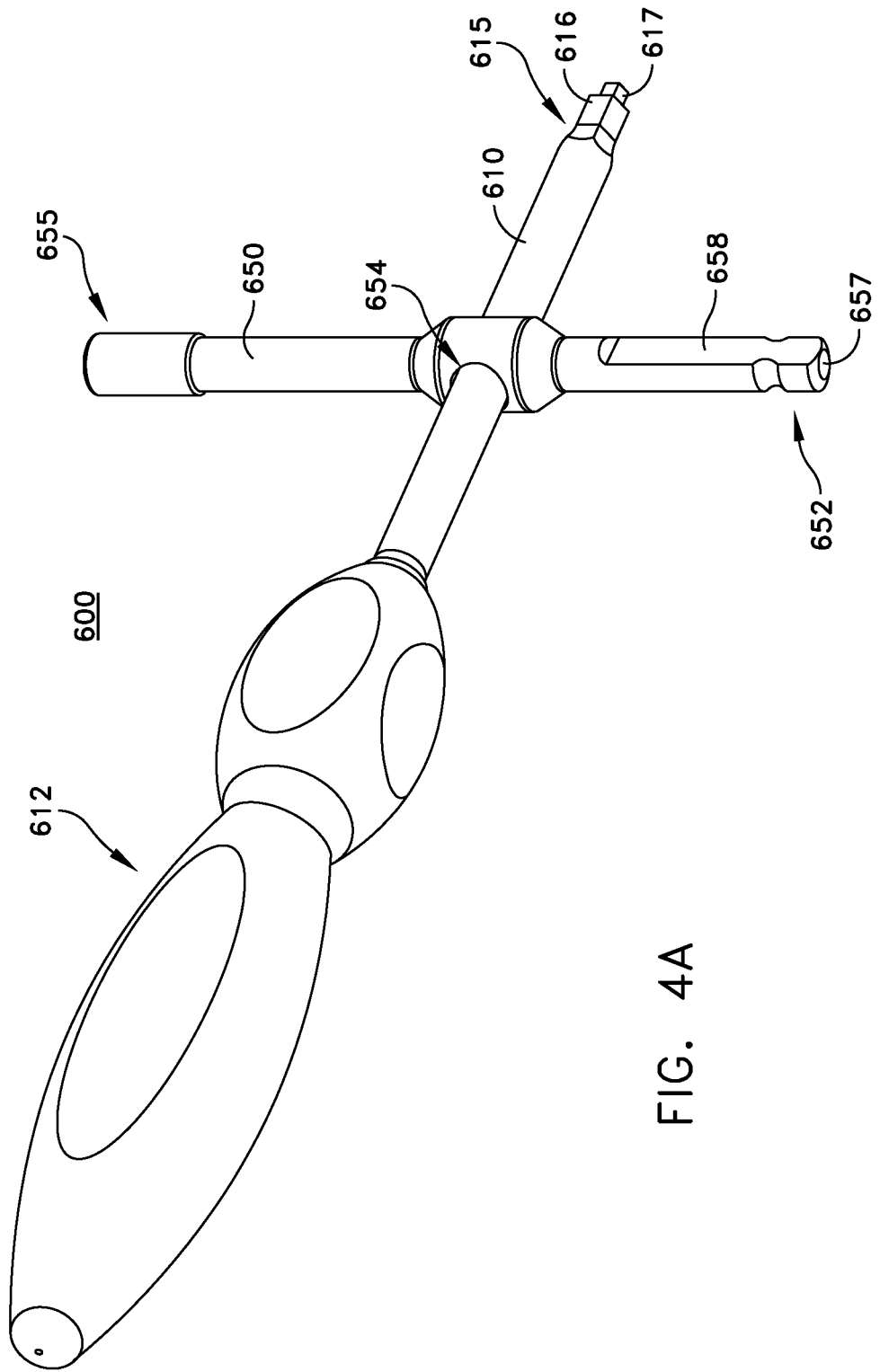
FIGS. 4A-4C illustrate a hand tool set for use with the external fixator of this disclosure.
Figure 4B:
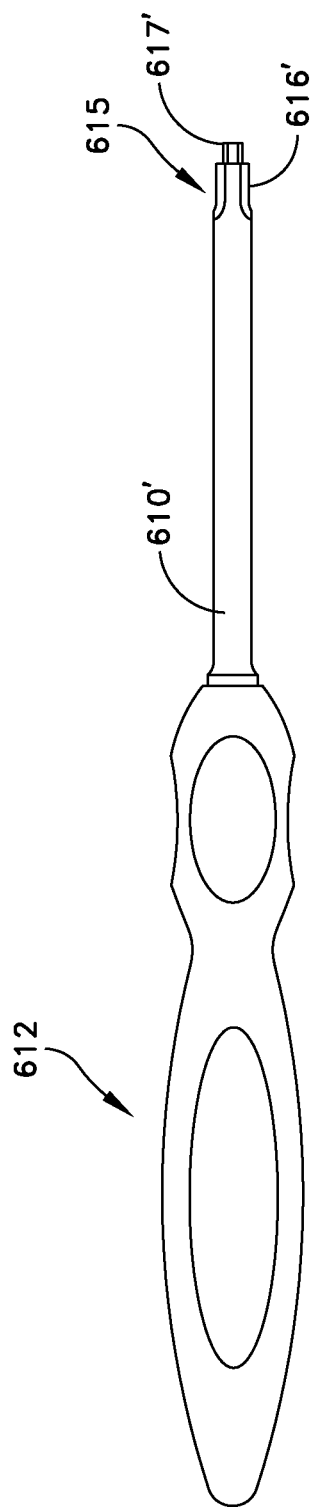

FIG. 4A shows a hand tool set 600 that can be provided along with the external fixator device of this disclosure. The hand tool set 600 includes a screwdriver 610 and an adaptor 650. The screwdriver 610 is for the user of the external fixator device such as a surgeon to tighten or loosen the various set screws that are used in the external fixator device. The driver includes a handle portion 612 and a driving tip 615 (i.e. the part that engages the set screws). The driving tip 615 is configured and adapted appropriately for engaging the set screw. For example, the driving tip 615 is shown in FIG. 4B with a square tip 616 for driving a Robertson-type screw heads. This example of a screwdriver 610 is double-tipped and includes a second driving tip 617 which is a smaller square tip. Thus, the user can use this one screwdriver 610 for driving two different size screw heads.

In the external fixator embodiment of FIGS. 1A-1C, for example, the screwdriver 610 can be appropriately configured and adapted to engage the sockets of the set screws 125, 155, and 186. As discussed above, the set screws can have any one of the variety of driver socket shapes and the screwdriver 610 would be configured with an appropriately matching driving tip 615.

As an example, FIG. 4B shows another embodiment of the screw driver 610' having a driving tip 615 configured as a double-hex tip. The driving tip 615 is configured with two different size hex driving tips 616' and 617'.

The adaptor 650 is configured to be used for driving bone fixation pins into a bone piece and for removing the bone fixation pins. The adaptor 650 is provided with a screwdriver connector end 652 at one end and a bone fixation pin engaging end 655 at the other end. The fixation pin engaging end 655 is provided with a socket appropriately shaped to receive the distal end of a bone fixation pin. If the distal end of the bone fixation pin has a square shaped tip, as many fixation pins do, the fixation pin engaging end 655 will be provided with a square shaped socket.

Figure 4C:
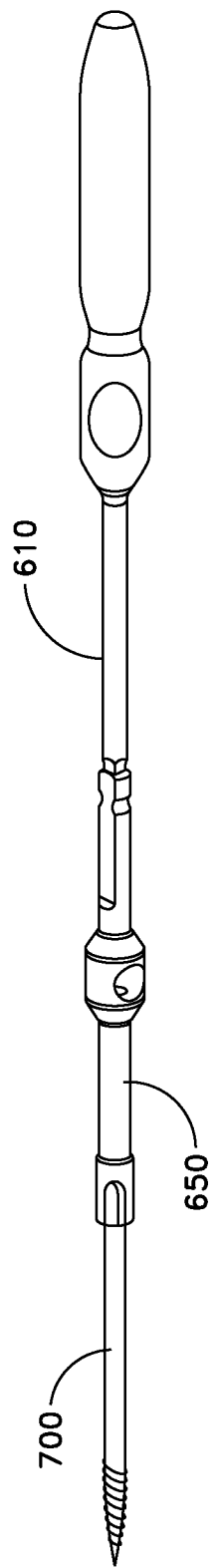

The screwdriver connector end 652 is configured and adapted appropriately for engaging a particular screw driver or a power driver that may be used to drive or remove the bone fixation pins. In the example shown in FIG. 4A, the screwdriver connector end 652 is provided with a square-shaped socket 657 for receiving the square-shaped screwdriver tip 617. FIG. 4C shows a bone fixation pin 700 engaged with the adaptor 650 and the adaptor 650 in turn being driven by the screwdriver 610.

According to another embodiment, the screwdriver connector end 652 of the adaptor 650 is configured to be engaged to a power screwdriver's chuck. In the example shown in FIG. 4A, the screwdriver connector end 652 is provided with a flat surface 658 that is required for engaging with a particular type of power screwdriver chuck that is in use in the industry.

The adaptor can also be provided with a hole 654 for receiving the screw driver 610 as shown in FIG. 4A to provide more leverage when the bone fixation pins are manually being driven. This arrangement provides more torque than the arrangement shown in FIG. 4C.

Figure 5A:
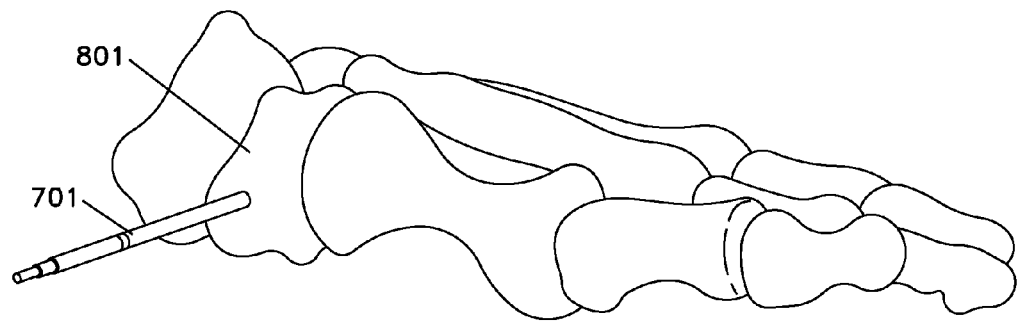
FIGS. 5A-5H illustrate a method of using an embodiment of the fixator of this disclosure to fixate two bones in a foot.
Figure 5B:
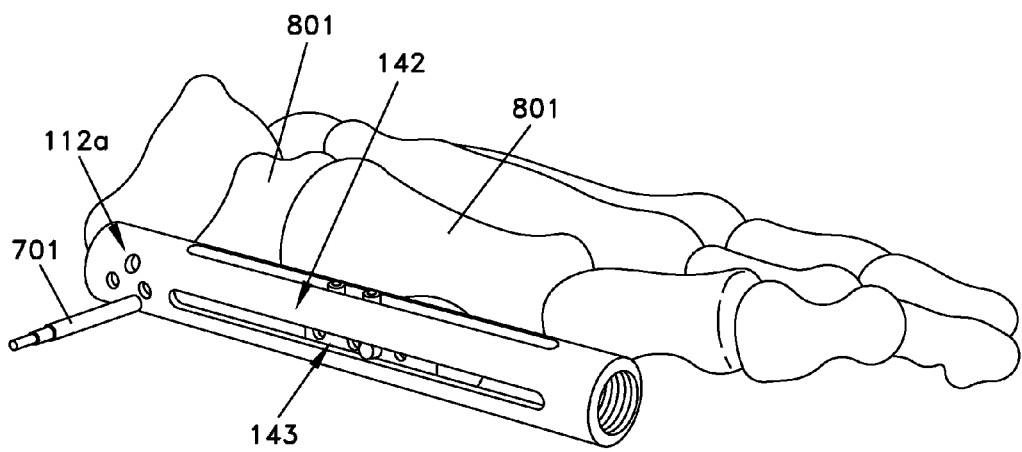

A method of using an embodiment of the external fixator device to fixate two bones in a foot will be described as an example of methods for using the external fixator of this disclosure. Referring to FIG. 5A, the threaded end of a first fixation pin 701 is placed freehand perpendicular to the long axis of the bone 801. FIGS. 5A-5H are illustrated using a skeletal model of a foot but in actual use the fixation pins will be driven into the bone percutaneously. The fixation pin diameter should not exceed ⅓ of the bone diameter. Referring to FIG. 5B, the external fixator 5 of FIGS. 1A-1E is placed over the first fixation pin 701 (the fixation pin going through one of the pin hole 112a) and aligned so that the distally located pin-holder 143 of the fixator 5 is positioned over the second bone 802. The pin-holder 143 should be adjusted along the length of the fixator 5 to position the pin holes 142 (see FIG. 1C for the pin holes 142 in the pin-holder 143) in the desired location.

Figure 5C:
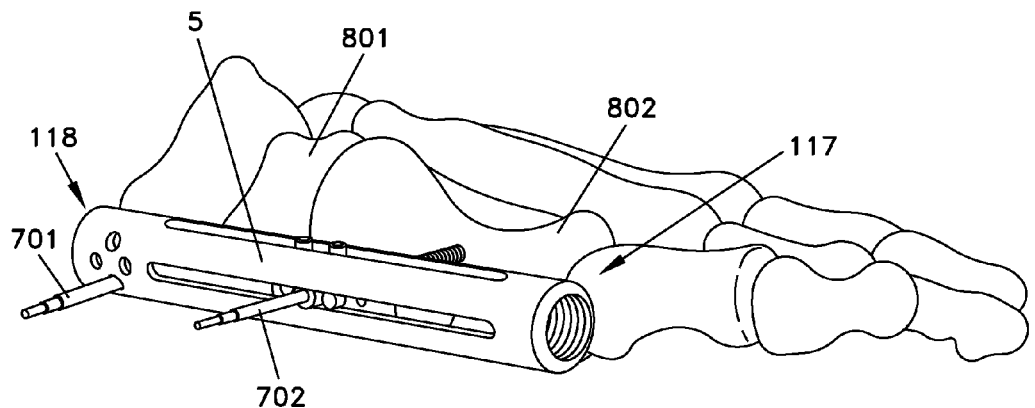

Referring to FIG. 5C, a second fixation pin 702 is inserted through one of the pin holes 142 and into the second bone 802. During this step, the pin-holder 143 functions as a guide for threading the second fixation pin 702 into the second bone 802. At this point, fluoroscopy can be used to check penetration of the pins 701 and 702 through the far cortex of the bone. Pins should not penetrate more than 2 mm beyond the far cortex of bone.

Figure 5D:
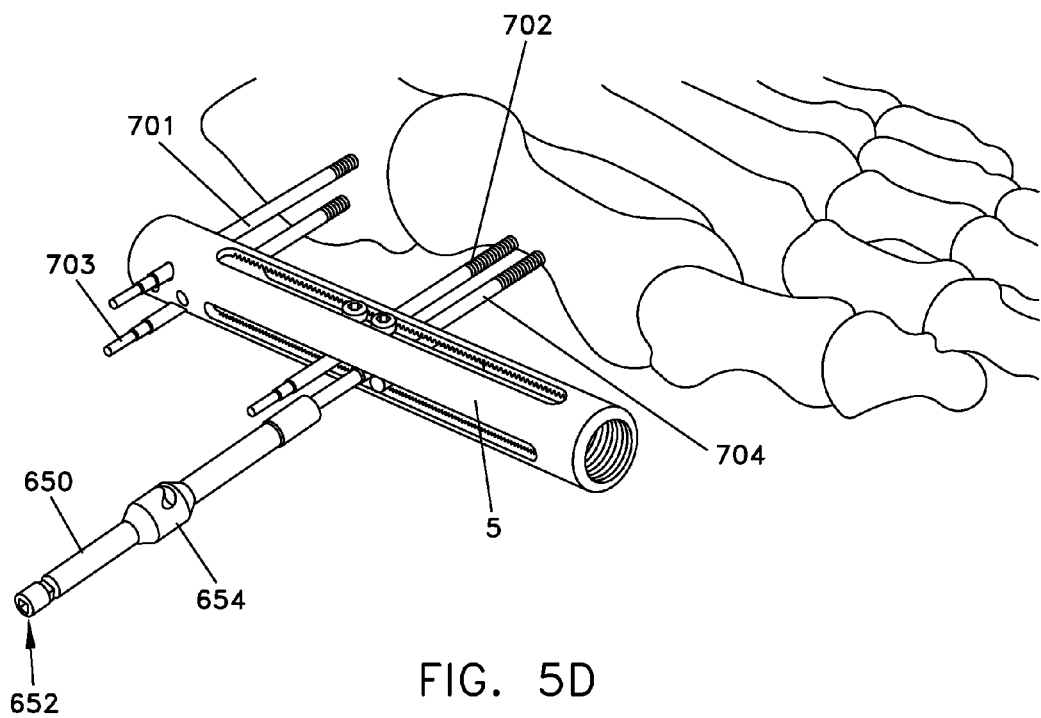
Figure 5E:
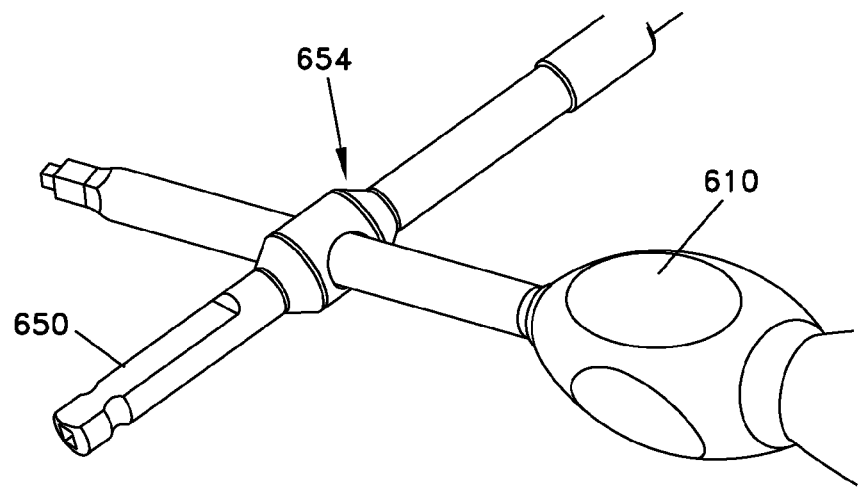

Referring to FIG. 5D, a third and fourth fixation pins 703 and 704 are inserted through the fixator 5 in the same manner as the first two fixation pins and threaded into the first and second bone pieces 801 and 801, respectively. The screw driver adaptor 650 of FIG. 4A can be used to connect to the pins to assist with the insertion. As discussed above in connection with FIGS. 4A-4C, a screw driver 610 can be connected to the screwdriver connector end 652 of the adaptor 650 to manually advance the fixation pins into the bone. If more torque is required, the screw driver 610 can be inserted through the hole 654 as shown in FIG. 5E to advance the fixation pins.

The fixator 5 provides at least two sets of pin holes 112a and 112c at the proximal end 118 so that the proximal pins 701, 703 can be positioned in either a vertical or horizontal configuration. Adequate clearance should be left between the fixator 5 and the patient's skin to allow for post-operative swelling.

Figure 5F:
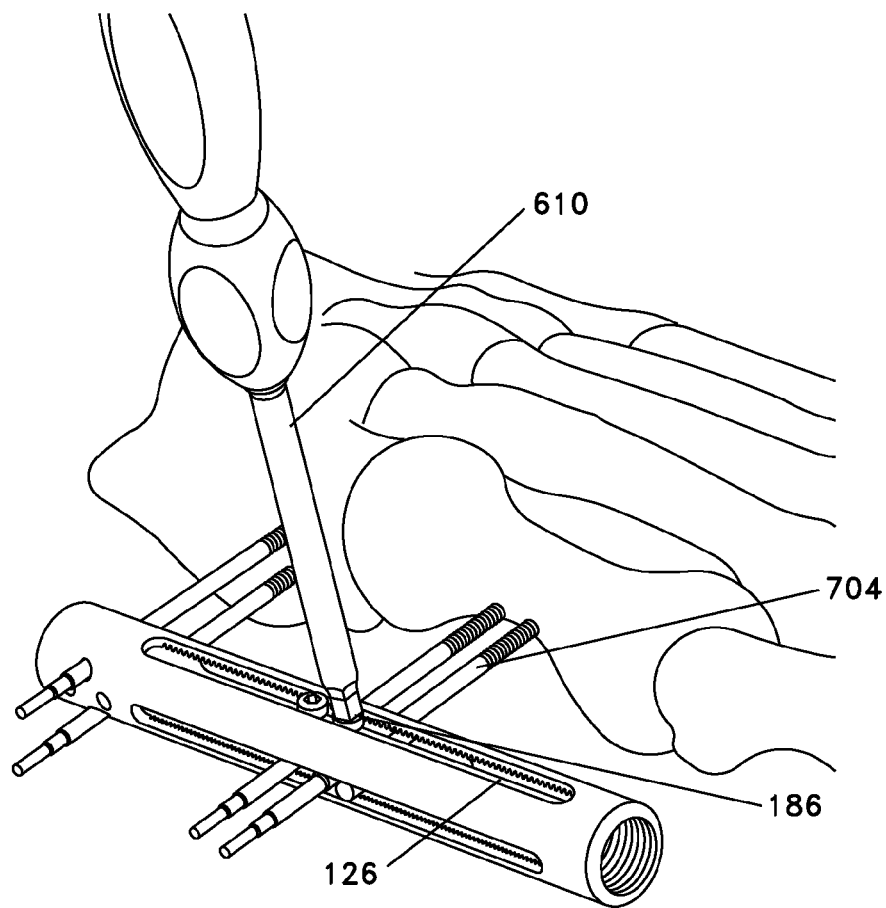
Figure 5G:
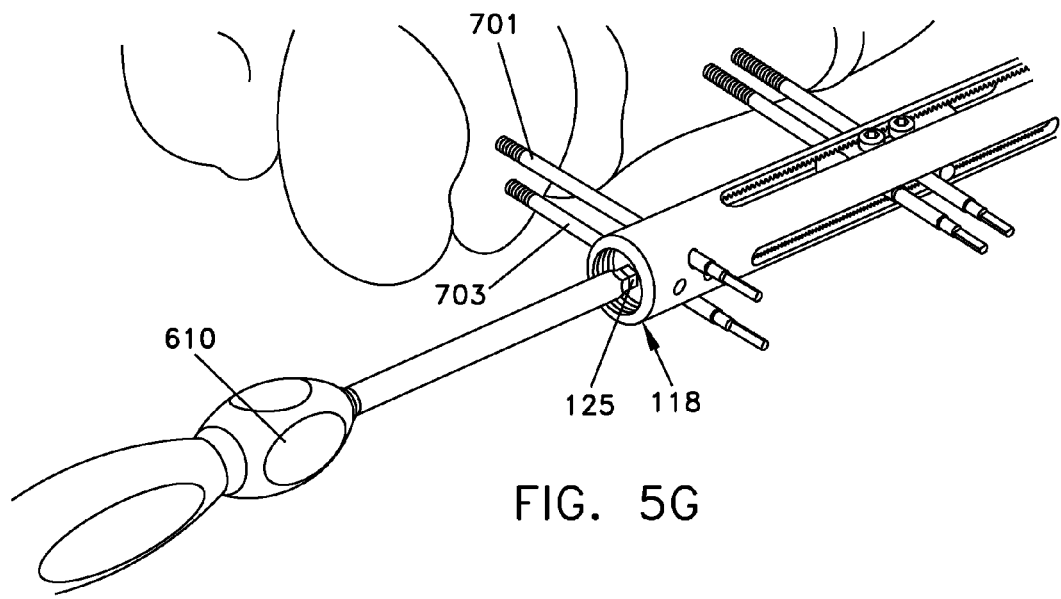
Figure 5H:
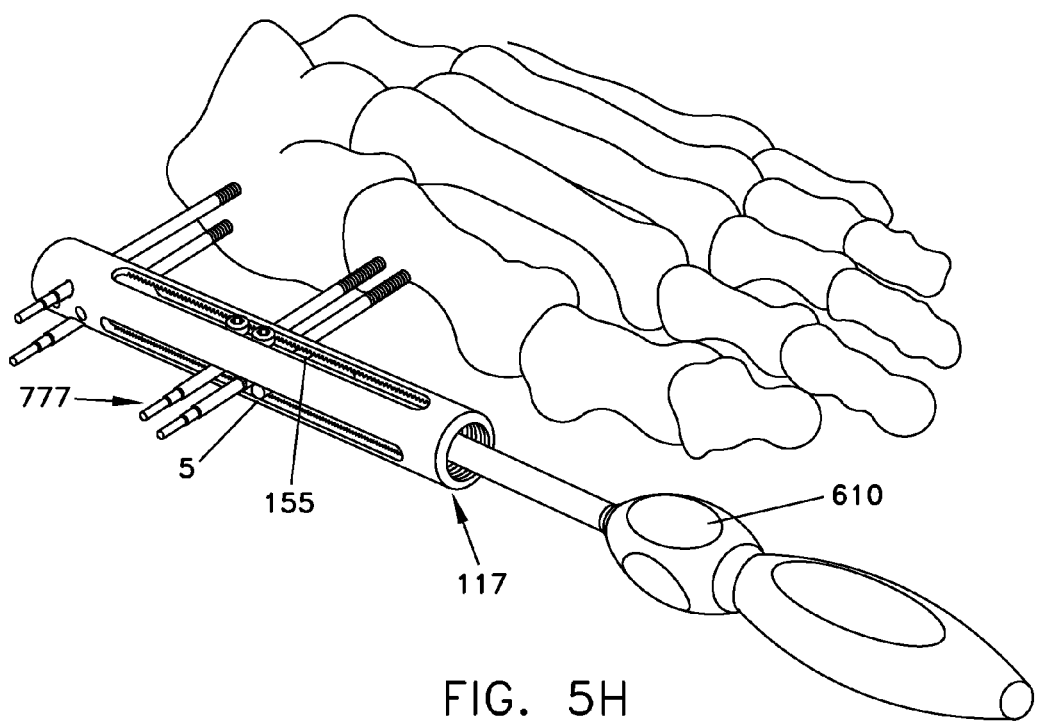
Figure 11C:
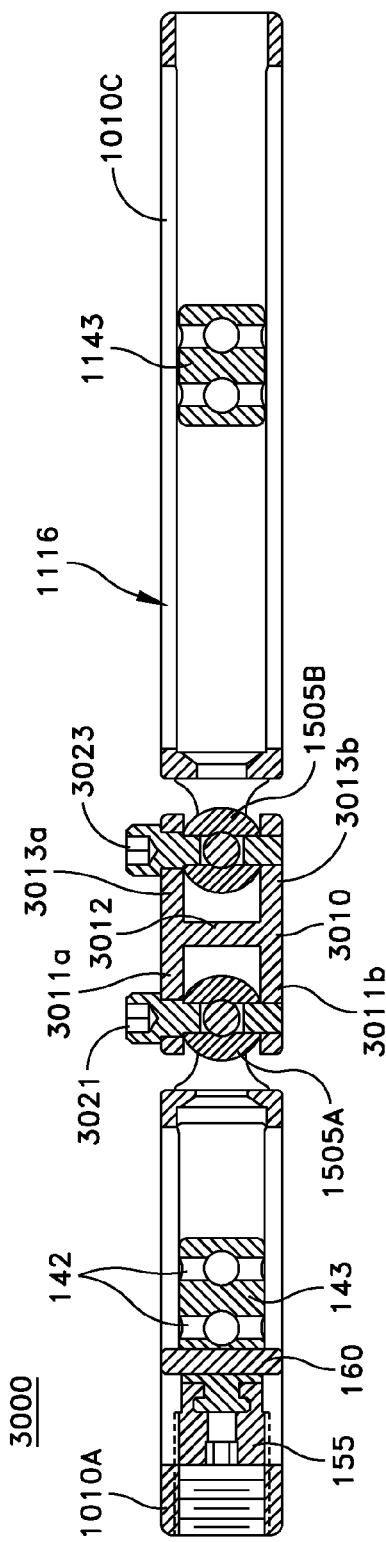
Figure 11D:
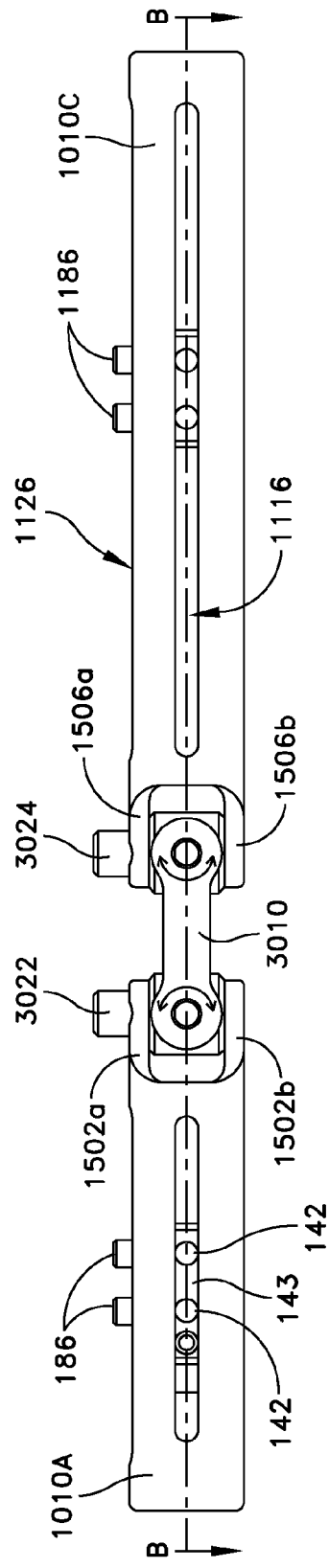

Referring to FIG. 5F, the distal pins 702, 704 are locked by tightening the set screws 186 of the pin-holder 143 located within and accessible through the fixator's slot 126. Referring to FIG. 5G, the proximal fixation pins 701, 703 are locked by tightening the locking set screw 125 located in the threaded bore of the fixator 5 in the proximal end 118 of the fixator 5. Referring to FIG. 5H, compression or distraction can be obtained by turning the driving screw 155 of the pin-holder 143 located within the threaded bore of the fixator 5 accessible from the distal end 117 of the fixator. For compression, the driving screw 155 is turned in the direction that will move the pin-holder 143, and thus the distal fixation pins 702, 704, towards the proximal pins 701, 703. The direction of the turn will depend on the thread direction of the threaded bore of the fixator 5. For distraction, the driving screw 155 is turned in the opposite direction moving the pin-holder 143, and thus the distal fixation pins 702, 704, away from the proximal fixation pins 701, 703. For bone lengthening with a callotasis technique, for example, the distraction can be divided into ¼ turn increments where the threads on the internal bore of the fixator 5 is configured so that one full turn of the screwdriver will result in 1 mm of distraction. After the fixator 5 is applied, the protruding ends 777 of the fixation pins should be cut short and capped with pin covers (not shown) or if possible, the fixator pin-holder 143 can be temporarily loosened so that the fixator 5 can be moved slightly away from the body to cover the cut ends of the fixation pins. Perform a final check of all fixator components to ensure that they are tightened before completing the surgery.

The various embodiments of the external fixator device described herein can be used in treating other bones. For example, FIGS. 6A and 6B shows a fixator device such as the embodiment 5 of FIGS. 1A-1E, being used in a spine application. FIGS. 6A and 6B show two such fixator devices 5 percutaneously attached to two vertebrae 901 and 902. The fixators 5 can be used to fuse or decompress the vertebra 901, 902. FIGS. 7A-7C show more examples where the fixator devices 5 are used in fixating or lengthening of various long bones. FIG. 7A shows the fixators 5 attached to an ulna 903 and a radius 904. FIG. 7B shows the fixators 5 attached to a femur 905 and a tibia 906. FIG. 7C shows the fixator 5 attached to a humerus 907.

FIGS. 8A, 8B, and 9A-9D show an external fixator 1000 that is another embodiment of the external fixator 5 of FIG. 3A. The external fixator 1000 includes a first portion 1010A and a second portion 1010B that are linked by a universal joint 1500. Similar to the universal joint 500 in the external fixator 5 of FIG. 3A, the universal joint 1500 allows the two portions 1010A and 1010B of the fixator body to be set at any desired angle, which in turn allows the fixation pins held in each of the two portions 1010A and 1010B of the fixator body to be arranged into a variety of angular configurations. Similar to the external fixator 5, a set of fixation pins can be held in the first portion 1010A of the external fixator 1000 through the pin holes 142 in the pin-holder 143 and another set of fixation pins can be held in the second portion 1010B of the external fixator 1000 through the pin holes 112a, 112b, 112c and 112d.

The universal joint 1500 is formed by hinge legs 1502a and 1502b of the first portion 1010A and 1504a and 1504b of the second portion 1010B, joined by a double-axle 1505. The universal joint 1500 can be locked by the hinge locking screws 1507a and 1507b are provided to lock the universal joint 1500 and lock the angular relationship between the first and second portions 1010A and 1010B.

In one embodiment, the locking function of the hinge locking screws 1507a and 1507b can be enhanced by providing diamond teeth surface finish (e.g. knurled surface finish) either on the interior surface of the hinge legs 1502a and 1502b or the surfaces on the double-axle 1505 that come in contact with one another. Such diamond teeth finish will increase the friction between the contacting surfaces when the hinge locking screws 1507a, 1507b are tightened. The first and second portions 1010A and 1010B of the fixator may be made from materials that are softer than the double-axle 1505 to further enhance this mechanical bite of the diamond teeth.

As shown in the cross-sectional views of FIGS. 9A and 9D, the double-axle 1505 of the universal joint 1500 is different from the double axle 505 of the external fixator 5 shown in FIGS. 3A and 3B. As shown in FIG. 9A, the hinge locking screw 1507a extends from the hinge leg 1504a to the hinge leg 1504b completely through the double-axle 1505 and holds the double-axle 1505 between the pair of hinge legs 1504 of the second portion 1010B. The hinge locking screw 1507a forms one of the two axle of the universal joint 1500 and allows the first and second portions 1010A and 1010B to be rotated about the hinge locking screw 1507a in the direction illustrated by the arrow K in FIG. 9B. The double-axle 1505 can be configured to have any appropriate shape as long as it fits within the universal joint configuration between the two sets of hinge legs 1502a, 1502b and 1504a, 1504b and accommodate the hinge locking screws 1507a, 1507b.

Because the hinge locking screw 1507a extends completely through the second portion 1010B, the hinge locking screw 1507a may be cannulated for K-wire alignment. The hinge locking screw 1507a shown in FIG. 9A is provided with a cannula 1508 that extends through the entire length of the hinge locking screw 1507a. This allows the user to shoot a K-wire through the cannula 1508 to where the user prefers to place the hinge formed by the universal joint 1500.

As shown in FIG. 9A, the hinge locking screw 1507a is provided with threaded tip (away from its head) and threadably engages one leg of the pair of hinge legs 1504a and 1504b. In this illustrate example, the hinge locking screw 1507a threadably engages the hinge leg 1504b. Tightening the hinge locking screw 1507a against the hinge leg 1504b will close the pair of hinge legs 1504a and 1504b together against the double-axle 1505 and lock the universal joint 1500 about the axle formed by the hinge locking screw 1507a. This prevents the two portions 1010A and 1010B from rotating in the direction of the arrow K.

The second axle of the universal joint 1500 is formed by the hinge locking screw 1507b. However, as shown in FIG. 9D, which is a cross-sectional view of the external fixator 1000 taken through the plane C-C in FIG. 9C that is perpendicular to the cross-sectional view shown in FIG. 9A, because the hinge locking screw 1507a extends completely through the double-axle 1505, the hinge locking screw 1507b can not extend completely through the double-axle 1505. Rather, the hinge locking screw 1507b threadably engages the double-axle 1505 while allowing the hinge leg 1502b of the first portion 1010A to rotate about the hinge locking screw 1507b in the direction illustrated by the arrow H in FIG. 9C. Tightening the hinge locking screw 1507b against the double-axle 1505 will lock the double-axle 1505 against the hinge leg 1502b and lock that hinge.

Because the hinge locking screw 1507b does not extend through the double-axle 1505, the opposite side of the double-axle 1505 is rotatably attached to the hinge leg 1502a by a hinge pin 1507c. The hinge pin 1507c may be securely attached to the hinge leg 1502a and extend into the double-axle 1505. For example, the hinge pin 1507c may be press-fitted into the hinge leg 1502a or welded to the hinge leg 1502a. The hinge pin 1507c in combination with the hinge locking screw 1507b comprise the second axle of the universal joint 1500.

The first portion 1010A of the external fixator 1000 is structurally equivalent to the first portion 110A of the external fixator 5. Similar to the first portion 110A, the first portion 1010A has an internally threaded bore 1111A extending longitudinally through the length of the first portion 1010A (see FIG. 9A). A pin-holder 143, shown and described in detail with reference to FIGS. 1A-1D, 2A, 2B and 3A, is received in a first end 1012 of the first portion 1010A of the external fixator 1000 and threadably engages the internally threaded bore 1111A. This configuration enables the pin-holder 143 to move longitudinally inside the first portion 1010A. The first and second portions 1010A and 1010B can have cylindrical shapes as shown in the illustrated example but they can have any appropriate shape.

The first portion 1010A is provided with a pair of diametrically opposed longitudinally extending slots 116 that cooperate with the guide pin 160 of the pin-holder 143 to guide the longitudinal movement of the pin-holder 143 and to keep the pin holes 142 aligned with the longitudinally extending slots 116. The first portion 1010A of the external fixator 1000 is also provided with at least one longitudinally extending slot 126 for accommodating the set screws 186 of the pin-holder 143. In the illustrated example, the set screws 186 thread into the pin-holder 143 in perpendicular orientation to the pin holes 142. Thus, the longitudinally extending slot 126 is located appropriately on the first portion 1010A to accommodate the set screws 186. The longitudinally extending slot 126 can be provided in the first portion 1010A as a diametrically opposed pair to allow the set screws 186 to be threaded into the pin-holder 143 from the opposite side of the external fixator 1000 if necessary.

FIG. 1C shows how a set of fixation pins 5a may be held by the pin-holder 143. Further details on how the pin-holder 143 holds fixation pins 5a and operate within the first portion 1010A is provided in the texts accompanying the FIGS. 1A-1D, 2A, 2B and 3A.

The second portion 1010B of the external fixator 1000 holds a set of fixation pins via the pin holes 112a, 112b, 112c and 112d, similar to the external fixator 5 of FIGS. 1A-1E and 3A. As shown in the cross-sectional views of FIGS. 9A and 9D, however, the second portion 1010B is provided with a pin-locking mechanism inside its tubular structure. The pin-locking mechanism comprises a threaded driving screw 1125 and a pin-locking block 1130. The threaded driving screw 1125 and the pin-locking block 1130 are configured to rotatably couple together similar to the way the pin-holders 143 and 243 of FIGS. 1C and 2A are coupled to the threaded driving screw 155. The threaded driving screw 1125 threadably engage the internal threaded bore 1111B of the second portion 1010B and the driving screw 1125 moves the pin-locking block 1130 inwardly or outwardly within the second portion 1010B by turning the driving screw. The driving screw 1125 is configured with a recess 1127 for receiving a tool (e.g. a wrench, screw driver, etc.) for turning the driving screw 1125.

The pin-locking block 1130 is appropriately sized to fit within the internal bore of the second portion 1010B and move longitudinally. The pin-locking block 1130 is provided with pin holes 1132 and 1133 that align with the pin holes 112a, 112b, 112c, and 112d of the second portion 1010B. As shown in the cross-section of FIG. 9D, when the pin holes 1132 and 1133 are aligned with the pin holes 112a, 112b, 112c, and 112d, fixation pins can be inserted through these holes. By driving the driving screw 1125 inwardly or outwardly, the pin-locking block 1130 is pushed inwardly and urged against the fixation pins that are extending through the pin holes 1132 and 1133 of the pin-locking block 1130. This results in the fixation pins being braced against the pin holes 112a, 112b, 112c, and 112d thus locking the fixation pins within the second portion 1010B.

Furthermore, according to another embodiment, the second portion 1010B of the external fixator 1000 may be provided with a lock indicator window 1020. As shown in FIG. 9A, the pin-locking block 1130 is provided with a lock indicator pin 1022 that is affixed into the pin-locking block 1130. The lock indicator pin 1022 protrudes from the pin-locking block 1130 and extends into the lock indicator window 1020. The lock indicator pin 1022 moves in longitudinal direction along with the pin-locking block 1130 and the position of the lock indicator pin 1022 within the lock indicator window 1020 indicates whether the pin-locking block 1130 is in a locked position or an unlocked position. For example, in the illustrated example, the lock indicator pin 1022 in the position shown in FIG. 9B, positioned away from the universal joint 1500, the pin-locking block 1130 is in an unlocked position. When the driving screw 1125 is threaded inwardly pushing the pin-locking block 1130 inward, the lock indicator pin 1022 would also slide inwardly within the lock indicator window 1020 and be closer to the universal joint 1500. It is noted that the longitudinal motion of the pin-locking block 1130 would be limited by the length of the lock indicator window 1020 in the longitudinal direction.

FIGS. 9F and 9H are lateral cross-sectional views of the second portion 1010B of the external fixator 1000 taken through the planes D-D and E-E of FIG. 9G and shows further detailed views of the pin-locking block 1130. As shown in the cross-sections, the pin-locking block 1130 is a cylindrical structure that has two flats surfaces. The interior bore 1111B in the region G shown in FIG. 9E is configured with corresponding inwardly protruding portions 1015. This configuration prevents the pin-locking block 1130 from rotating within the interior bore 1111B and maintain the alignment between the pin holes 1132, 1133 of the pin-locking block 1130 and the pin holes 112a, 112b, 112c, 112d of the second portion 1010B.

FIGS. 10A, 10B, and 10C-10F show an external fixator 2000 according to another embodiment. The external fixator 2000 includes a first portion 1010A and a second portion 1010C that are linked by a universal joint 1500, similar to the universal joint 1500 in the external fixator 1000 of FIG. 8A. The universal joint 1500 allows the two portions 1010A and 1010C of the fixator body to be set at any desired angle, which in turn allows the fixation pins held in each of the two portions 1010A and 1010C of the fixator body to be arranged into a variety of angular configurations.

The first portion 1010A and the universal joint 1500 of the external fixator 2000 have the same structures as the first portion 1010A and the universal joint 1500 of the external fixator 1000. As shown in FIGS. 10D and 10E, the universal joint 1500 allows the first portion 1010A and the second portion 1010C to rotate about the two axles of the universal joint 1500 in the directions indicated by the arrows K and H.

Unlike the second portion 1010B of the external fixator 1000, the second portion 1010C of the external fixator 2000 holds a set of one or more fixation pins via a set of one or more pin holes 1142 provided in a pin-holder 1143. The pin-holder is provided within the internal bore 1111C of the second portion 1010C and is longitudinally movable within the internal bore 1111C. Similar to the pin-holder 143 in the first portion 1010A, the pin-holder 1143 also comprises a set of set screws 1186 for locking the fixation pins in the pin holes 1142. The set screws 1186 are threaded into the pin-holder 1143 in orthogonal direction to the pin holes 1142 and urges against the fixation pins extending through the pin holes 1142 to lock the fixation pins within the pin holes 1142. However, unlike the pin-holder 143, the pin-holder 1143 does not have a driving screw 155 for moving the pin-holder 1143 longitudinally within the internal bore 1111C. Thus, the internal bore 1111C need not be threaded. While the longitudinal position of the pin-holder 143 in the first portion 1010A is controlled by the use of the driving screw 155, because the pin-holder 1143 is not threadably engaged to the internal bore 1111C of the second portion 1010C, the pin-holder 1143 freely slides within the internal bore 1111C.

The second portion 1010C is provided with at least one longitudinally extending slot 1126 for receiving the set screws 1186. In the illustrated example, one longitudinally extending slot 1126 is shown but another slot 1126 may be provided diametrically opposed from the one shown. This will allow the pin-holder 1143 to be axially rotated 180 degrees to change the direction of accessing the set screws 1186. The set screws 1186 act as guide pins as the pin-holder 1143 slides longitudinally within the internal bore 1111C. The second portion 1010C is also provided with a pair of diametrically opposed longitudinally extending slots 1116 (similar to the slots 116 in the first portion 1010A). The longitudinally extending slots 1116 are aligned with the pin holes 1142 and thus accommodate the fixation pins inserted into the pin holes 1142. The longitudinally extending slots 1116 also guide the fixation pins as the pin-holder 1143 moves in longitudinal direction.

In one embodiment, the pin holes 142 and 1142 may have oblong cross-section for purposes of enhancing the pin locking capability of the pin holes 142 and 1142. The oblong cross-section may be elongated in the direction parallel to the axial movement of the set screws 186 and 1186 threading into their respective pin-holders 143 and 1143. Because the pin holes 1142 have oblong cross-sectional shape, the widths of the pin holes 1142 are wider than the widths of the longitudinally extending slots 1116. This allows the fixation pins held within the pin holes 1142 to be pressed against the sides of the longitudinally extending slots 1116 and thus locking the position of the fixation pins and the pin-holder 1143.

As with the external fixator 1000, the external fixator 2000 can be used for both compression as well as distraction procedures. However, in the embodiment where the set of fixation pins held in the second portion 1010C of the external fixator 2000 are not fixed longitudinally, the external fixator 2000 allows greater adjustability in the positioning of the second portion 1010C in its longitudinal direction.

FIGS. 11A, 11B, and 11C-11F show an external fixator 3000 according to another embodiment. The external fixator 3000 includes a first portion 1010A and a second portion 1010C having the same structures as the first portion 1010A and second portion 1010C of the external fixator 2000 of FIG. 10A. However, in the external fixator 3000, the two portions 1010A and 1010C are linked by a double universal joint 3010. The double universal joint 3010 comprises an H-shaped body extending longitudinally between the two portions 1010A and 1010C. The H-shaped body of the double universal joint 3010 comprises two pairs of hinge legs 3011a, 3011b and 3013a, 3013b joined by a middle section 3012. Each of the two pairs of the hinge legs 3011a, 3011b and 3013a, 3013b form a universal joint with the hinge legs 1502a, 1502b and 1506a, 1506b. Each of the two universal joints formed are similar to the universal joint 1500 of the external fixator 1000 of FIG. 8A and functions in similar way to the universal joint 1500. However, because the external fixator 3000 comprises two universal joints the angular adjustability of the two portions 1010A and 1010C of the external fixator 3000 is greater.

A first universal joint is formed between the first portion 1010A and the double universal joint 3010 by the hinge legs 1502a, 1502b and the 3011a, 3011b hingeably joined by a first double-axle 1505A. Each of the two axes of the first double-axle 1505A are formed by the hinge locking screws 3021 and 3022 and the structure of the two axles are similar in structure to those formed by the hinge locking screws 1507a and 1507b of the external fixator 1000. The hinge locking screw 3022 extends completely through the first double-axle 1505A. The hinge locking screw 3022 also may be cannulated to provide a K-wire guide hole.

A second universal joint is formed between the second portion 1010C and the double universal joint 3010 by the hinge legs 1506a, 1506b and the 3013a, 3013b hingeably joined by a second double-axle 1505B. Each of the two axes of the second double-axle 1505B are formed by the hinge locking screws 3023 and 3024 and the structure of the two axles are similar in structure to those formed by the hinge locking screws 1507a and 1507b of the external fixator 1000. The hinge locking screw 3024 extends completely through the second double-axle 1505B. The hinge locking screw 3024 also may be cannulated to provide a K-wire guide hole.

Shown in FIGS. 12A-12D is an example of another universally flexible joint system 4000 that can be incorporated into the jointed fixators 5, 1000, 2000 and 3000 described herein. The joint system 4000 shown is a double jointed example. The joint system 4000 comprises two ball joints 4001 and 4002 connected by a center connecting piece 4010. Each of the ball joints 4001 and 4002 have terminal ends 4042A and 4042B that are configured to be attached to one of the two portions of the fixators.

For example, the terminal end 4042A of the ball joint 4001 can be attached to the first portion 1010A of the fixator 3000 and the terminal end 4042B of the ball joint 4002 can be attached to the second portion 1010C of the fixator 3000 by any appropriate methods. In one example, the terminal ends 4042A and 4042B and the corresponding mating portions of the first and second portions 1010A and 1010C can be configured to be press-fitted to one another or welded together. In another example, the terminal ends 4042A and 4042B and the corresponding mating portions of the first and second portions 1010A and 1010C can be configured to be threaded into each other by screw threads. In these examples, the ends of the first and second portions 1010A and 1010C having the hinge legs 1502a, 1502b and 1506a, 1506b would need to be reconfigured accordingly to be joined to the terminal ends 4042A or 4042B.

The two ball joints 4001 and 4002 are symmetrical in structure. Thus, the details of the ball joint 4001 will be described which is equally applicable to the ball joint 4002. The corresponding structures in ball joint 4002 are identified in the drawings with same numbers as in the ball joint 4001 with the trailing letter "B."

The ball joint 4001 comprises a ball-joint stem 4040A with a ball 4041A at one end and the terminal end 4042A at the other end. The ball-joint stem 4040A may be provided with a flange 4043A to act as a stop when a fixator portion such as 1010A is being attached to the terminal end 4042A. The ball 4041A is captured in a ball housing that comprises a first half 4030A and a second half 4020A that are configured to be threaded into each other while capturing the ball 4041A in between the two halves. The first and second halves 4030A, 4020A may be cross pinned to prevent the two halves from coming apart after assembly.

Figure 12A:
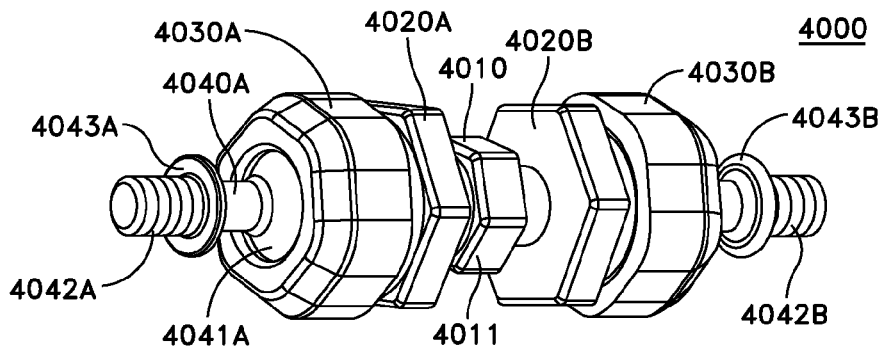
FIGS. 12A-12F are various views of another universally flexible joint according to another embodiment.
Figure 12B:
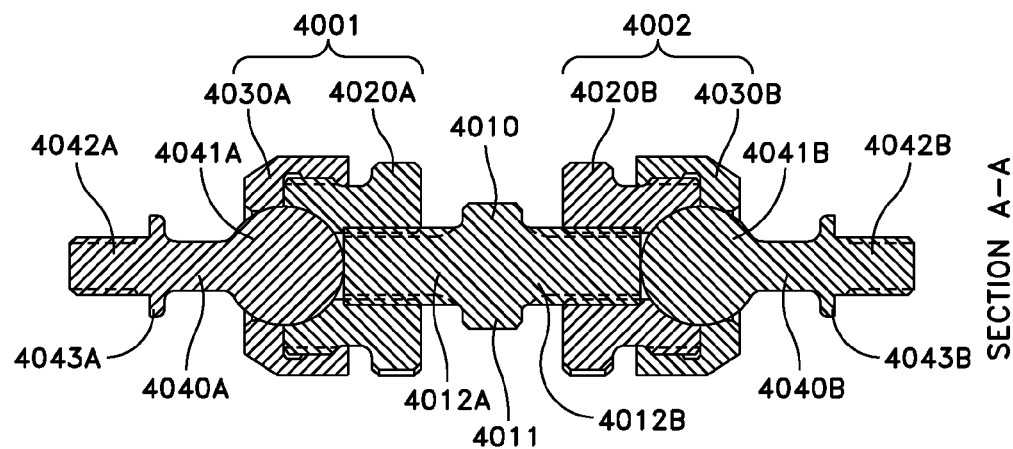
Figure 12C:
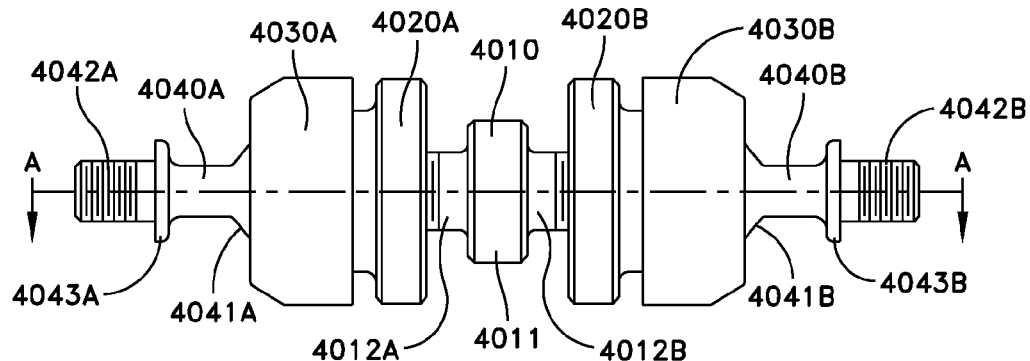
Figure 12F:
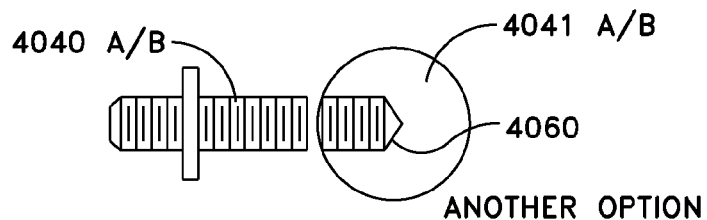
Figure 12D:
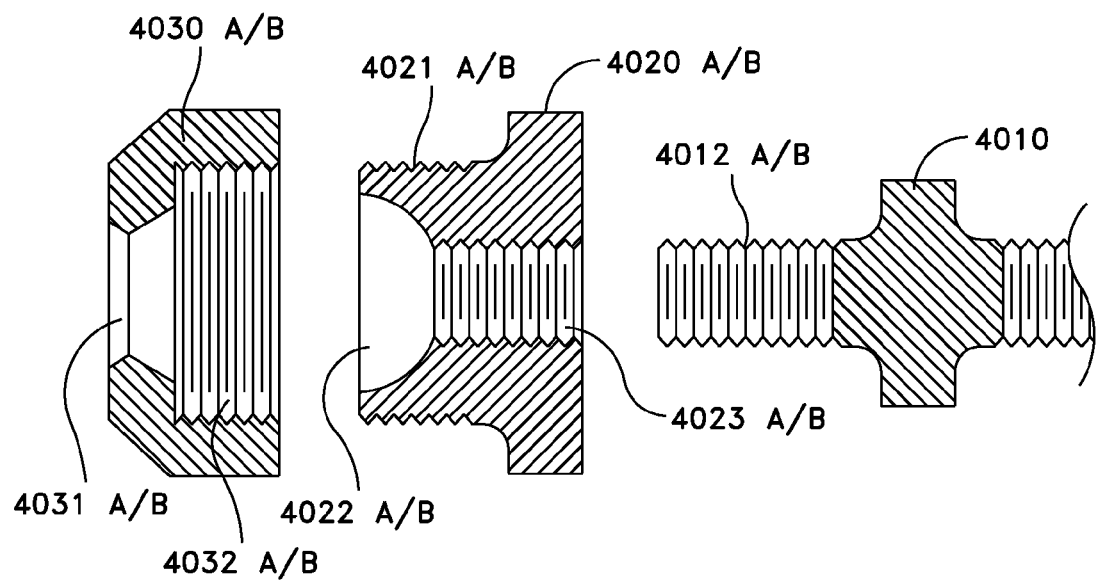
Figure 12E:
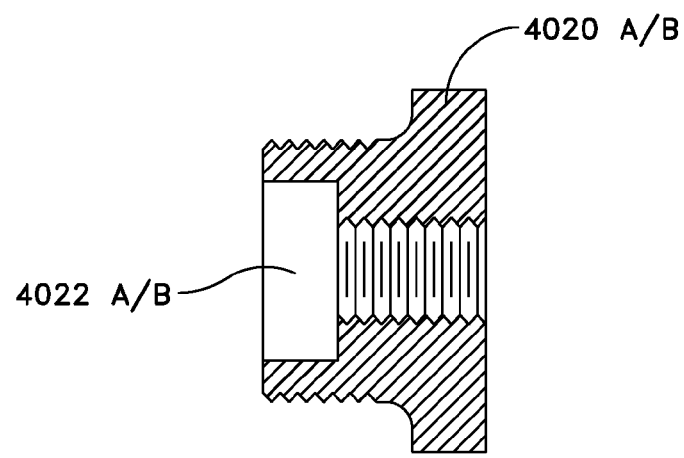

Referring to the exploded view in FIG. 12D, the first half 4030A of the ball housing has an opening 4031A at one end allowing the ball-joint stem 4040A to extend through. The first half 4030A is also provided with a female thread structure 4032A. The second half 4020A of the ball housing comprises a make thread structure 4021A for threadably mating with the female thread structure 4032A of the first half 4030A. The second half 4020A is also provided with a space 4022A for accommodating the ball 4041A. The second half 4020A is also provided with a threaded bore 4023A for receiving the first threaded stem 4012A of the center connecting piece 4010. As shown in FIGS. 12D and 12E, the space 4022A, 4022B for accommodating the ball 4041A, 4041B can have spherical curved contour or any other contour appropriate for holding the ball 4041A, 4041B within the ball housing.

FIG. 12F illustrates another embodiment of the ball-joint stem 4040A, 4040B. The ball 4041A, 4041B can be provided with a threaded hole 4060 and threadably attached to the threaded ball-joint stem 4040A.

The ball 4040A captured in the ball housing formed by the ball housing halves 4020A and 4030A is initially free spinning to allow the joint to be freely bent. To lock the ball joint 4001, the center connecting piece 4010 is then used to lock the ball joint 4001 by turning the center connecting piece 4010 in the locking direction which threads the first threaded stem 4012A further into the second half 4020A of the ball housing and urge against the ball 4041A. As shown in FIG. 12A, the center connecting piece 4010 is configured to have a nut-like structure 4011 to facilitate turning and locking the ball joint.

Referring to the FIG. 12B, in one embodiment, all the threaded components in one ball joint are threaded in the same direction. However, the threaded components in each of the two ball joints 4001 and 4002 are threaded in the opposite direction with respect to each other. For example, if the threaded components in the ball joint 4001 have left-handed threads the threaded components in the ball joint 4002 have right-handed threads and vice versa. This means that the two threaded stems 4012A and 4012B of the connecting piece 4010 are oppositely threaded. This allows the user to lock both ball joints 4001 and 4002 at the same time by turning the center connecting piece 4010 in one direction and unlock by turning it in the opposite direction. Alternatively, the ball joints 4001 and 4002 can be locked or unlocked independently by turning just one of the second half 4020A or 4020B with respect to the center connecting piece 4010.

Referring to FIGS. 13A, 14A-14D, an external fixator device 1 according to an embodiment is disclosed. The device 1 includes one or more fixation pins 5a each having a threaded end suitable for engaging a bone piece. The fixator device includes an elongated fixator body 10 having an internally threaded bore 11 extending longitudinally through the length of the fixator body 10. A pair of diametrically opposed longitudinally extending slots 16 are provided in the fixator body 10. A slidable sleeve 20 for capturing and translating the one or more first set of fixation pins 5a is slidably placed over the fixator body 10.

Figure 13B:
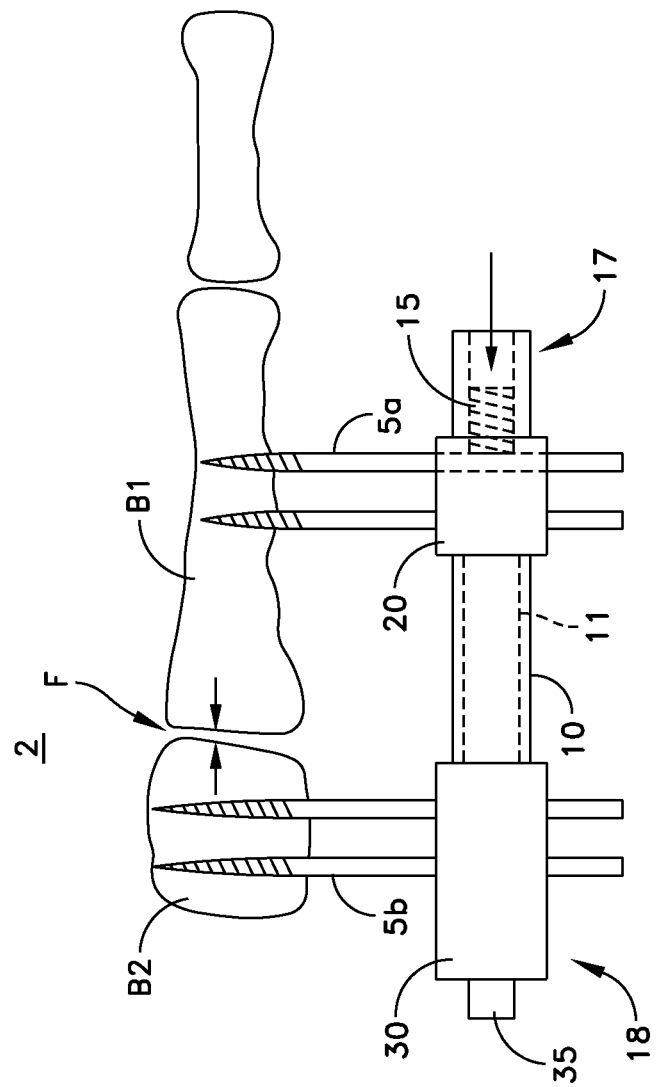
FIG. 13B is an illustration of an external fixator according to another embodiment.
Figure 14A:
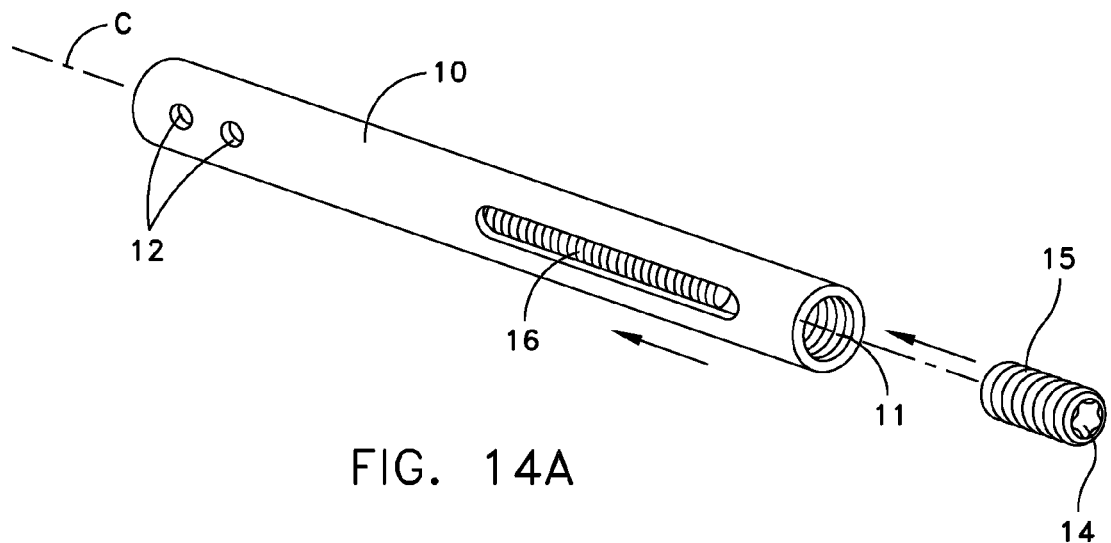
FIG. 14A is an illustration of the fixator body of the external fixator of FIG. 13A.
Figure 14B:
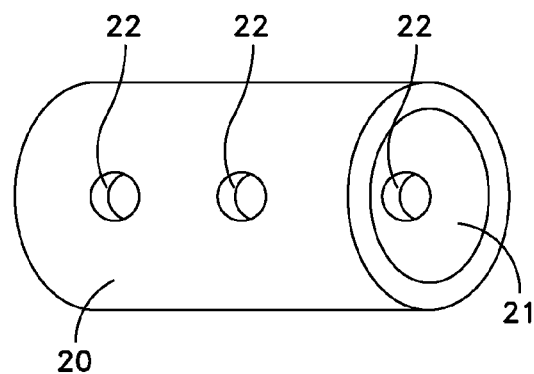
FIG. 14B is an illustration of the slidable sleeve for the fixator of FIG. 13A.

The slidable sleeve 20 has a longitudinally extending bore 21 in which the fixator body is slidably received. The slidable sleeve 20 can have a cylindrical shape as in the examples shown in the figures however it is not limited to the cylindrical shape. As discussed earlier, the outer shape of the fixator body 10 can be any appropriate shape and the longitudinally extending bore 21 of the sleeve 20 needs to match that cross-sectional shape. However, the outer shape of the sleeve 20 can be any desired shape. The slidable sleeve 20 also has a pair of diametrically opposed holes 22 for each of the one or more fixation pins 5a to be translated and locked by the slidable sleeve 20. Each of the fixation pin 5a passes through one pair of diametrically opposed holes 22 in the slidable sleeve 20 and the diametrically opposed slots 16 in the fixator body in an orthogonal orientation to the longitudinal axis C of the fixator body 10. As indicated in FIGS. 13B and 14A, driving set screw 15 is received in one end 17 of the fixator body 10 and threaded into the internally threaded bore 11 of the fixator body. The user can move the set screw into or out of the internally threaded bore 11 by turning the set screw with an appropriate tool. The driving set screw 15 is configured at one end to receive a tool such as an hex wrench, Robertson wrench, Torx wrench (star-shaped), screw driver, etc. For example, the driving set screw 15 illustrated in FIG. 14A is provided with a receptacle 14 configured to receive a Torx wrench.

Figure 13A:
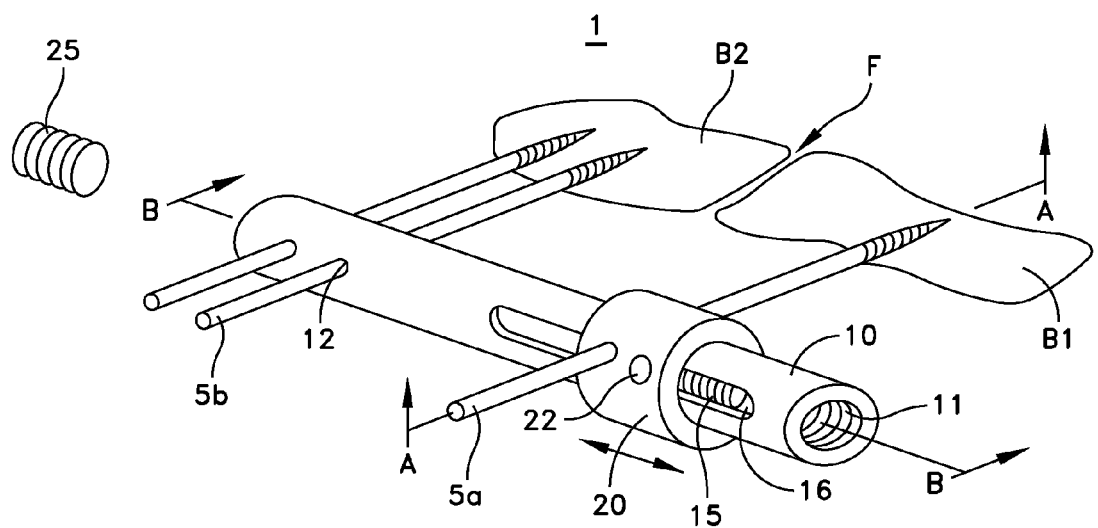
FIG. 13A is an illustration of an external fixator according to an embodiment.
Figure 14C:
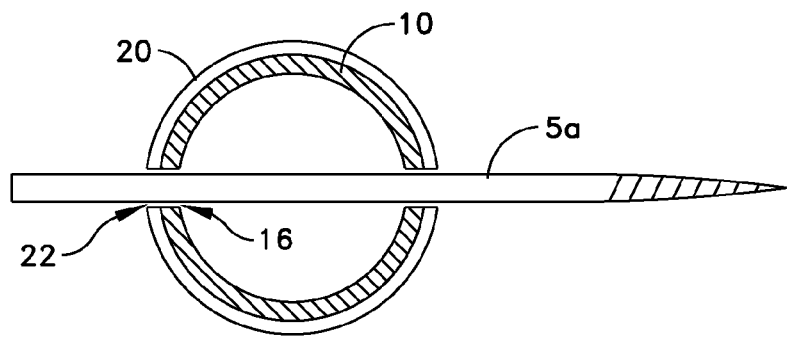
FIG. 14C is a lateral cross-sectional view of the fixator of FIG. 13A.
Figure 14D:
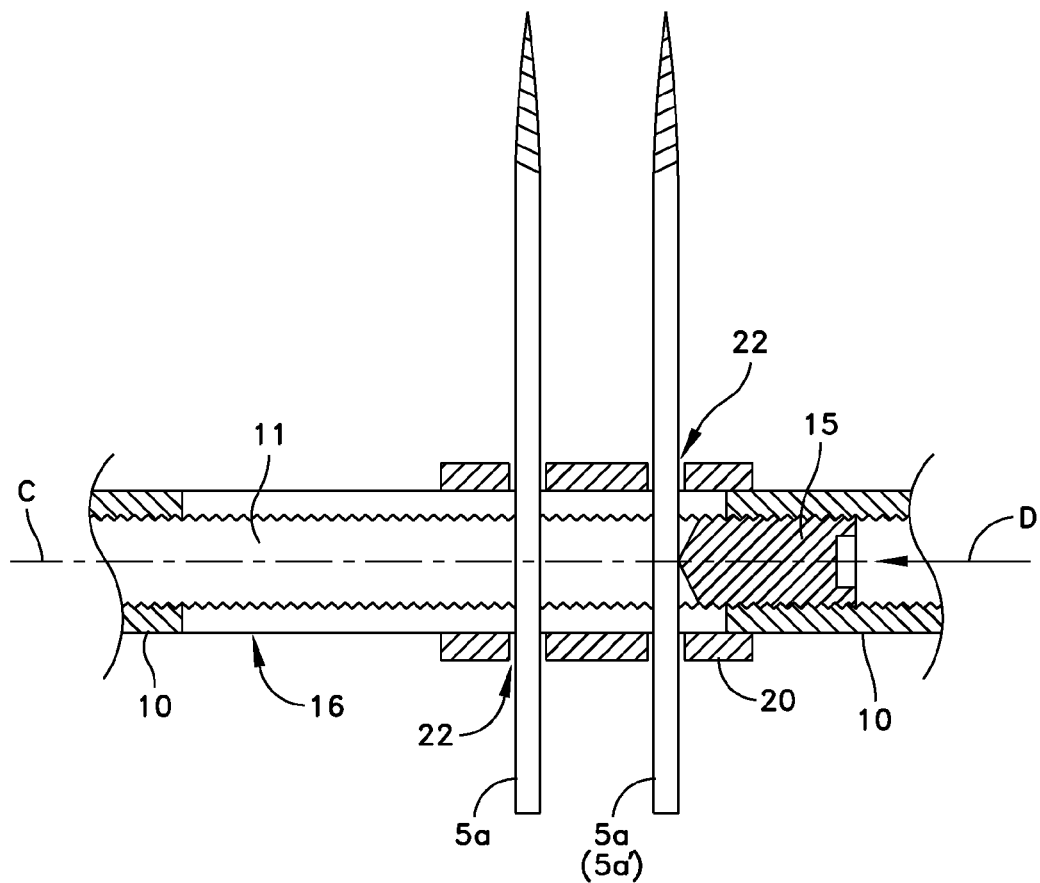
FIG. 14D is a longitudinal cross-sectional view of the fixator of FIG. 13A.
Figure 14E:
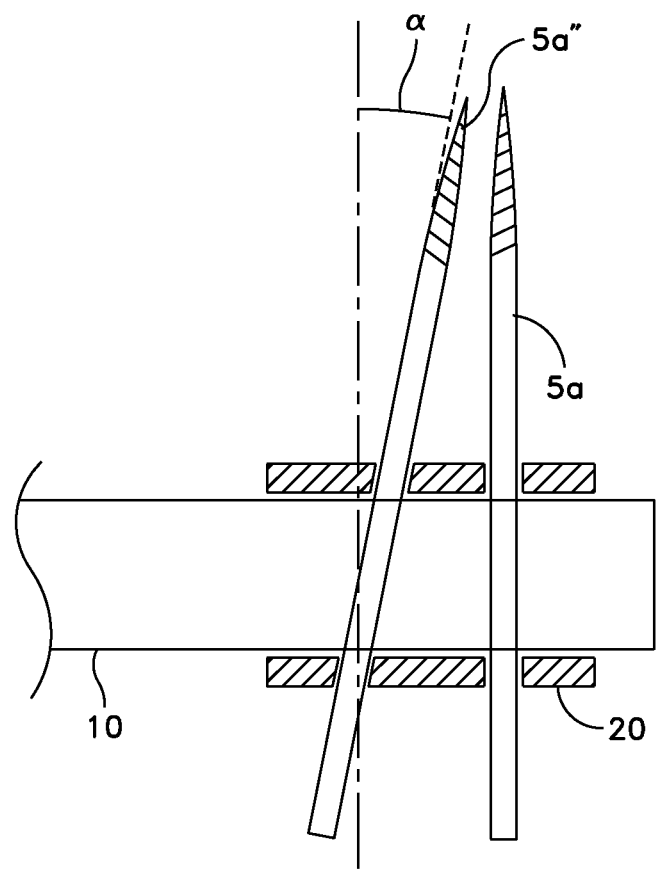
FIG. 14E is another longitudinal cross-sectional view of the fixator of FIG. 13A.

FIGS. 14C and 14D are cross-sectional views of the external fixator 1 of FIG. 13A taken through lines A-A and B-B, respectively. FIG. 14C illustrates the fixation pin 5a passing through the diametrically opposed pair of holes 22 and the pair of slots 16. FIG. 14D illustrates the driving set screw 15 being compressed against one of the fixation pins 5a (the one labeled as 5a'). By threading the driving set screw 15 into the threaded bore 11 of the fixator body 10 in the direction of the arrow D, the set screw 15 will push against the fixation pin 5a' and cause the assembly of the pins 5a and the slidable sleeve 20 to slide or translate with respect to the fixator body 10 in the direction of the arrow D. As the fixation pins 5a are translated, the slidable sleeve 20 maintains the pins' orientation with respect to the longitudinal axis C of the fixator body while the diametrically opposed longitudinal slots 16 in the fixator body 10 maintain the pins 5a on-axis. On-axis refers to the pins 5a traveling in the direction D along the longitudinal axis C of the fixator body. In this example, the fixation pins 5a are orthogonally oriented with respect to the longitudinal axis C. According to another aspect of the invention, however, the orientations of the fixation pins 5a are not limited to being orthogonal to the longitudinal axis C. To accommodate various arrangements of the bones being engaged with the device, each the fixation pins 5a can be at different orientation with respect to the longitudinal axis C and with respect to each other. In those embodiments, the holes 22 on the sleeve 20 will be appropriately positioned to accommodate the fixation pins 5a. Each pair of holes 22 for receiving one fixation pin would not be diametrically opposed. FIG. 14E shows an exemplary arrangement where one of the fixation pin 5a" is oriented at an angle α with respect to the adjacent fixation pin 5a so that the pins converge. If the fixation pins are arranged in converging configuration, they do not need to be threaded.

According to an embodiment, the external fixator device 1 further includes at least one pair of diametrically opposed pin holes 12 provided on the fixator body 10 near the fixator body's second end 18 for receiving one or more second set of fixation pins 5b through the fixator body. The second set of fixation pins 5b are for engaging a second bone piece. A pair of diametrically opposed pin holes 12 is provided for each of the fixation pins 5b. A locking set screw 25 is received in and threadably engages the internally threaded bore 11 of the fixator body for locking the second fixation pin 5b. Because the fixation pins 5b pass through and traverse the internally threaded bore 11 via the diametrically opposing holes 12, after the one or more fixation pins 5b are engaged in the second bone piece, the pin 5b can be locked in place by tightening the locking set screw 25 against the portion of the fixation pin 5b that is inside the threaded bore 11. Unlike the fixation pin 5a received in the first end 17 of the fixator body through the slidable sleeve 20, the position of the second fixation pin 5b along the length of the fixator body 10 is fixed and not slidable in axial direction with respect to the fixator body 10.

As illustrated in FIG. 13A, when the external fixator device 1 is used on a patient to fixate bone parts B1 and B2 to compress the fracture or an osteotomy site F (hereinafter referred to as the "bone repair site"), the adjustable or sliding end 17 of the fixator device is affixed to the bone part B1 by way of the first set of one or more fixation pins 5a held by the slidable sleeve 20. The second end 18 of the fixator device is affixed to the bone part B2 via the second set of one or more fixation pins 5b.

Because the fixation pins 5b in the second end 18 of the fixator device are not translatable or slidable, by applying a compression force against the first set of fixation pins 5a by threading the first set screw 15 further into the fixator body 10, the fixation pins 5a and 5b can be pushed towards each other. In turn, the bone parts B1 and B2 are pushed towards each other and apply a compression force at the bone repair site F.

Referring to FIGS. 13B and 15A-15C, an external fixator device 2 according to another embodiment is described. The fixator device 2 is substantially the same as the fixator device 1 of FIG. 13A except that its non-slidable second end 18 of its fixator body 10 is configured with a spring-loaded pin-locking cap 30 for locking the second fixation pins 5b in the fixator device. Like the fixator device 1, the fixator body 10 has at least one pair of diametrically opposed pin holes 12 near the fixator body's second end 18 for receiving a second fixation pin 5b through the fixator body.

Figure 15A:
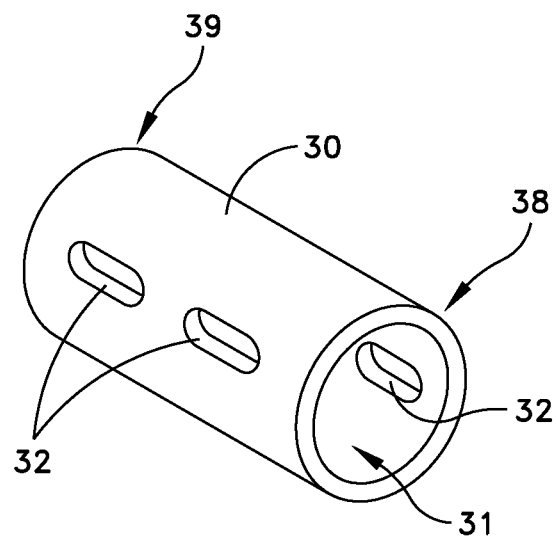
FIG. 15A is a perspective view of a pin locking cap.
Figure 15B:
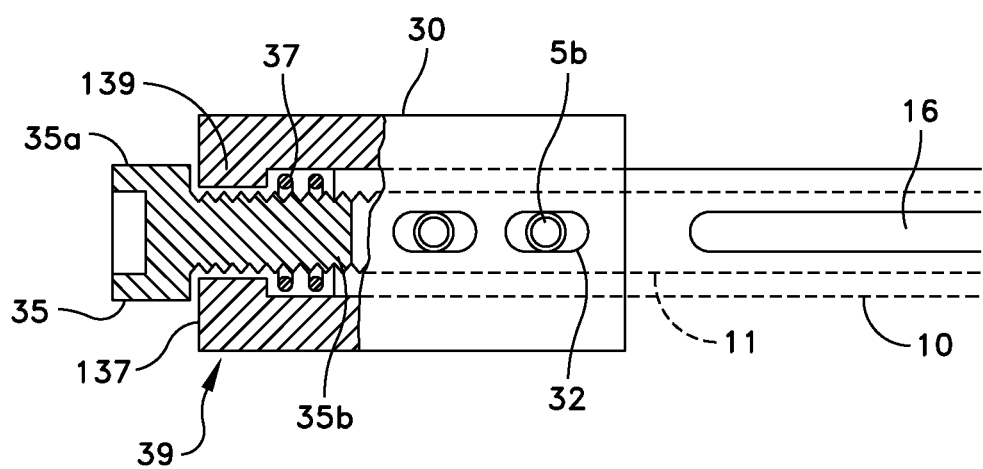
FIG. 15B is a partial sectional illustration of the pin locking cap of FIG. 15A in an assembled configuration in an unlocked position.
Figure 15C:
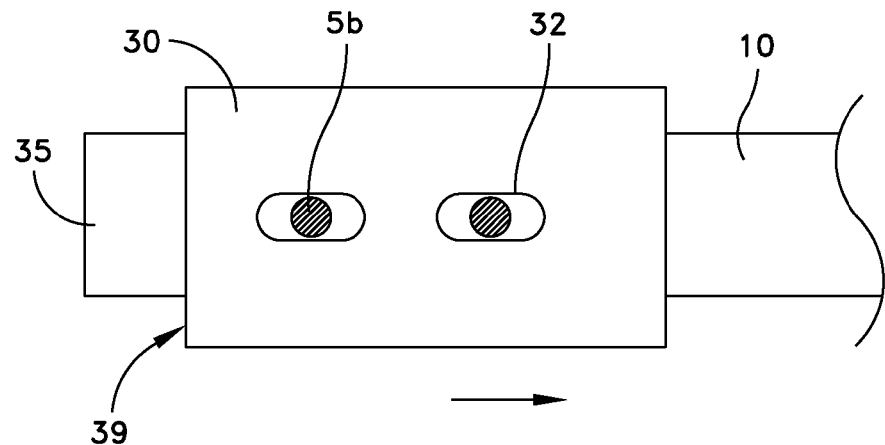
FIGS. 15C and 15D are illustrations showing how the spring-loaded pin locking cap 30 locks bone fixation pins.

As shown in FIGS. 15A-15D, the spring-loaded pin-locking cap 30 has a body with two open ends 38, 39. The pin locking cap 30 has a bore 31 for receiving the second end 18 of the fixator body 10. In the example shown where the fixator body 10 has a cylindrical shape, the bore 31 has an inside diameter that is substantially equal to the outer diameter of the fixator body 10 enabling the second end 18 of the fixator body to be received into the pin locking cap's first open end 38. The second open end 39 of the pin-locking cap 30 is configured to receive a locking screw 35 that is used to lock the second fixation pins 5b in the fixator device. The pin-locking cap 30 also is provided with at least one pair of diametrically opposed pin-locking slots 32. By aligning the pin-locking slots 32 and the pin holes 12 on the fixator body 10, a bone fixation pin 5b can be inserted through the aligned pin-locking slots 32 and the pin holes 12 as shown in FIG. 15C.

The second open end 39 of the pin locking cap 30 has an inwardly extending flange portion 139 with an opening 137 for receiving the locking screw 35 in the center. The locking screw 35 includes a head portion 35a and a threaded shaft portion 35b. The threads on the threaded shaft portion 35b matches the female threads on the threaded bore 11 of the fixator body 10 so that the locking screw 35 threads into the threaded bore 11. The opening 137 is sufficiently large to allow the threaded shaft portion 35b of the locking screw 35 to extend through the opening 137 and into the locking cap 30 but the head portion 35a of the locking screw 35 is configured and sized not to fit through the opening 137. The head portion 35a can be configured to receive a screw driver or other types of tools (e.g. socket wrench, Torx wrench, etc.) for turning the screw 35.

Figure 15D:
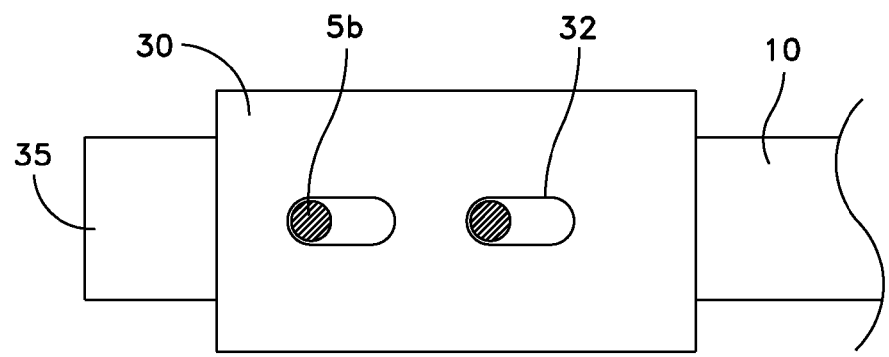

As shown in FIG. 15B, a coil spring 37 is provided within the pin locking cap 30 and positioned between the fixator body 10 and the flange portion 139. In an assembled but unlocked state, the coil spring 37 urges against the flange portion 139 pushing the fixator body 10 and the locking cap 30 apart but the locking screw 35 which is threaded into the inner bore 11 of the fixator body 10 holds the locking cap 30 in place. FIG. 15C shows the position of the second fixation pins 5b with respect to the pin locking slots 32 in the unlocked state. The pins 5b are freely positioned in the middle of the pin locking slots 32. To lock the fixation pins 5b, the locking screw 35 is threaded into the fixator body 10, which in turn pushes the pin-locking cap 30 in the same longitudinal direction until the pin locking slots 32 press against the fixation pins 5b preventing the fixation pins 5b from moving as shown in FIG. 15D.

Referring to FIGS. 20A-20C, an offset pin clamp 190 for use in securing the second set of fixation pins 5b at the non-adjustable end 18 of the fixator body 10 according to another embodiment is disclosed. The offset pin clamp 190 holds the second set of fixation pins 5b offset from the fixator body 10. The fixation pins 5b being offset from the fixator body 10 refers to the fact that in this embodiment, the fixation pins 5b do not go through the fixator body as in the previously described embodiments. The offset pin clamp 190 includes a longitudinally extending bore 191 in which the fixator body 10 is received. One or more pin holes 192 are provided in the offset pin clamp 190 for receiving and holding one or more fixation pins 5b. The pin holes 192 are provided in the portion of the offset pin clamp 190 above the bore 191.

Provided in combination with the pin holes 192 is a threaded hole 194 for receiving a countersink-head screw 196. The threaded hole 194 is oriented orthogonal to the bore 191 and the pin holes 192. The countersink-head screw 196 includes a flared head 196h and a shaft 196s. The shaft 196s is threaded to threadably engage the hole 194.

The threaded hole 194 of the offset pin clamp 190 extends from the top surface of the offset pin clamp 190 to the bore 191 so that the countersink-head screw 196 can extend into the space defined by the bore 191. The hole 194 includes a countersink 194h for accommodating the flared head 196h of the countersink-head screw 196 and a threaded lower portion 194t. The countersink 194h intersects the pin holes 192 forming openings 197 connecting the hole 194 and the pin holes 192. The diameter of the pin holes 192 is appropriately sized for the fixation pins 5b, thus allowing the fixation pins 5b inserted into the pin holes 192 to be exposed and slightly protrude through the openings 197. Once the fixation pins 5b are inserted into the pin holes 192, the countersink-head screw 196 is threaded into the hole 194. The threaded portion 196t of the countersink-head screw 196 threadably engages the threaded lower portion 194t of the hole 194 and the flared head 196h of the countersink-head screw 196 will come in contact with the portion of the fixation pins 5b that is exposed through the opening 197 and secures the position of the fixation pins 5b by clamping down on them.

Referring to FIG. 20C, the offset pin clamp 190 is shown in conjunction with a fixator body 10 that is received within the bore 191 of the clamp 190. The fixation pins 5b are held in the pin holes 192. The offset pin clamp 190 is also provided with a locking set screw 195 for securing the offset pin clamp 190 onto the fixator body 10. The offset pin clamp 190 is configured with a second threaded hole 193 for threadably receiving the locking set screw 195. Because the offset pin clamp 190 can be placed anywhere along the length of the fixator body 10 and axially rotatable about the fixator body 10 before locking its position with the locking set screw 195, the user can adjust the location and angular attitude of the second set of fixation pins 5b. This adds additional versatility to the external fixator device.

Figure 13C:
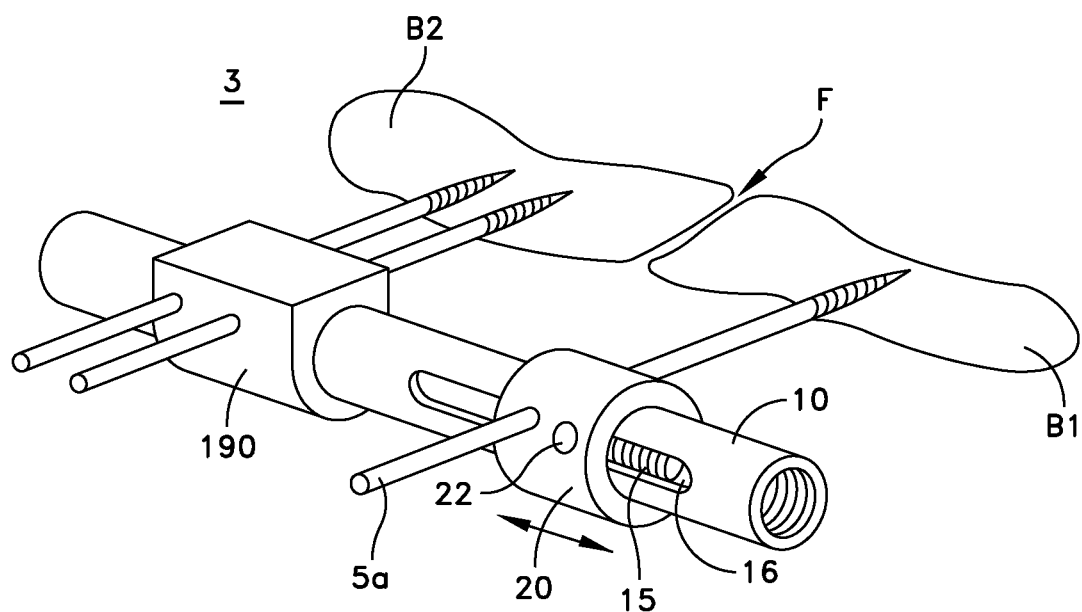
FIG. 13C is an illustration of another embodiment of external fixator.

Referring to FIG. 13C, according to an embodiment, an external fixation device 3 includes the fixator body 10 having the slidable sleeve 20, shown in FIG. 13A, for holding the first set of one or more fixation pins 5a at first end 17 of the fixator body 10 and provided with the offset pin clamp 190 at the second end 18 of the fixator body 10 for holding the second set of one or more fixation pins 5b. This embodiment of the external fixation device can be used for both compression as well as distraction of two bone pieces, one of the two bone pieces being affixed to the first set of fixation pins 5a and the second bone piece being affixed to the second set of fixation pins 5b.

Figure 16:
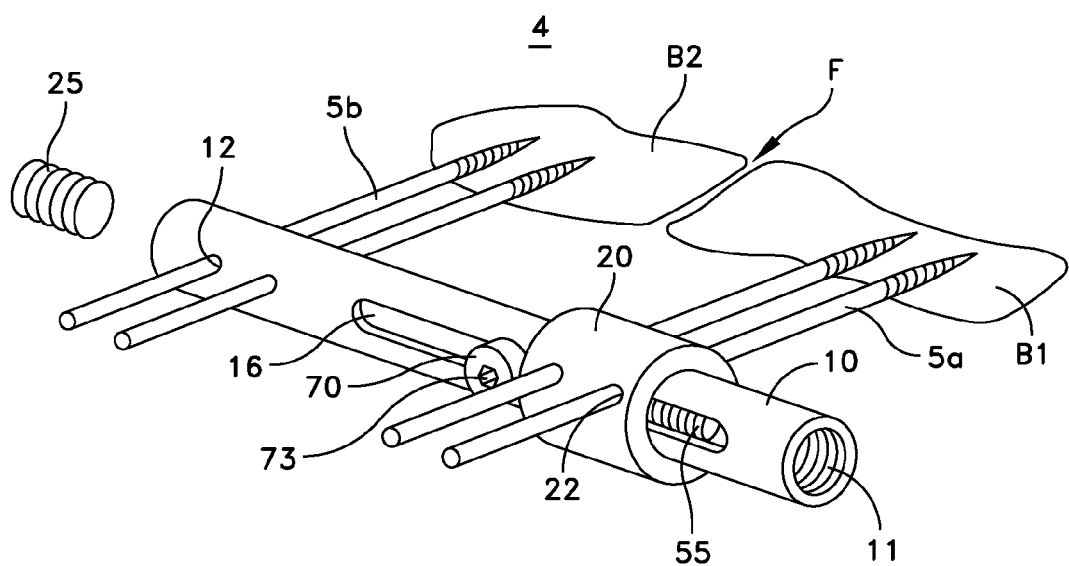
FIG. 16 is an illustration of an external fixator according to another embodiment.
Figure 17A:
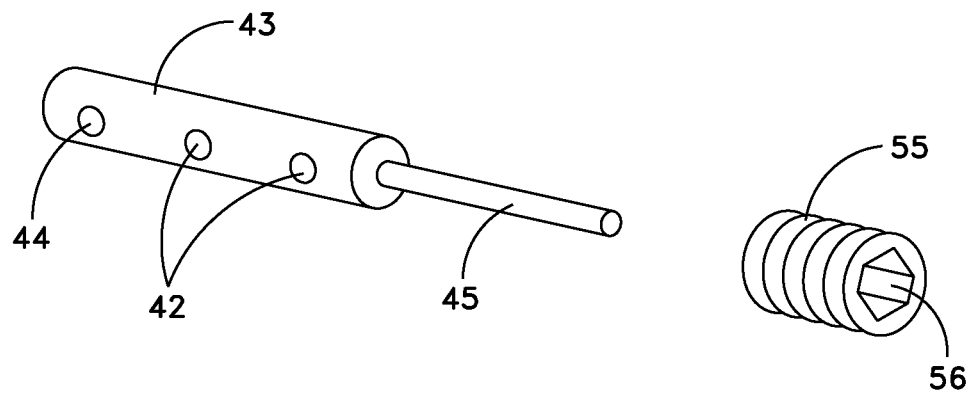
FIG. 17A is a detailed illustration of another embodiment of a driving set screw and the associated fixation pin holder.
Figure 17B:
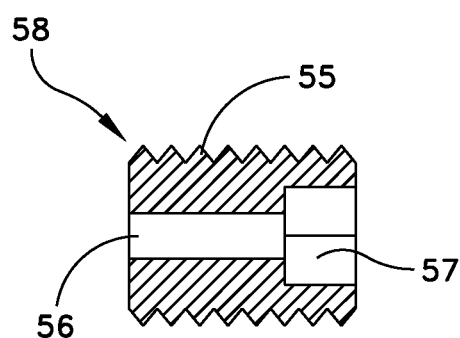
FIG. 17B is a cross-sectional view of the driving set screw of FIG. 17A.
Figure 17C:
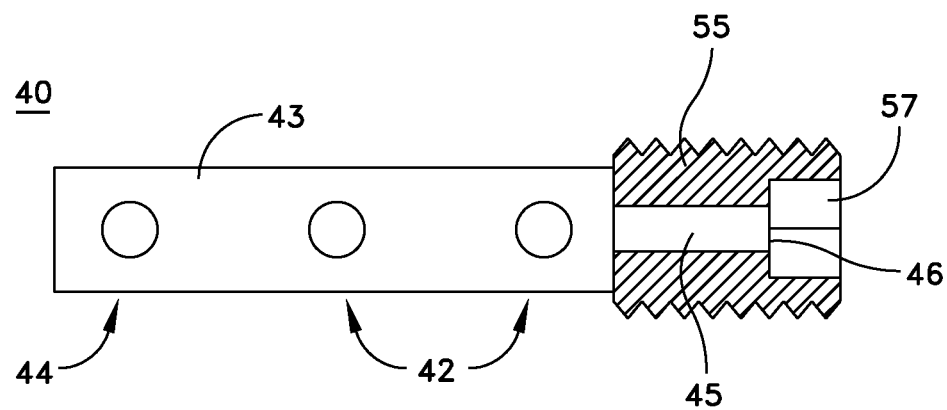
FIG. 17C is a longitudinal cross-sectional view of the fully assembled driving set screw of FIG. 17A.
Figure 17D:
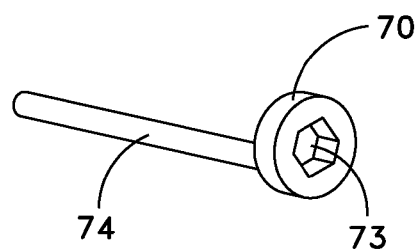
FIG. 17D is an illustration of a cam component of the external fixator of FIG. 16.
Figure 17E:
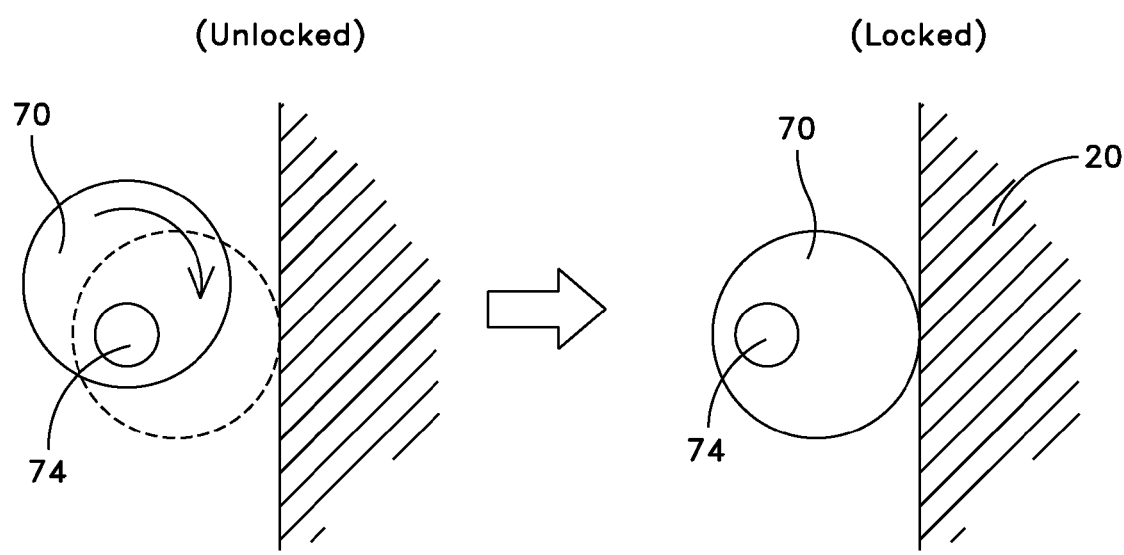
FIG. 17E is an end view of the cam of FIG. 17D.

Referring to FIGS. 16-17E, according to another embodiment, an external fixator device 4 for fixating bone parts includes the fixator body 10, the slidable sleeve 20 for holding the first set of one or more fixation pin 5a as shown in FIG. 13A, and a pin-holding set screw 40. The pin-holding set screw 40 is received in one end of the fixator body 10 and threadably engages the internally threaded bore 11 of the fixator body. The pin-holding set screw 40 includes a cam 70 that is used to lock the position of the fixation pins 5a.

FIGS. 17A-17E show the structural details of the pin-holding set screw 40 assembly. The pin-holding set screw 40 includes a cannulated threaded head portion 55 and an elongated pin holder 43 having at least one pin hole 42 for passing the fixation pin 5a therethrough. The elongated pin holder 43 is rotatably attached to the cannulated threaded head portion 55, the pin holder 43 being in axial alignment with the longitudinal axes of the cannulated threaded head portion 55 and the threaded bore 11 of the fixator body 10 so that the threaded head portion 55 can freely rotate about the longitudinal axis of the pin-holding set screw 40 with respect to the elongated pin holder 43.

The threaded head portion 55 is provided with a cannula 56 extending longitudinally therethrough. One end of the threaded head portion 55 is configured with a socket 57 (see FIG. 17B) appropriately structured for receiving a tool, such as a screw driver or one of a variety of wrenches, for turning the head portion 55. The elongated pin holder 43 is provided with a center stem 45 that extends longitudinally from one end and extends through the cannula 56 of the threaded head portion. During assembly of the set screw 40 assembly, after the center stem 45 is inserted through the cannula 56, the tip 46 of the center stem 45 is peened or appropriately flared as shown in the cross-sectional view in FIG. 17C to hold the pin holder 43 and the threaded head portion 55 together. The attachment, however, is sufficiently loose so that the threaded head portion 55 and the pin holder 43 axially rotate with respect to each other. The center stem 45 effectively functions as the rotational axle for the threaded head portion 55. The inner surface of the cannula 56 and the outer surface of the center stem 45 are appropriately finished to minimize any friction between the two contacting surfaces.

The pin-holding set screw 40 is inserted, with the pin holder 43 first, into the threaded bore 11 near the adjustable end 17 of the fixator body 10 so that the pin holes 42 provided in the pin holder 43 is accessible through the longitudinal slots 16 of the fixator body 10. After the slidable sleeve 20 is slid over the fixator body 10, the pin holes 22 in the slidable sleeve 20 and the pin holes 42 in the pin holder 43 are aligned with the longitudinal slots 16 so that fixation pins 5a can be inserted through each pair of the diametrically opposed pin holes 22 of the sleeve 20 while passing through the pin holes 42 in the pin-holding shaft 43 as shown in FIG. 16. Assembled in this manner, because the cannulated threaded head portion 55 is configured to threadably engage the threaded bore 11, by turning the threaded head portion 55, the pin-holding set screw 40 can be translated in axial direction within the threaded bore 11.

The pin holes 42 provided on the pin-holding shaft 43, if there are more than one, are spaced apart appropriately and bore through the longitudinal axis of the pin holder 43 to align with the one or more pairs of the pin holes 22 provided in the slidable sleeve 20. This allows the fixation pins 5a to be inserted through the diametrically opposed pairs of pin holes 22, the longitudinal slots 16, and the pin holes 42 when the pin-holding set screw 40 is positioned inside the fixator body 10. Because the pin holder 43 and the threaded head portion 55 are rotatable with respect to each other, the threaded head portion 55 can be turned within the threaded bore 11 while the first set of one or more fixation pins 5a are held by the slidable sleeve 20 and the pin holder 43. By turning the threaded head portion 55, the thread engagement between the head portion 55 and the threaded bore 11 allows the whole sliding assembly of the pin-holding set screw 40, the fixation pins 5a and the slidable sleeve 20 to slide up and down the fixator body 10 along the path defined by the longitudinal slots 16.

From the assembly described above, it will be understood that the orientation of the fixation pins 5a with respect to the fixator body 10 is determined by the configuration of the pin holes 22 in the slidable sleeve 20 and the pin holes 42 in the pin-holding set screw 40. In an embodiment, that orientation is orthogonal to the longitudinal axis C of the fixator body 10.

The elongated pin holder 43 is also provided with a camshaft receiving hole 44 near its end opposite from the center stem 45. In the assembled state of the external fixation device 4, a cam 70 is received into the camshaft receiving hole 44. As shown in FIG. 17D, the cam 70 has a camshaft portion 74 which is rotatably fitted into the camshaft receiving hole 44. The camshaft receiving hole 44 is spaced apart from the pin holes 42 by a desired distance so that when the fixation pins 5a are positioned through the slidable sleeve 20 and the pin holder 43, the cam 70 is located adjacent to the slidable sleeve 20 as shown in FIG. 16.

As shown in the end view of the cam in FIG. 17E, the camshaft portion 74 is off-centered with respect to the cam 70 thus providing the cam action when the cam is turned. Preferably, the cam 70 is in contact with the slidable sleeve 20 when the cam 70 is in an unlocked position without any space between the cam 70 and the slidable sleeve 20, which allows immediate cam action as the cam 70 is turned from the unlocked position to the locked position. Preferably, the cam 70 is provided with a socket 73 appropriately shaped for receiving a tool for turning the cam 70.

As shown in FIG. 16, the non-slidable end 18 of the external fixator 4 can be configured similar to the non-slidable end 18 of the external fixator 1 illustrated in FIG. 13A. The second set of one or more fixation pins 5b are inserted through the at least one pair of diametrically opposed pin holes 12 provided in the fixator body 10 and locked with the locking set screw 25 threadably engaged into the threaded bore 11 from the non-slidable end 18.

In affixing the external fixator 4 to the bone pieces to be repaired, the first set of fixation pins 5a are placed in a desired position (typically defined by their distance from the second set of fixation pins 5b that are held at the other end of the fixator body 10) on the fixator body 10. The first set of one or more fixation pins 5a and the second set of one or more fixation pins 5b are affixed into their respective bone parts by threading the fixation pins into the bone parts. Once the fixation pins 5a and 5b are affixed into their respective bone parts, the second set of fixation pins 5b are locked. The second set of fixation pins 5b can be locked at the non-adjustable end 18 of the fixator body 10 by the same means described above in connection with the embodiments shown in FIGS. 13A and 13B. The first set of fixation pins 5a are locked by the use of the cam 70 as described above. Then the bone parts are compressed by threading the pin-holding set screw 40 into the fixator body 10 and urging against the first set of fixation pins 5a.

According to another embodiment, the external fixator 4 includes the slidable sleeve 20 and the cam 70 as shown in FIG. 16 but the non-slidable end 18 of the device is configured as shown in the embodiments of FIGS. 13B and 15A-15D for holding the second set of one or more fixation pins 5b.

According to another embodiment, the external fixator 4 includes the slidable sleeve 20 and the cam 70 as shown in FIG. 16 but the non-slidable end 18 of the device is configured with the offset pin clamp 190 shown in FIGS. 20A-20C for holding the second set of one or more fixation pins 5b.

Figure 18A:
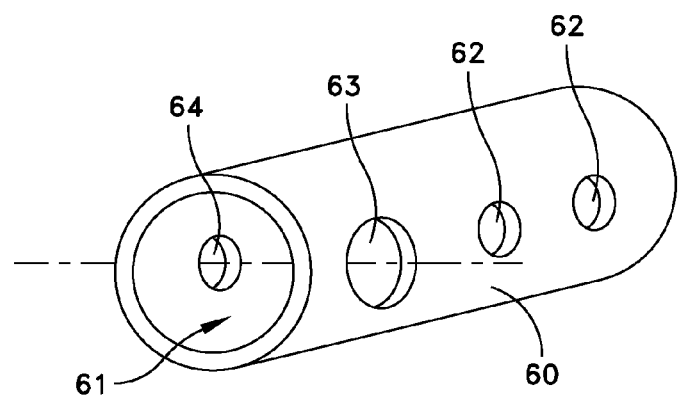
FIG. 18A is an illustration of another embodiment of a slidable sleeve that can be used in conjunction with the driving set screw of FIG. 17A.
Figure 18B:
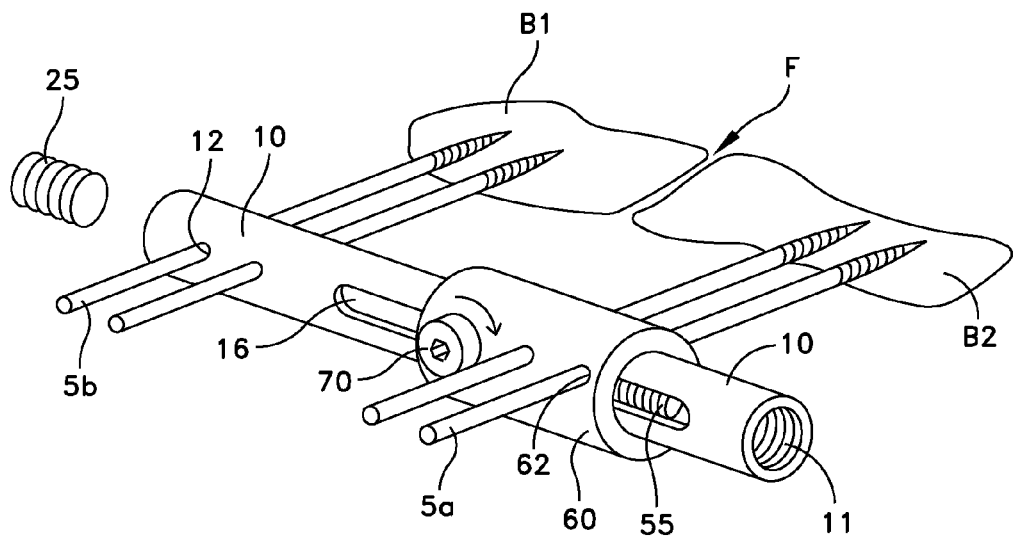
FIG. 18B is an illustration of an external fixator utilizing the slidable sleeve of FIG. 17A.

Referring to FIGS. 18A and 18B, another embodiment of a slidable sleeve 60 for use in conjunction with the pin-holding set screw 40 is disclosed. Similar to the slidable sleeve 20 of FIG. 16, the slidable sleeve 60 is provided with at least one pair of diametrically opposed pin holes 62 for receiving a fixation pin 5a. The slidable sleeve 60 is provided with an additional pair of diametrically opposed holes 63, 64 are provided for receiving the cam 70. The camshaft 74 extends through the front-side hole 63 on the slidable sleeve 60, through the camshaft receiving hole 44 of the pin-holding shaft 43, and rotatably fitted into the back-side hole 64 so that the cam 70 can be turned between its lock and unlock positions. The holes 63, 64 and 44 are positioned with respect to the fixation pin holes 62 and 42 such that the cam 70 is sufficiently close to the adjacent fixation pin 5a to lock the fixation pin. As with the external fixation device 4 of FIG. 16, the second set of fixation pins 5b at the non-adjustable end 18 of the fixator body 10 can be locked by the same means described above in connection with the embodiments shown in FIGS. 13A and 13B.

According to another embodiment, an external fixation device includes the fixator body 10, the slidable sleeve 60 described above for holding the first set of one or more fixation pins 5a and at least one pair of diametrically opposed pin holes 12 provided on the fixator body 10 near the fixator body's second end 18 similar to the external fixator device 1 of FIG. 13A. Each pair of diametrically opposed pin holes 12 are for receiving a second fixation pin 5b.

According to another embodiment, an external fixation device includes the fixator body 10, the slidable sleeve 60 described above for holding the first set of one or more fixation pins 5a and the spring-loaded pin-locking cap 30 described above in reference to FIG. 13B for locking the second set of fixation pins 5b at the non-adjustable end 18 of the fixator body 10.

According to another embodiment, an external fixation device includes the fixator body 10, the slidable sleeve 60 described above for holding the first set of one or more fixation pins 5a and the offset pin clamp 190 described above in reference to FIGS. 20A-20C for holding the second set of one or more fixation pins 5b at the non-slidable end 18 of the fixator body 10.

Figure 19A:
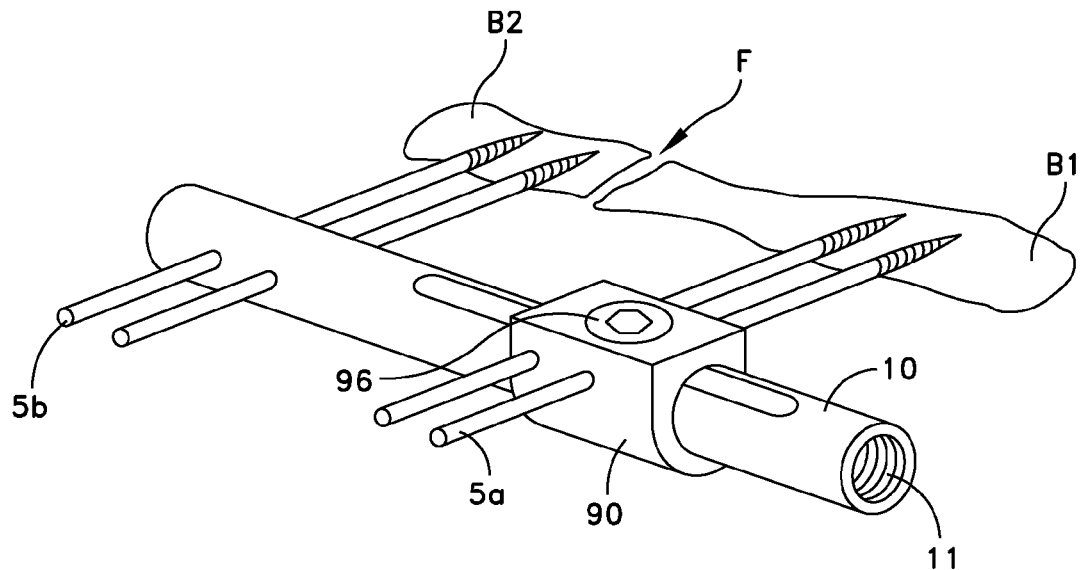
FIG. 19A is an illustration of a slidable sleeve according to another embodiment.
Figure 19B:
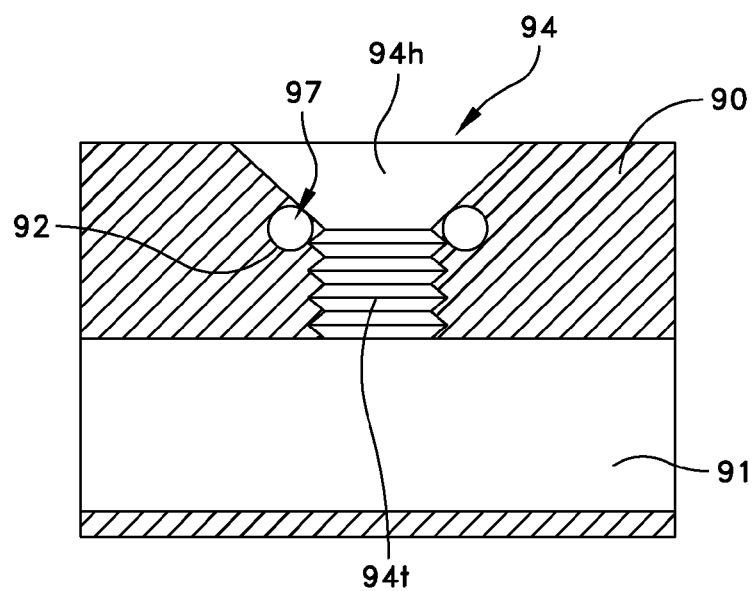
FIG. 19B is a longitudinal cross-sectional illustration of the slidable sleeve of FIG. 19A.

Referring to FIGS. 19A-19D, another embodiment of a slidable sleeve 90 for use in conjunction with the fixator body 10 is disclosed. The slidable sleeve 90 includes a longitudinally extending bore 91 in which the fixator body 10 is slidably received. One or more pin holes 92 are provided in the slidable sleeve 90 for receiving and holding one or more fixation pins 5a and the slidable sleeve 90 is configured to hold the fixation pins 5a offset from the fixator body 10. The fixation pins 5a being offset from the fixator body 10 refers to the fact that in this embodiment, the fixation pins 5a do not go through the fixator body 10 as in the case of the slidable sleeves 20 and 60. This is shown in FIG. 19B, which is a longitudinal cross-sectional view of the slidable sleeve 90. The pin holes 92 are provided in the portion of the slidable sleeve 90 above the bore 91 i.e. offset from the bore 91.

Figure 19C:
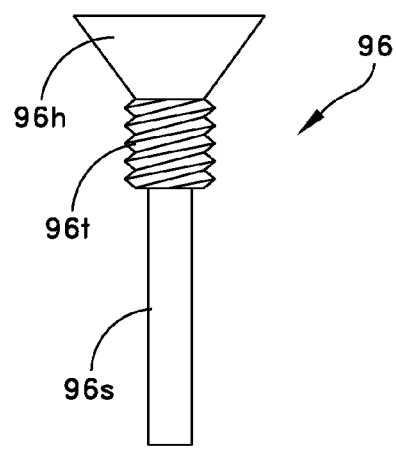
FIG. 19C is an illustration of a countersink-head screw used in conjunction with the slidable sleeve of FIG. 19A.

Provided in combination with the pin holes 92 is a threaded hole 94 for receiving a countersink-head screw 96. The threaded hole 94 is oriented orthogonal to the bore 91 and the pin holes 92. FIG. 19C is an illustration of an exemplary countersink-head screw 96. The screw 96 includes a flared head 96h and a shaft 96s. The shaft 96s may be threaded to threadably engage the hole 94. Preferably, the shaft 96s has a threaded portion 96t near the head 96h and the remainder of the shaft is not threaded.

The threaded hole 94 of the slidable sleeve 90 extends from the top surface of the slidable sleeve 90 to the bore 91 so that the countersink-head screw 96 can extend into the space defined by the bore 91. The hole 94 includes a countersink 94h for accommodating the flared head 96h of the countersink-head screw 96 and a threaded lower portion 94t. The countersink 94h intersects the pin holes 92 forming openings 97 connecting the hole 94 and the pin holes 92. The diameter of the pin holes 92 is appropriately sized for the fixation pins 5a thus allowing the fixation pins 5a inserted into the pin holes 92 to be exposed and protrude through the openings 97. Once the fixation pins 5a are inserted into the pin holes 92, the countersink-head screw 96 is threaded into the hole 94. The threaded portion 96t of the countersink-head screw 96 threadably engages the threaded lower portion 94t of the hole 94 and the flared head 96h of the countersink-head screw 96 will come in contact with the portion of the fixation pins 5a that is exposed through the openings 97 and clamp down on the fixation pins 5a.

Figure 19D:
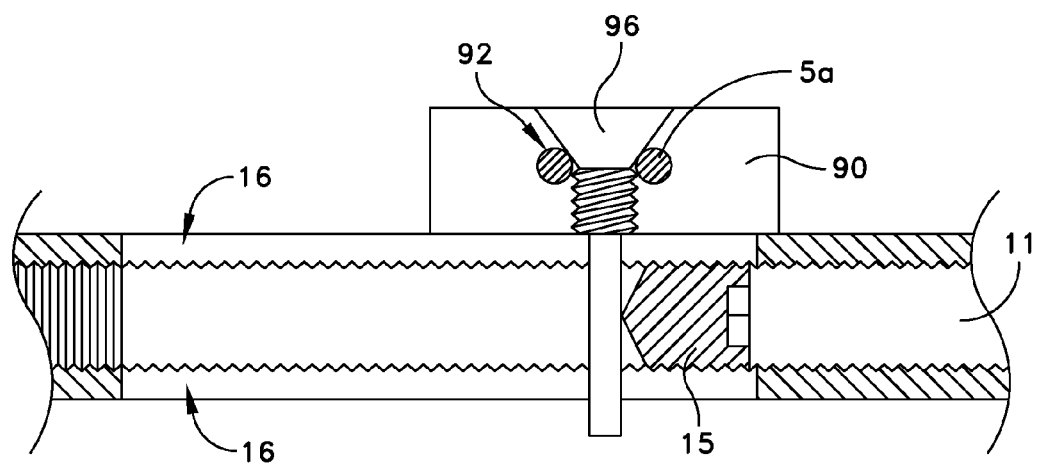
FIG. 19D is a cross-sectional illustration of a fixator body utilizing the slidable sleeve of FIG. 19A.

Referring to FIG. 19D, the slidable sleeve 90 is shown in conjunction with a fixator body 10 that is received within the bore 91 of the sleeve 90 and fixation pins 5a are held in the pin holes 92. When the countersink-head screw 96 is threaded into the hole 94 for clamping the fixation pins 5a as shown, the unthreaded shaft portion 96s of the countersink-head screw extends through the longitudinal slots 16 of the fixator body and into the threaded bore 11 of the fixator body 10. By using the driving set screw 15 threaded into the bore 11 of the fixator body 10, the slidable sleeve 90 and, thus, the fixation pins 5a, can be moved by engaging and pushing the shaft 96s of the countersink-head screw 96. Preferably, the portion of the shaft 96s that comes in contact with the driving set screw 15 is not threaded so that the contact engagement between the set screw and the shaft 96s is smooth.

The pin holes 92 extend through the slidable sleeve 90 at an angle generally orthogonal to the fixator body 10 as shown in FIG. 19A. However, the pin holes 92 can be oriented in the slidable sleeve 90 at different angles with respect to the fixator body 10 as desired for particular applications.

According to an embodiment, an external fixation device includes the fixator body 10, the slidable sleeve 90 described above for holding the first set of one or more fixation pins 5a and at least one pair of diametrically opposed pin holes 12 provided on the fixator body 10 near the fixator body's second end 18 similar to the external fixation device 1 of FIG. 13A. Each pair of diametrically opposed pin holes 12 are for receiving a second fixation pin 5b. As in the fixation device 1, after the fixation pin 5b is engaged in a bone part, the second set of one or more fixation pins 5b can be locked in place by tightening the locking set screw 25 against the portion of the fixation pin 5b that is traversing through the threaded bore 11.

According to another embodiment, an external fixation device includes the fixator body 10, the slidable sleeve 90 described above for holding the first set of one or more fixation pins 5a and the spring-loaded pin-locking cap 30 described above for locking the second set of one or more fixation pins 5b at the non-adjustable end 18 of the fixator body 10.

In another embodiment, the longitudinal slots 16 extend along a substantial portion of the length of the fixator body 10 and two of the slidable sleeves 90 are provided on the fixator body 10 to allow the device to be used as a bone compression device. Each of the two slidable sleeves 90 would hold a set of one or more fixation pins 5a. With the two sets of fixation pins affixed to their respective bone pieces, the slidable sleeves 90 can be urged toward each other to compress the two bone pieces together.

Figure 22:
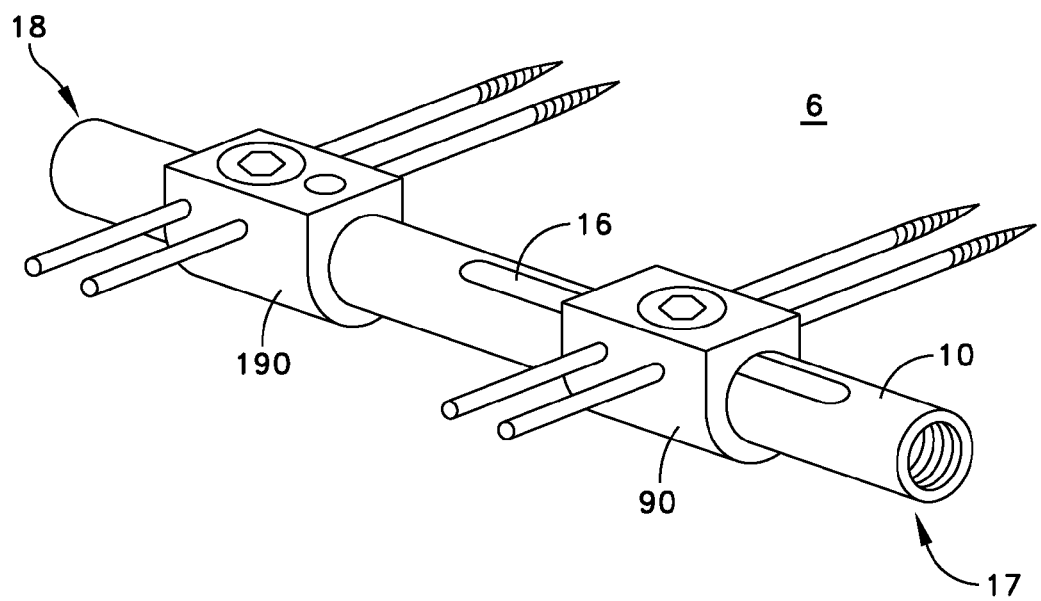
FIG. 22 is an illustration of an external fixator according to another embodiment.

Referring to FIG. 22, according to another embodiment, an external fixator device 6 may include an elongated fixator body 10, a slidable sleeve 90 of FIG. 19A at one end of the fixator body 10 holding the first set of fixation pins 5a and cooperating with the longitudinal slots 16 of the fixator body 10, and an offset pin clamp 190, described above in reference to FIGS. 20A-20C, at the second end 18 of the fixator body for holding the second set of one or more fixation pins 5b. The second set of fixation pins 5b can be affixed to a bone part B1 and locked into position on the fixator body 10 by way of the offset pin clamp 190. The first set of one or more fixation pins 5a can be affixed to a second bone part B2 and attached to the fixator body 10 via the slidable sleeve 90. This external fixator device 6 can be used for distraction or compression of the two bone parts by threading a set screw 15 into the threaded bore 11 of the fixator body 10 from the appropriate end of the fixator body 10 with respect to the slidable sleeve 90.

For example, by inserting and threading the set screw 15 at the first end 17 of the fixator body 10, the fixator 6 can be used to put the two bone parts B1, B2 in compression by pushing the slidable sleeve 90 (and thus the first set of fixation pins 5a) towards the offset pin clamp 190. By inserting and threading the set screw 15 at the second end 18 of the fixator body 10, the fixator 6 can be used to distract the two bone parts B1, B2 apart by pushing the slidable sleeve 90 away from the offset pin clamp 190. The set screw 15 can be inserted into the threaded bore 11 of the fixator body 10 from the second end 18 because the offset pin clamp 190 does not have any components that protrude into the threaded bore 11. The mechanism by which the slidable sleeve 90 is moved along the fixator body 10 using the set screw 15 is described above in connection with FIGS. 19A-19D.

Figure 21:
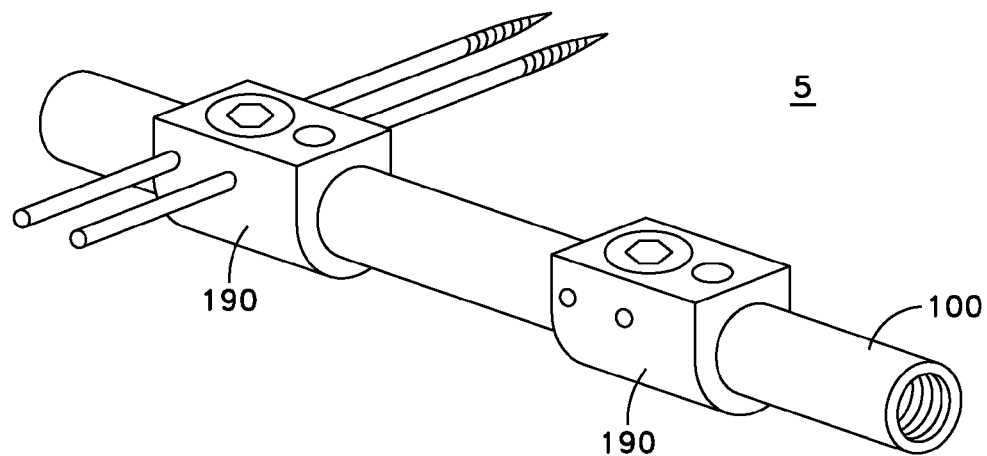
FIG. 21 is an illustration of an external fixator according to another embodiment.

Referring to FIG. 21, two or more offset pin clamps 190 can be used with a fixator body 100 to configure an external fixator device 5 where the fixation pins held by each of the offset pin clamps can be adjusted to any location along the length of the fixator body 100. Because the offset pin clamp 190 does not require any of its components to protrude into its longitudinally extending bore 191, the fixator body 100 can be a hollow tube or a solid rod.

Figure 23A:
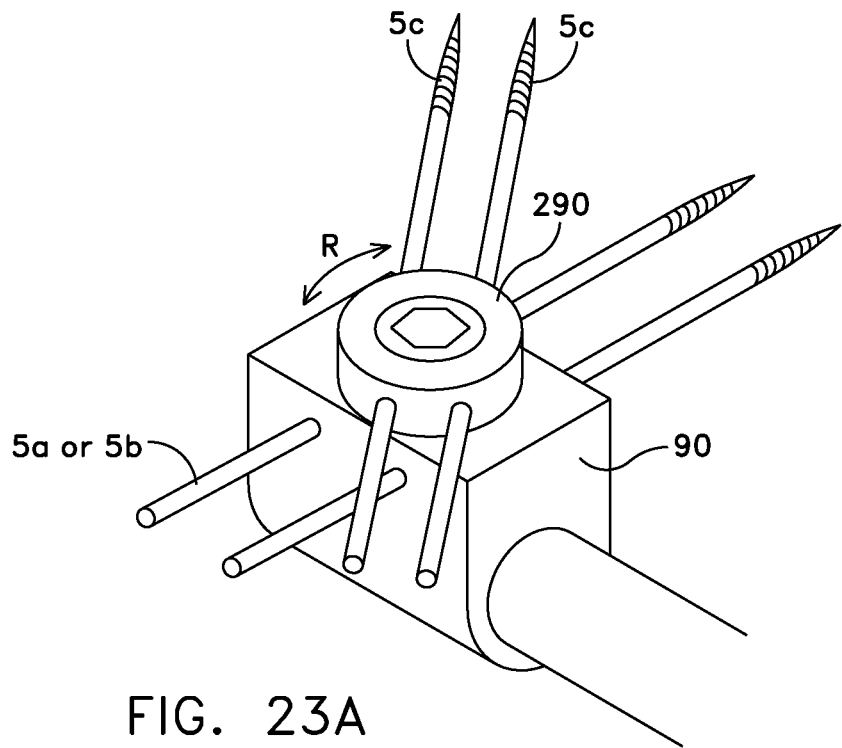
FIG. 23A is an illustration of the slidable sleeve of FIG. 19A in combination with a rotatable pin clamp attachment.

Referring to FIG. 23A, a rotatable pin clamp 290 that can be used in combination with the slidable sleeve 90 or the offset pin clamp 190 is disclosed. FIG. 23A shows the rotatable pin clamp 290 that is assembled in combination with the slidable sleeve 90 described earlier in connection with FIGS. 19A-19D. The rotatable pin clamp 290 is configured to hold an additional set of one or more fixation pins 5c in addition to the one or more fixation pins 5a held by the slidable sleeve 90. The rotatable pin clamp 290 is configured to be rotated about the longitudinal axis of the countersink-head screw 96 as represented by the arrow R in FIG. 23A.

Figure 23B:
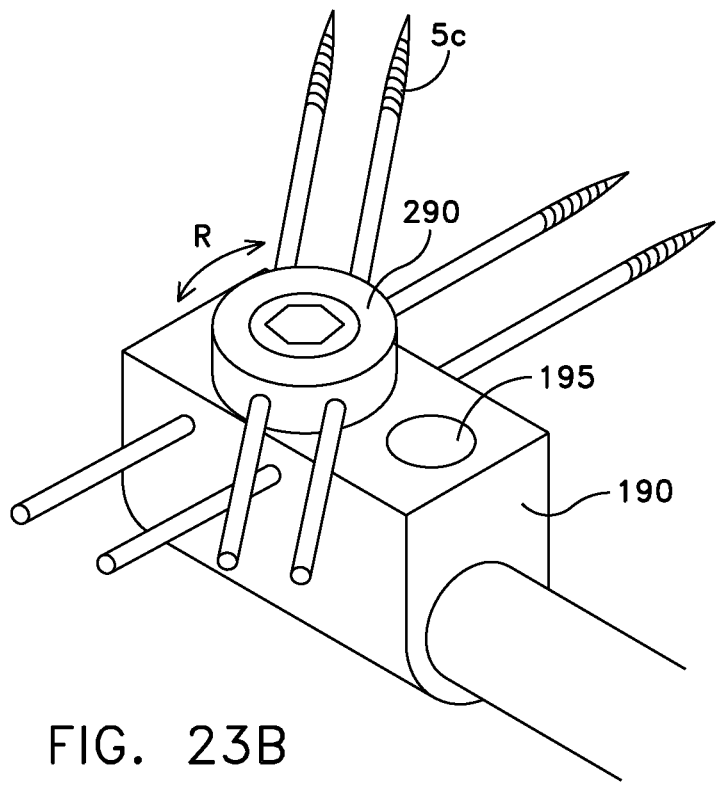
FIG. 23B is an illustration of the offset pin clamp of FIG. 20A in combination with a rotatable pin clamp attachment.

As illustrated, the rotatable pin clamp 290 holds another set of one or more fixation pins 5c further offset (with respect to the first set of one or more fixation pins 5a) from the fixator body 10. This provides additional adjustability and adaptability to the external fixation device by allowing the fixation pins 5c to be affixed to bone parts positioned at different orientation with respect to the external fixation device. FIG. 23B shows the rotatable pin clamp 290 that is assembled in combination with the offset pin clamp 190 discussed earlier in connection with FIGS. 20A-20C and holds additional set of one or more fixation pins 5d.

Figure 23D:
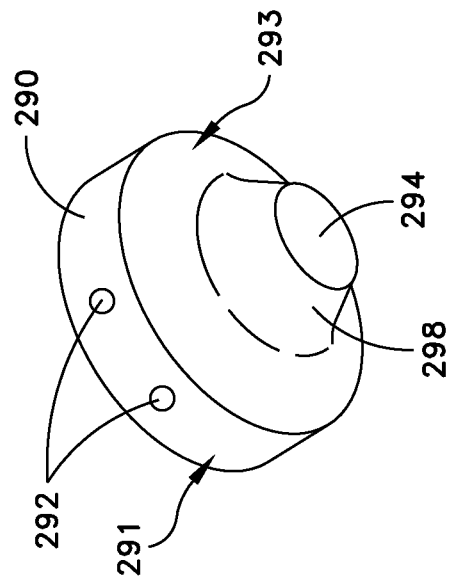
FIG. 23D is a detailed illustration of the rotatable pin clamp attachment.

FIG. 23D is a more detailed illustration of the rotatable pin clamp 290. The exemplary rotatable pin clamp 290 illustrated has a disc-shaped body but it can have any outline shape as appropriate. The clamp 290 includes a top side 291 and a bottom side 293 and is provided with a hole 294 extending from the top side 291 to the bottom side 293 for receiving the countersink-head screw 96. On the bottom side 293 of the clamp 290 is a protruding flange 298 around the hole 294. The contour of the protruding flange 298 mirrors the contour of the countersinks 94h, 194h of the slidable sleeve 90 and the offset pin clamp 190, respectively. The hole 294 is configured with a countersink at its top side for receiving the flared head 96h, 196h of the countersink-head screws 96, 196.

Figure 23C:
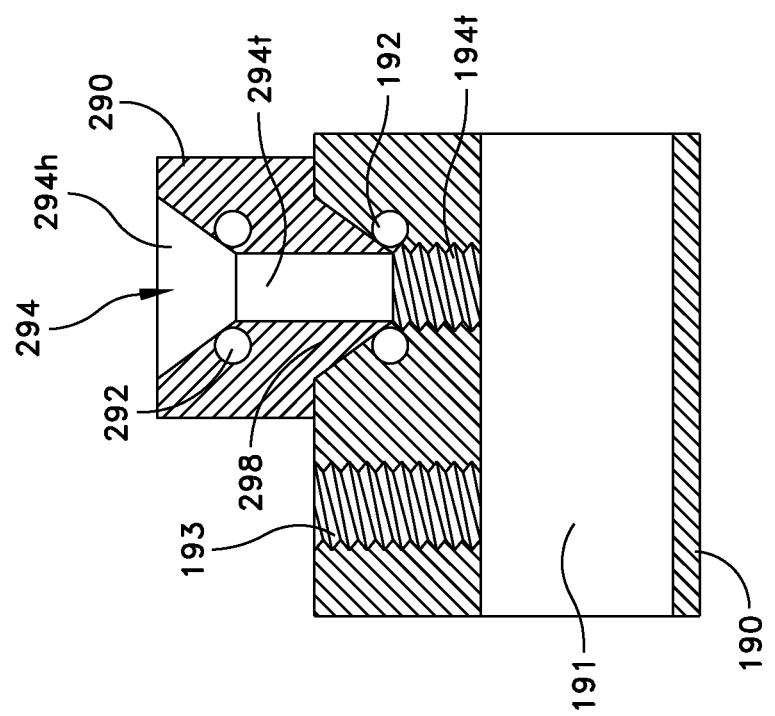
FIG. 23C is a longitudinal cross-sectional illustration of the assembly of FIG. 23B.

As shown in the cross-sectional view FIG. 23C, when the rotatable pin clamp 290 is stacked on top of the offset pin clamp 190 the protruding flange 298 mates into the countersink 194h of the offset pin clamp 190 and the hole 294 functions as an extension of the hole 194 of the offset pin clamp 190. Preferably, the hole 294 is not threaded and when the countersink-head screw 196 is inserted into the hole 294 the countersink-head screw 196 threadably engages the threaded portion 194t of the hole 194 in the offset pin clamp 190. Thus, the first fixation pins 5a held in the pin holes 192 and the fixation pins 5c held in the pin holes 292 of the rotatable pin clamp 290 are clamped and secured by threading the countersink-head screw 196 into the hole 194. The flared head 196h will clamp down on the fixation pins 5c held in the pin holes 292 and in turn the protruding flange 298 will clamp down on the fixation pins 5a held in the pin holes 192.

In the embodiment where a rotatable pin clamp 290 is assembled in combination with the slidable sleeve 90, the cross-sectional structure is similar to the one shown in FIG. 23C except that the slidable sleeve 90 does not have the second threaded hole 193 for threadably receiving a locking set screw 195.

The embodiments described in the foregoing disclosure are presented as examples. The scope of the present invention is to be limited only by the following claims.

What is claimed is:

1. An orthopedic device for fixating bone parts using two sets of one or more bone fixation pins, the orthopedic device comprising:
   a fixator body having a first part and a second part, the first and second parts being connected by a joint, the first part having an internally threaded bore extending longitudinally therethrough, the second part having a bore extending longitudinally therethrough;
   a first pair of opposed longitudinally extending slots in the first part of the fixator body;
   a first pin-holder received within and threadably engaging the internally threaded bore of the first part and configured to removably hold a first of the two sets of one or more bone fixation pins extending through the first pair of opposed longitudinally extending slots, the pin-holder longitudinally movable within the first part for controlling the position of the set of bone fixation pins within the first part;
   a second pair of opposed longitudinally extending slots in the second part of the fixator body;
   a second pin-holder received within the bore of the second part and configured to removably hold a second of the two sets of one or more bone fixation pins extending through the second pair of opposed longitudinally extending slots, the pin-holder longitudinally movable within the second part.

2. The orthopedic device of claim 1, wherein the joint is a universal joint.

3. The orthopedic device of claim 2, wherein the universal joint comprising a double-axle member providing two axes of rotation for the universal joint; and
   a cannulated hinge-locking pin extending completely through the double-axle along one of the two axes of rotation, the cannulated hinge-locking pin providing a cannula for receiving a K-wire.

4. The orthopedic device of claim 1, wherein the joint comprises two universal joints.

5. The orthopedic device of claim 1, wherein the joint comprises two ball joints.

6. The orthopedic device of claim 1, wherein the first pin-holder further comprises a driving screw rotatably attached to the pin-holder and threadably engaging the internally threaded bore of first part of the fixator body for moving the pin-holder longitudinally within the fixator body.

7. The orthopedic device of claim 1, further comprising the two sets of one or more bone fixation pins.

* * * * *